US012734247B2

(12) United States Patent
Sen Gupta et al.

(10) Patent No.: US 12,734,247 B2
(45) Date of Patent: Sep. 15, 2026

(54) COMPOSITIONS AND METHODS FOR TARGETED AMPLIFICATION OF COAGULATION AND PHAGOCYTOSIS

(71) Applicant: CASE WESTERN RESERVE UNIVERSITY, Cleveland, OH (US)

(72) Inventors: Anirban Sen Gupta, Cleveland, OH (US); Ujjal Didar Singh Sekhon, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 373 days.

(21) Appl. No.: 18/276,340

(22) PCT Filed: Feb. 9, 2022

(86) PCT No.: PCT/US2022/015776
§ 371 (c)(1),
(2) Date: Aug. 8, 2023

(87) PCT Pub. No.: WO2022/173798
PCT Pub. Date: Aug. 18, 2022

(65) Prior Publication Data

US 2024/0108748 A1 Apr. 4, 2024

Related U.S. Application Data

(60) Provisional application No. 63/147,411, filed on Feb. 9, 2021.

(51) Int. Cl.
*A61K 47/69* (2017.01)
*A61K 47/65* (2017.01)

(52) U.S. Cl.
CPC .......... *A61K 47/6911* (2017.08); *A61K 47/65* (2017.08)

(58) Field of Classification Search
CPC .......... A61K 47/6911
See application file for complete search history.

(56) References Cited

U.S. PATENT DOCUMENTS 8,734,774 B2 5/2014 Frelinger et al.
9,107,845 B2 8/2015 Gupta et al.
(Continued)

FOREIGN PATENT DOCUMENTS

WO 2008/073856 A2 6/2008
WO 2018/204392 A1 11/2018

OTHER PUBLICATIONS

Naeini, Mehri Bemani, "The Role of Phosphatidylserine recognition receptors in multiple biological functions", Cellular and Molecular Biology Letters 2020, 25:23, pp. 1-17.
(Continued)

*Primary Examiner* — Benjamin J Packard
(74) *Attorney, Agent, or Firm* — Tarolli, Sundheim, Covell & Tummino LLP

(57) ABSTRACT

A nanoparticle and/or microparticle construct for therapeutic applications includes a plurality of targeting moieties that bind to target molecules of a cell, tissue, and/or disease site in a subject, phosphatidylserine phospholipids, and releasable cloaking agents configured to mask the phosphatidylserine phospholipids prior to binding of the target moieties to the target molecules and be released from the construct to expose the phosphatidylserine phospholipids upon binding of the target moieties to the target molecules.

21 Claims, 36 Drawing Sheets

Specification includes a Sequence Listing.

(56) References Cited

U.S. PATENT DOCUMENTS

| | | | | |
|---|---|---|---|---|
| 9,107,963 | B2 | 8/2015 | Sen Gupta et al. | |
| 10,426,820 | B2 | 10/2019 | Sen Gupta et al. | |
| 10,716,865 | B2 | 7/2020 | Sen Gupta et al. | |
| 2013/0089516 | A1* | 4/2013 | Frelinger ............... | C07K 14/55 536/23.5 |
| 2019/0054151 | A1* | 2/2019 | Sen Gupta ........... | A61K 38/185 |

OTHER PUBLICATIONS

European Application No. 22753243.9, Extended Search Report dated Sep. 9, 2025.

* cited by examiner

A

Cholesterol KTFKC-PEG synthesis

STEP 2

Cholesterol-TEG-Azide

Alk-KTFKC-PEG

Cholesterol-KTFKC-PEG

A
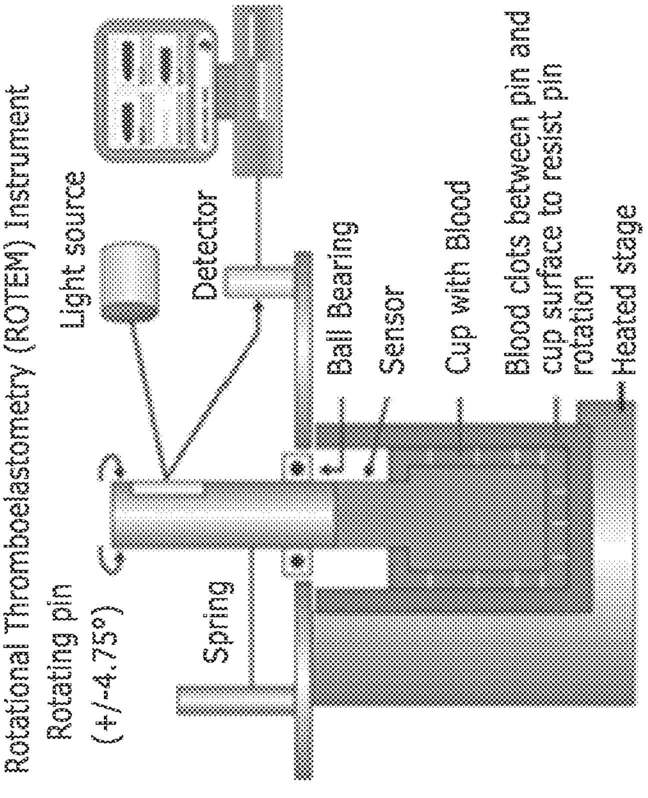
Fig. 14A-C

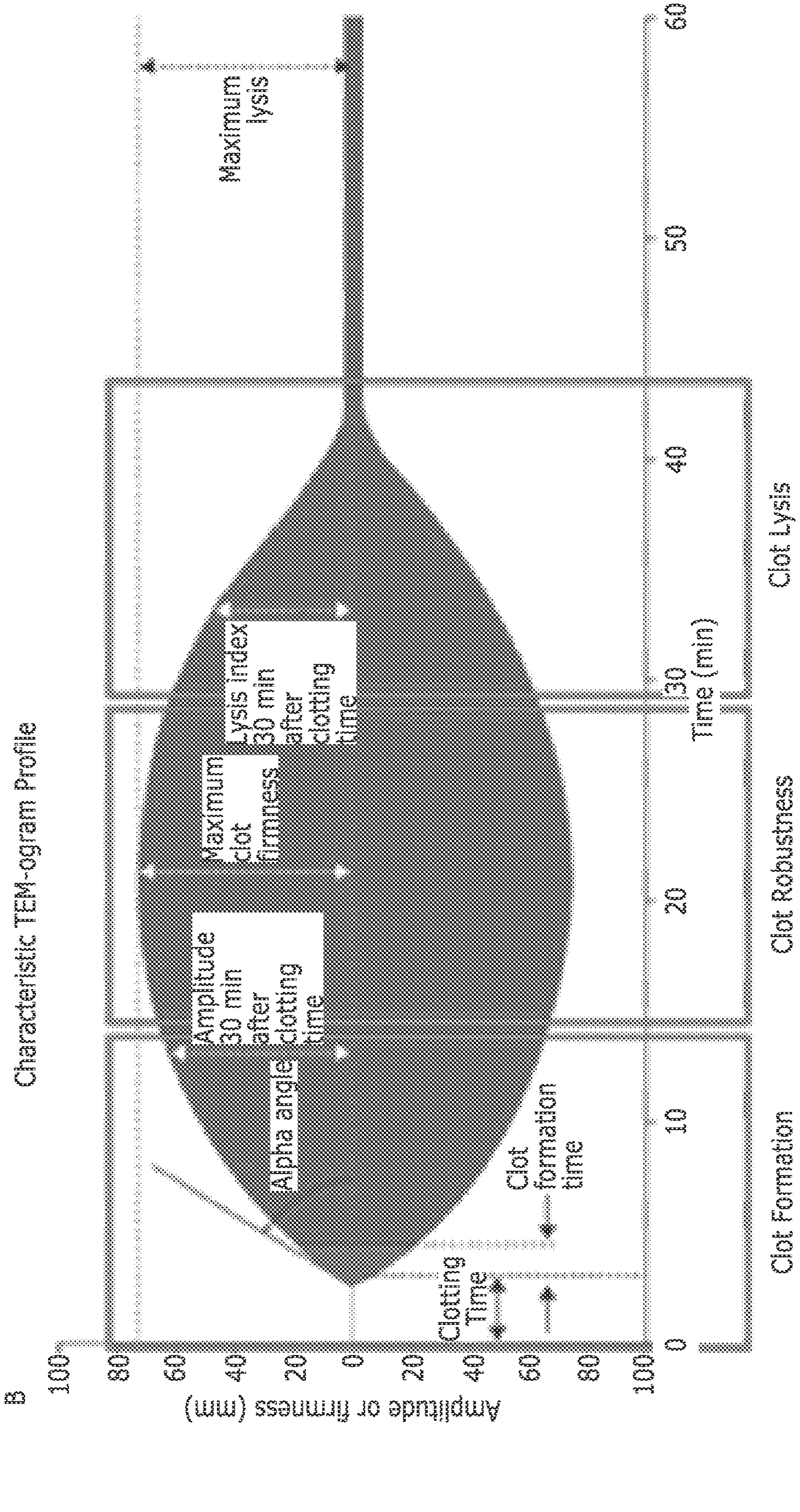
Fig. 14A-C

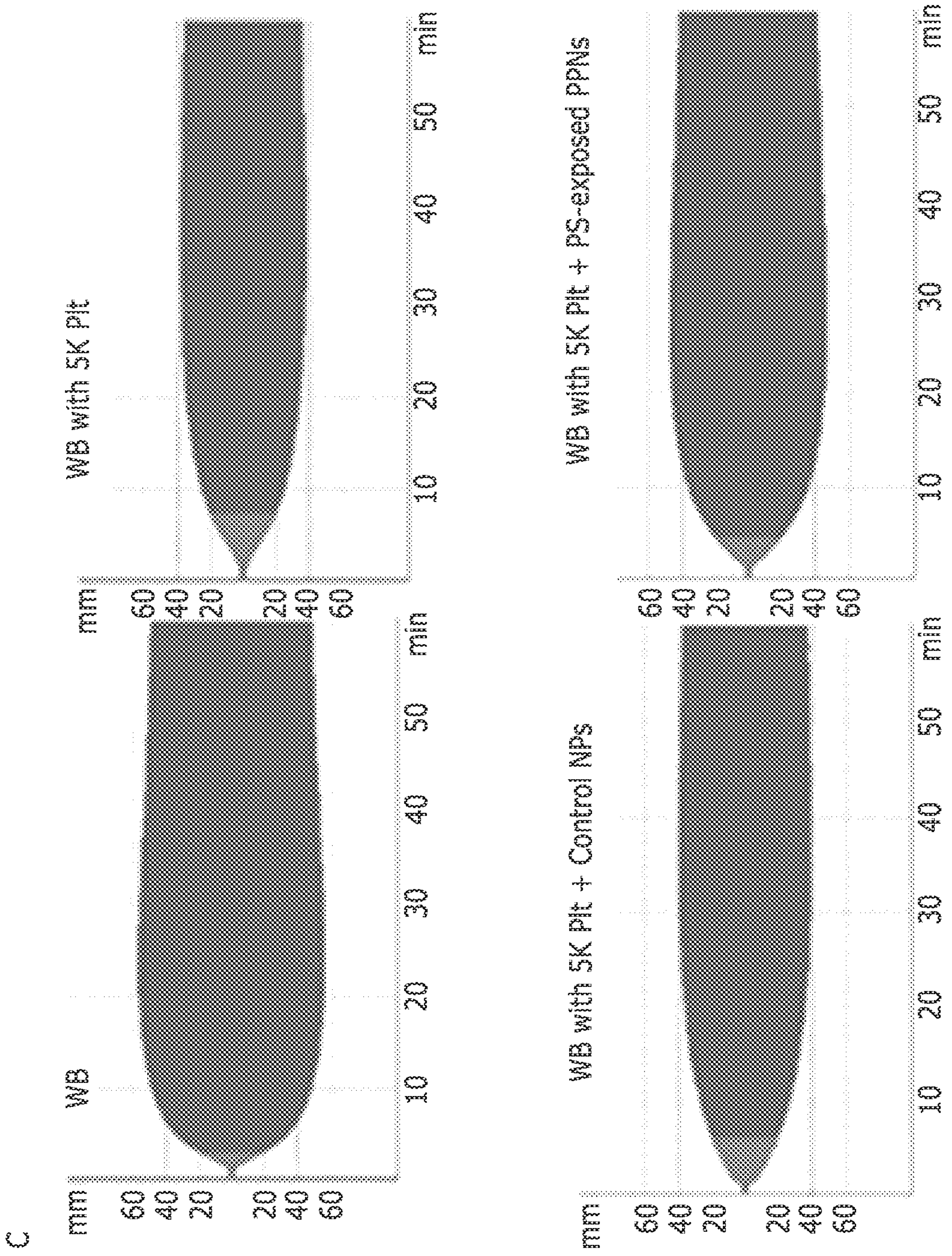
Fig. 14A-C

Assuming Platelets and PPNs to be spherical particle systems:

Surface area:
$4\Pi r^2 = 4\Pi\ (2000\ nm)^2$

Surface area:
$4\Pi r^2 = 4\Pi\ (200\ nm)^2$

Based on surface area, 1 Platelet = 100 PPN nanoparticles

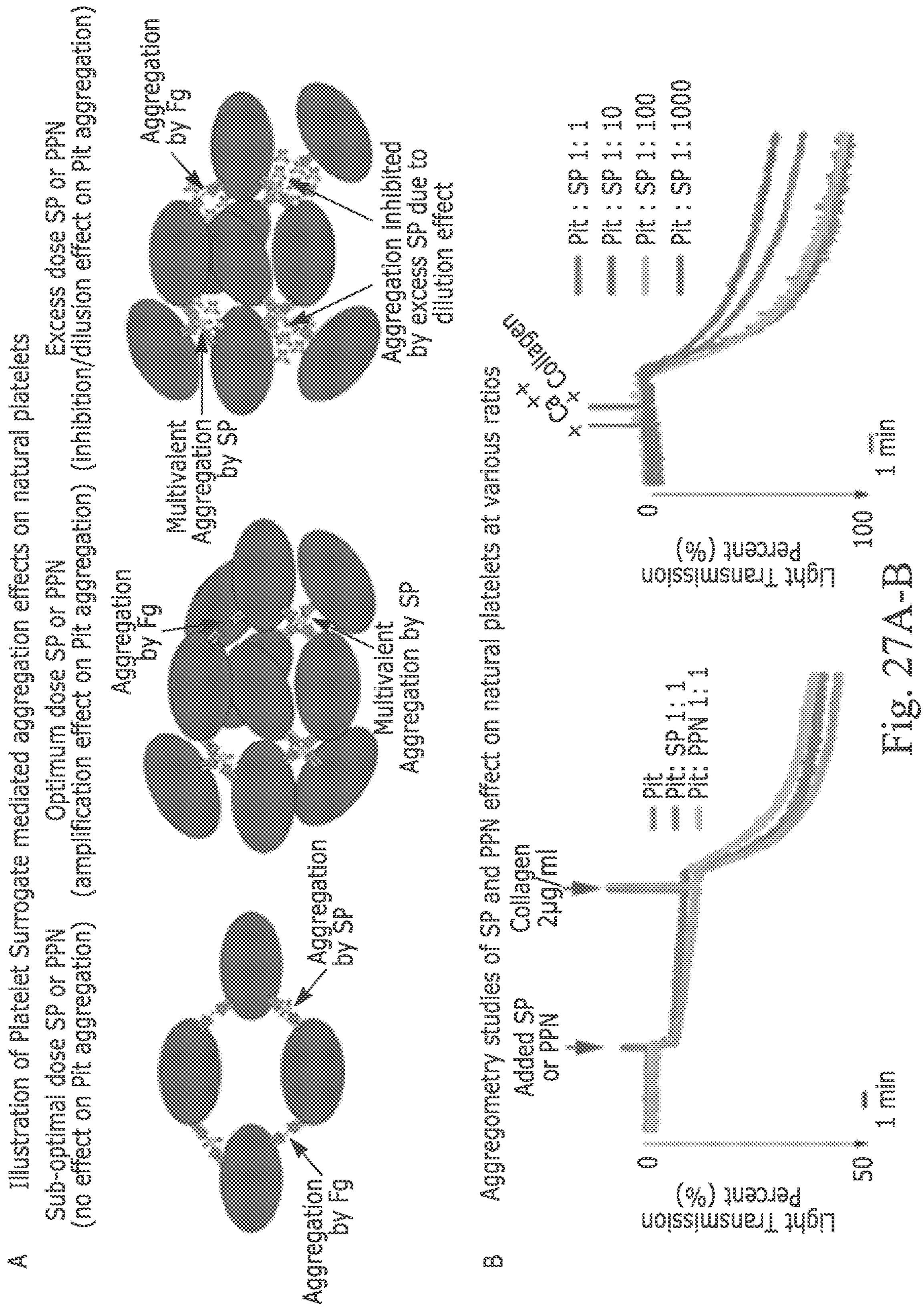
Fig. 27A-B

SEQUENCE LISTING

```
<160> NUMBER OF SEQ ID NOS: 7

<210> SEQ ID NO 1
<211> LENGTH: 15
<212> TYPE: PRT
<213> ORGANISM: Homo sapiens

<400> SEQUENCE: 1

Thr Arg Tyr Leu Arg Ile His Pro Gln Ser Trp Val His Gln Ile
1               5                   10                  15


<210> SEQ ID NO 2
<211> LENGTH: 21
<212> TYPE: PRT
```

<213> ORGANISM: Homo sapiens
<220> FEATURE:
<221> NAME/KEY: MISC_FEATURE
<222> LOCATION: (3)..(3)
<223> OTHER INFORMATION: 4HYP 4-Hydroxyproline
<220> FEATURE:
<221> NAME/KEY: MISC_FEATURE
<222> LOCATION: (6)..(6)
<223> OTHER INFORMATION: 4HYP 4-Hydroxyproline
<220> FEATURE:
<221> NAME/KEY: MISC_FEATURE
<222> LOCATION: (9)..(9)
<223> OTHER INFORMATION: 4HYP 4-Hydroxyproline
<220> FEATURE:
<221> NAME/KEY: MISC_FEATURE
<222> LOCATION: (12)..(12)
<223> OTHER INFORMATION: 4HYP 4-Hydroxyproline
<220> FEATURE:
<221> NAME/KEY: MISC_FEATURE
<222> LOCATION: (15)..(15)
<223> OTHER INFORMATION: 4HYP 4-Hydroxyproline
<220> FEATURE:
<221> NAME/KEY: MISC_FEATURE
<222> LOCATION: (18)..(18)
<223> OTHER INFORMATION: 4HYP 4-Hydroxyproline
<220> FEATURE:
<221> NAME/KEY: MISC_FEATURE
<222> LOCATION: (21)..(21)
<223> OTHER INFORMATION: 4HYP 4-Hydroxyproline

<400> SEQUENCE: 2

```
Gly Pro Xaa Gly Pro Xaa Gly Pro Xaa Gly Pro Xaa Gly Pro Xaa Gly
1               5                   10                  15

Pro Xaa Gly Pro Xaa
            20
```

<210> SEQ ID NO 3
<211> LENGTH: 9
<212> TYPE: PRT
<213> ORGANISM: Homo sapiens

<400> SEQUENCE: 3

```
Cys Asn Pro Arg Gly Asp Tyr Arg Cys
1               5
```

<210> SEQ ID NO 4
<211> LENGTH: 5
<212> TYPE: PRT
<213> ORGANISM: Homo sapiens

<400> SEQUENCE: 4

```
Lys Thr Phe Lys Cys
1               5
```

<210> SEQ ID NO 5
<211> LENGTH: 8
<212> TYPE: PRT
<213> ORGANISM: Homo sapiens

<400> SEQUENCE: 5

```
Val Pro Leu Ser Leu Tyr Ser Gly
1               5
```

<210> SEQ ID NO 6
<211> LENGTH: 16
<212> TYPE: PRT
<213> ORGANISM: Homo sapiens

-continued

```
<400> SEQUENCE: 6

Cys Thr Arg Tyr Leu Arg Ile His Pro Gln Ser Trp Val His Gln Ile
1               5                   10                  15


<210> SEQ ID NO 7
<211> LENGTH: 22
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: 4HYP 4-Hydroxyproline
<220> FEATURE:
<221> NAME/KEY: MOD_RES
<222> LOCATION: (7)..(7)
<223> OTHER INFORMATION: 4HYP 4-Hydroxyproline
<220> FEATURE:
<221> NAME/KEY: MOD_RES
<222> LOCATION: (10)..(10)
<223> OTHER INFORMATION: 4HYP 4-Hydroxyproline
<220> FEATURE:
<221> NAME/KEY: MOD_RES
<222> LOCATION: (13)..(13)
<223> OTHER INFORMATION: 4HYP 4-Hydroxyproline
<220> FEATURE:
<221> NAME/KEY: MOD_RES
<222> LOCATION: (16)..(16)
<223> OTHER INFORMATION: 4HYP 4-Hydroxyproline
<220> FEATURE:
<221> NAME/KEY: MOD_RES
<222> LOCATION: (19)..(19)
<223> OTHER INFORMATION: 4HYP 4-Hydroxyproline
<220> FEATURE:
<221> NAME/KEY: MOD_RES
<222> LOCATION: (22)..(22)
<223> OTHER INFORMATION: 4HYP 4-Hydroxyproline

<400> SEQUENCE: 7

Cys Gly Pro Xaa Gly Pro Xaa Gly Pro Xaa Gly Pro Xaa Gly Pro Xaa
1               5                   10                  15

Gly Pro Xaa Gly Pro Xaa
            20
```

COMPOSITIONS AND METHODS FOR TARGETED AMPLIFICATION OF COAGULATION AND PHAGOCYTOSIS

RELATED APPLICATION

This application claims priority from U.S. Provisional Application No. 63/147,411, filed Feb. 9, 2021, the subject matter of which is incorporated herein by reference in its entirety.

GOVERNMENT FUNDING

This invention was made with government support under HL098217 and HL121212 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 9, 2022, is named CWR029716WOORDSEQUENCELISTING and is 2,747 bytes in size.

BACKGROUND

There are many challenges facing platelet transfusions including platelet availability, portability, contamination risks and a very short shelf-life. Pathogen reduction, low temperature storage and stem cell-based in vitro platelet production are currently being studied to address these challenges. However, synthetic platelet surrogates provide another translationally feasible alternative. Most synthetic platelet surrogate designs have involved coating nanoparticles with fibrinogen or fibrinogen-derived peptides to amplify platelet aggregation. However, the hemostatic response of platelets requires critical steps including rapid adhesion to vWF and collagen at the injury site, followed by aggregation and procoagulant activity at that site. The fibrinogen (and fibrinogen-derived peptide)-coated nanoparticles do not have both adhesion and aggregation capabilities.

SUMMARY

Embodiments described herein relate to compositions and methods for targeted amplification of coagulation and macrophage phagocytosis, and particularly relates to bioresponsive nanoparticles and/or microparticles that include phosphatidylserine phospholipids and to their use in treating a vascular injury and/or that promoting macrophage phagocytosis of targeted cells (e.g., cancer cells) or pathogens in a subject in need thereof.

The cell membrane is made up of predominantly four types of phospholipids, namely phosphatidylcholine (PC), phosphatidylethanolamine (PE), phosphatidylserine (PS) and sphingomyelin. Of these, PC, PE and sphingomyelin are zwitterionic (and thus overall neutral), while PS is anionic. In normal live healthy cells, PS is predominantly present in the inner leaflet of the bilayer cell membrane. When cells undergo apoptosis, action of translocase enzymes transport PS to the outer leaflet of the cell membrane, such that the cell surface becomes PS-rich and anionic. For many cells, this PS-rich apoptotic signal results in an 'eat me' signal to the macrophages. Therefore, presentation of PS-rich surface on nanoparticles and/or microparticles binding to specific cells can provide a way to artificially trigger a macrophagic response at a disease site, thereby rendering a 'triggered' inflammatory or immune response that can have potential therapeutic effects in diseases like cancer and/or pathogen infection.

Another interesting area of PS exposure on cells is in the context of platelets. Circulating 'resting' platelets do not have a PS-rich surface, but once platelets localize to an injury site and become activated to promote clotting, the activated platelets expose PS on their surface. This PS becomes the nidus of coagulation factor co-localization and assembly, which in the presence of calcium (Ca++) leads to formation of the tenase complex and subsequently the prothrombinase complex, resulting in amplification of thrombin generation. This thrombin then converts soluble fibrinogen to insoluble fibrin that becomes self-assembled as well as crosslinked to form the hemostatic clot. Therefore, exposure of PS on nanoparticle and/or microparticle systems localizing at an injury site can provide a way to mimic and amplify natural platelets' procoagulant mechanism of thrombin amplification, and render high hemostatic outputs in treating bleeding. This can be an efficient way to manage bleeding complications in patients that have disease-induced, drug-induced, or trauma-induced platelet dysfunctions.

In both cases described above, the exposure of PS on the PS-incorporated nanoparticles and/or microparticles should be 'target-specific' and 'stimulus-responsive', such that the PS is not exposed on the nanoparticles and/or microparticles in systemic circulation, so as to avoid rapid macrophagic clearance or systemic procoagulant risks. For this, the nanoparticle and/or microparticle surface can be covered (masked) with a releasable cloaking agent that can be cleaved off at the disease site to expose the PS and trigger a target site-specific macrophagic or procoagulant response.

Accordingly, in some embodiments a composition for targeted amplification of coagulation or phagocytosis can include a plurality of nanoparticle and/or microparticle constructs. Each construct can have an outer portion that defines an outer surface of the construct, a plurality of targeting moieties and releasable cloaking agents that are linked to the outer portion and extend from the outer surface, and a plurality of phosphatidylserine phospholipids that extend from and/or define portions of the outer portion. The targeting moieties are configured to specifically bind to target molecules of a cell, tissue, and/or disease site in a subject. The releasable cloaking agents are configured to mask the phosphatidylserine phospholipids prior to binding of the target moieties to the target molecules and be released from the construct to expose the phosphatidylserine phospholipids upon binding of the target moieties to the target molecules.

In some embodiments, upon systemic administration of the composition to the subject and prior to binding of the target moieties to the target molecules, the cloaking agents inhibit exposure of the phosphatidylserine phospholipids so as to avoid macrophage clearance or systemic procoagulant risk. In other embodiments, upon binding of the target moieties to the target molecules of the cell, tissue, and/or disease site in the subject, exposed phosphatidylserine phospholipids promote macrophage engulfment and/or a procoagulant response.

In some embodiments, the cloaking agent includes a hydrophilic polymer that is releasably linked to the outer portion of the construct. The hydrophilic polymer can include, for example, polyethylene glycol.

In some embodiments, the cloaking agent is releasably linked to an outer portion of the construct with an enzyme cleavable linker. The enzyme cleavable linker can be cleaved by an enzyme that is substantially unique or specific to the target cells, tissue, and/or disease site and/or has a higher concentration or activity compared to the concentration or activity at other cells, tissues, and/or disease sites in the subject. The enzyme can include, for example, at least one of a matrix metalloprotease, plasmin, or thrombin. The enzyme cleavable linker can include at least one of a valine-citrulline linker, such as a glutamic acid-valine-citrulline linker, KTFKC (SEQ ID NO: 4), or VPLSLYSG (SEQ ID NO: 5).

In some embodiments, the nanoparticle and/or microparticle construct can have a diameter of about 50 nm to about 5 μm, preferably about 50 nm to about 200 nm, or more preferably about 100 nm to about 150 nm.

In some embodiments, the nanoparticle and/or microparticle constructs can be liposomes. The liposomes can include a plurality of phospholipids and optionally cholesterol to define a lipid membrane. The phospholipids can include distearoylphosphatidylserine (DSPS) and at least one of distearoylphosphatidylcholine (DSPC), dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In some embodiments, the distearoylphosphatidylserine (DSPS) can include about 1 mole % to about 20 mole %, about 5 mole % to about 15 mole %, or about 10 mole % to about 15 mole % of the lipid membrane.

In some embodiments, the targeting moieties can include a plurality of peptides. The peptides can include a plurality of von Willebrand factor-binding peptides (VBPs), collagen-binding peptides (CBPs) and fibrinogen mimetic peptides (FMPs).

In some embodiments, the VBPs, CBPs, and FMPs can be spatially or topographically arranged on the outer surface such that the VBPs, CBPs, and FMPs do not spatially mask each other and the construct is able to adhere to a vascular surface, vascular disease site, and/or vascular injury site with exposed vWF and collagen and promote arrest and aggregation of active platelets onto sites of the construct adhesion.

In some embodiments, the VBPs, CBPs, and FMPs are conjugated to the outer surface with PEG linkers.

In other embodiments, the nanoparticle and/or microparticle construct can have a shape, size and elastic modulus that facilitates margination to a vascular wall upon administration to vasculature of a subject.

In some embodiments, the VBPs can have an amino acid sequence of SEQ ID NO: 1, the CBPs can have an amino acid sequence of SEQ ID NO: 2, and the FMPs can have an amino acid sequence of SEQ ID NO: 3. The ratio of VPBs to CPBs provided on the outer surface can be about 70:30 to about 30:70. The ratio of VPB:CPB:FMP is about 1:1:2 to 1:2:1 to 2:1:1.

In other embodiments, the targeting moiety can bind a cancer cell surface molecule of a cancer cell. The cancer cell surface molecule can be a cancer cell antigen on the surface of a cancer cell. Examples of cancer cell antigens can include at least one of 5T4, α2β1 integrin, AXL receptor tyrosine kinase (AXL), B-cell maturation antigen (BCMA), c-MET (Hepatocyte Growth Factor Receptor), C4.4a, carbonic anhydrase 6 (CA6), carbonic anhydrase 9 (CA9), Cadherin-6, CD19, CD22, CD25, CD27L, CD30, CD33, CD37, CD44v6, CD56, CD70, CD74, CD79b, CD123, CD138, carcinoembryonic antigen (CEA), cKit, collagen receptor, Cripto protein, CS1, delta-like canonical Notch ligand 3 (DLL3), endothelin receptor type B (EDNRB), ephrin A4 (EFNA4), epidermal growth factor receptor (EGFR), EGFRvIll, ectonucleotide pyrophosphatase/phosphodiesterase 3 (ENPP3), EPH receptor A2 (EPHA2), fibroblast growth factor receptor 2 (FGFR2), fibroblast growth factor receptor 3 (FGFR3), FMS-like tyrosine kinase 3 (FLT3), folate receptor 1 (FOLR1), glycoprotein non-metastatic B (GPNMB), guanylate cyclase 2 C (GUCY2C), human epidermal growth factor receptor 2 (HER2), human epidermal growth factor receptor 3 (HER3), Integrin alpha, lysosomal-associated membrane protein 1 (LAMP-1), Lewis Y, LIV-1, leucine rich repeat containing 15 (LRRC15), mesothelin (MSLN), mucin 1 (MUC1), mucin 16 (MUC16), sodium-dependent phosphate transport protein 2B (NaPi2b), Nectin-4, NMB, NOTCH3, p-cadherin (p-CAD), prostate-specific membrane antigen (PSMA), protein tyrosine kinase 7 (PTK7), protein tyrosine phosphatase mu (PTPmu) solute carrier family 44 member 4 (SLC44A4), SLIT like family member 6 (SLITRK6), STEAP family member 1 (STEAP1), tissue factor (TF), T cell immunoglobulin and mucin protein-1 (TIM-1), or trophoblast cell-surface antigen (TROP-2).

In some embodiments, the constructs can further include a therapeutic agent and/or an imaging agent conjugated to or defining at least a portion of the construct.

In still other embodiments, the construct can include a plurality of Gold Nanorods (GNRs) conjugated to the outer surface. The GNRs can allow photothermal destabilization of the nanoparticle construct and release of the therapeutic and/or imaging agent in response to near-infrared (NIR) light.

Other embodiments described herein relate to a platelet-mimicking procoagulant nanoparticles (PPNs). The PPNs can include a biocompatible flexible nanoparticle that includes an outer portion that defines an outer surface of the nanoparticle, a plurality of targeting moieties and releasable cloaking agents that are linked to the outer portion and extend from the outer surface, and a plurality of phosphatidylserine phospholipids that extend from and/or define portions of the outer portion. The targeting moieties can include a plurality of von Willebrand factor-binding peptides (VBPs), collagen-binding peptides (CBPs), and/or fibrinogen mimetic peptides (FMPs). The releasable cloaking agents can be configured to mask the phosphatidylserine phospholipids prior to binding of the target moieties to von Willebrand factor, collagen, and/or GPIIb-IIIa and be released from the nanoparticle to expose the phosphatidylserine phospholipids upon binding of the target moieties to von Willebrand factor, collagen, and/or GPIIb-IIIa.

In some embodiments, upon systemic administration of the PPNs to the subject and prior to binding of the target moieties to the von Willebrand factor, collagen, and/or GPIIb-IIIa, the cloaking agents inhibit exposure of the phosphatidylserine phospholipids so as to avoid systemic procoagulant risk. In other embodiments, upon binding of the target moieties to von Willebrand factor, collagen, and/or GPIIb-IIIa, exposed phosphatidylserine phospholipids can promote a procoagulant response at a site of the PPNs binding.

In some embodiments, the cloaking agent includes a hydrophilic polymer that is releasably linked to the outer portion of the construct. The hydrophilic polymer can include, for example, polyethylene glycol.

In some embodiments, the cloaking agent is releasably linked to an outer portion of the nanoparticle with an enzyme cleavable linker. The enzyme cleavable linker can be cleaved by an enzyme that is substantially unique or specific to a vascular injury site and/or has a higher concentration or activity compared to concentration or activity at other cells, tissues, and/or disease sites in the subject. The enzyme can include at least one of a plasmin or thrombin, and the enzyme cleavable linker can include a peptide having the amino acid sequence of KTFKC (SEQ ID NO: 4).

In some embodiments, the PPN can have a diameter of about 50 nm to about 5 μm, preferably about 50 nm to about 200 nm, or more preferably about 100 nm to about 150 nm.

In some embodiments, the PPN can be a liposome. The liposome can include a plurality of phospholipids and optionally cholesterol to define a lipid membrane. The phospholipids can include distearoylphosphatidylserine (DSPS) and at least one of distearoylphosphatidylcholine (DSPC), dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In some embodiments, the distearoylphosphatidylserine (DSPS) can include about 1 mole % to about 20 mole %, about 5 mole % to about 15 mole %, or about 10 mole % to about 15 mole % of the lipid membrane.

In some embodiments, the VBPs, CBPs, and FMPs can be spatially or topographically arranged on the outer surface such that the VBPs, CBPs, and FMPs do not spatially mask each other and the PPN is able to adhere to a vascular surface, vascular disease site, and/or vascular injury site with exposed vWF and collagen and promote arrest and aggregation of active platelets onto sites of the construct adhesion.

In some embodiments, the VBPs, CBPs, and FMPs are conjugated to the outer surface with PEG linkers.

In other embodiments, the PPNs can have a shape, size and elastic modulus that facilitates margination to a vascular wall and their bio-interactions upon administration to a vasculature of a subject.

In some embodiments, the VBPs can have an amino acid sequence of SEQ ID NO: 1, the CBPs can have an amino acid sequence of SEQ ID NO: 2, and the FMPs can have an amino acid sequence of SEQ ID NO: 3. The ratio of VPBs to CPBs provided on the outer surface can be about 70:30 to about 30:70. The ratio of VPB:CPB:FMP is about 1:1:2 to 1:2:1 to 2:1:1.

In some embodiments, the PPN can be administered to a site with exposed vWF and collagen to promote aggregation of activated platelets.

In other embodiments, the PPN can be administered to a site of vascular injury in a subject in need thereof to diminish bleeding in the subject.

In still other embodiments, the PPN can be administered to a site of vascular injury in a subject to treat the vascular injury.

Other embodiments described herein relate to a composition for inducing a macrophage response to a cell and/or pathogen. The composition can include a plurality nanoparticle and/or microparticle constructs. Each construct can have an outer portion that defines an outer surface of the construct, a plurality of targeting moieties and releasable cloaking agents that are linked to the outer portion and extend from the outer surface, and a plurality of phosphatidylserine phospholipids that extend from and/or define portions of the outer portion. The targeting moieties are configured to specifically bind to target molecules of a cancer cell or pathogen in a subject. The releasable cloaking agents are configured to mask the phosphatidylserine phospholipids prior to binding of the target moieties to the cancer cell or pathogen and be released from the construct to expose the phosphatidylserine phospholipids upon binding of the target moieties to the cancer cell or pathogen.

In some embodiments, upon systemic administration of the composition to the subject and prior to binding of the target moieties to the cancer cells or pathogens, the cloaking agents inhibit exposure of the phosphatidylserine phospholipids so as to avoid macrophage clearance of the constructs. In other embodiments, upon binding of the target moieties to the cancer cells or pathogen in the subject, exposed phosphatidylserine phospholipids promote macrophage engulfment cancer cells or pathogen.

In some embodiments, the cloaking agent includes a hydrophilic polymer that is releasably linked to the outer portion of the construct. The hydrophilic polymer can include, for example, polyethylene glycol.

In some embodiments, the cloaking agent is releasably linked to an outer portion of the construct with an enzyme cleavable linker. The enzyme cleavable linker can be cleaved by an enzyme that is substantially unique or specific to the cancer cells or pathogen and/or has a higher concentration or activity compared to other cells, tissues, and/or disease sites in the subject. The enzyme can include a matrix metalloprotease and the enzyme cleavable linker comprises a peptide having an amino acid sequence of VPLSLYSG (SEQ ID NO: 2).

In some embodiments, the nanoparticle and/or microparticle construct can have a diameter of about 50 nm to about 5 μm, preferably about 50 nm to about 200 nm, or more preferably about 100 nm to about 150 nm.

In some embodiments, the nanoparticle and/or microparticle construct can be liposomes. The liposomes can include a plurality of phospholipids and optionally cholesterol to define a lipid membrane. The phospholipids can include distearoylphosphatidylserine (DSPS) and at least one of distearoylphosphatidylcholine (DSPC), dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In some embodiments, the distearoylphosphatidylserine (DSPS) can include about 1 mole % to about 20 mole %, about 5 mole % to about 15 mole %, or about 10 mole % to about 15 mole % of the lipid membrane.

In some embodiments, the targeting moiety can bind a cancer cell surface molecule. The cancer cell surface molecule can include a cancer cell antigen on the surface of a cancer cell. For example, the cancer cell antigen can include at least one of 5T4, α2β1 integrin, AXL receptor tyrosine kinase (AXL), B-cell maturation antigen (BCMA), c-MET (Hepatocyte Growth Factor Receptor), C4.4a, carbonic anhydrase 6 (CA6), carbonic anhydrase 9 (CA9), Cadherin-6, CD19, CD22, CD25, CD27L, CD30, CD33, CD37, CD44v6, CD56, CD70, CD74, CD79b, CD123, CD138, carcinoembryonic antigen (CEA), cKit, collagen receptor, Cripto protein, CS1, delta-like canonical Notch ligand 3 (DLL3), endothelin receptor type B (EDNRB), ephrin A4 (EFNA4), epidermal growth factor receptor (EGFR), EGFRvIII, ectonucleotide pyrophosphatase/phosphodiesterase 3 (ENPP3), EPH receptor A2 (EPHA2), fibroblast growth factor receptor 2 (FGFR2), fibroblast growth factor receptor 3 (FGFR3), FMS-like tyrosine kinase 3 (FLT3), folate receptor 1 (FOLR1), glycoprotein non-metastatic B (GPNMB), guanylate cyclase 2 C (GUCY2C), human epidermal growth factor receptor 2 (HER2), human epidermal growth factor receptor 3 (HER3), Integrin alpha, lysosomal-associated membrane protein 1 (LAMP-1), Lewis Y, LIV-1, leucine rich repeat containing 15 (LRRC15), mesothelin (MSLN), mucin 1 (MUC1), mucin 16 (MUC16), sodium-dependent phosphate transport protein 2B (NaPi2b), Nectin-4, NMB, NOTCH3, p-cadherin (p-CAD), prostate-specific membrane antigen (PSMA), protein tyrosine kinase 7 (PTK7), protein tyrosine phosphatase mu (PTPmu) solute carrier family 44 member 4 (SLC44A4), SLIT like family member 6 (SLITRK6), STEAP family member 1 (STEAP1), tissue factor (TF), T cell immunoglobulin and mucin protein-1 (TIM-1), or trophoblast cell-surface antigen (TROP-2).

In some embodiments, the constructs can further include a therapeutic agent and/or an imaging agent conjugated to or defining at least a portion of the construct.

In some embodiments, the therapeutic agent can further include at least one chemotherapeutic agent, anti-proliferative agent, biocidal agent, biostatic agent, or anti-microbial agent.

In other embodiments, the construct can further include a plurality of Gold Nanorods (GNRs) conjugated to the outer surface, the GNRs allowing photothermal destabilization of the nanoparticle construct and release of the therapeutic and/or imaging agent in response to near-infrared (NIR) light.

In some embodiments, the composition can be administered to a subject in need thereof to treat cancer and/or pathogen infection in the subject.

BRIEF DESCRIPTION OF THE DRAWINGS

FIGS. 14(A-C) illustrate A: ROTEM instrument set-up; B: Characteristic TEM-ogram showing various regions corresponding to clot formation, clot robustness (stability) and clot lysis; C: Representative TEM-ograms of platelet-depleted whole blood (WB with 5K Plt) treated with control nanoparticles (Control NPs) or PS-exposed PPNs.

FIGS. 27(A-B) illustrates A. Schematic representation of particle-to-platelet interactions at low, optimum and excessive particle concentration; B. Aggregometry studies with collagen-activated platelets (Plt) confirm that, without platelet activation (prior to collagen addition) the original platelet surrogate particles (SynthoPlate, SP) or PPNs do not themselves activate and aggregate platelets (aggregation signal remains at baseline); After collagen addition, neither SP nor PPN can enhance platelet aggregation at Plt:particle ratio of 1:1; Upon increasing Plt:particle ratio to 1:10 the platelet aggregation is enhanced possibly via multivalent interactions of particles with platelets and this enhancement is maintained when Plt:particle ratio is increased to 1:100; However, at platelet: particle ratio of 1:1000 the aggregation is reduced possibly due to crowding and dilution effect particles around platelets. Note that the platelet aggregating mechanism of SP and PPN is the same (FMP peptide mediated binding of the nanoparticles to platelet integrin $\alpha_{IIb}\beta_3$).

DETAILED DESCRIPTION

Figure 1:
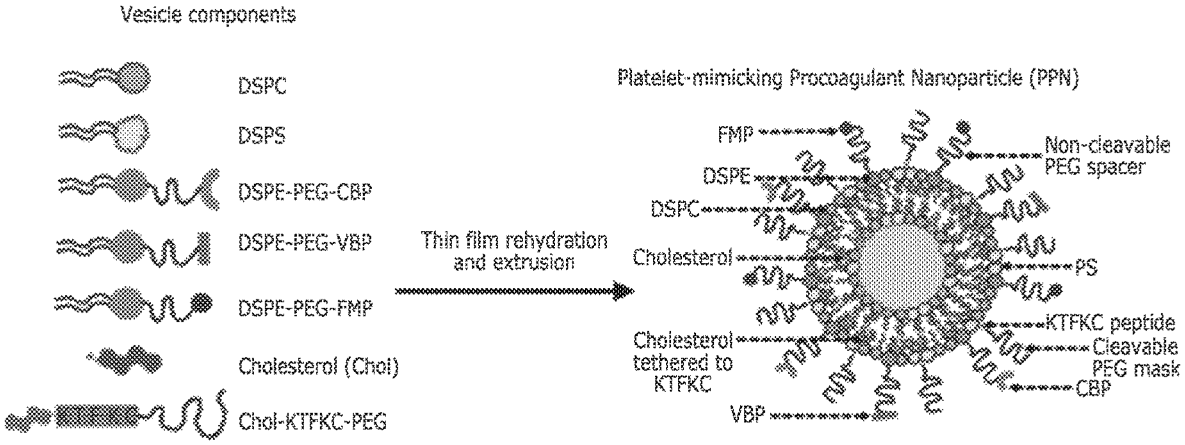
FIG. 1 illustrates membrane compositional elements for manufacturing PPNs; The VBP, CBP and FMP peptides are vWF-binding, collagen-binding and fibrinogen-mimetic peptides that integratively mimic the adhesion and aggregation mechanisms of platelets; The DSPS component allows incorporation of phosphatidylserine (PS) in the PPN membrane; The Cholesterol-KTFKC (SEQ ID NO: 4)-PEG component allows incorporation of a plasmin-cleavable cloak to mask the PS on PPN surface.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, aves, etc.).

The terms "diminishing," "reducing," or "preventing," "inhibiting," and variations of these terms, as used herein include any measurable decrease, including complete or substantially complete inhibition. The terms "enhance" or "enhanced" as used herein include any measurable increase or intensification.

As used herein, the term "small molecule" can refer to lipids, carbohydrates, polynucleotides, polypeptides, or any other organic or inorganic molecules.

As used herein, the term "polypeptide" refers to a polymer composed of amino acid residues related naturally occurring structural variants, and synthetic non-naturally occurring analogs thereof linked via peptide bonds or modified peptide bonds (i.e., peptide isosteres), related naturally occurring structural variants, and synthetic non-naturally occurring analogs thereof, glycosylated polypeptides, and all "mimetic" and "peptidomimetic" polypeptide forms. Synthetic polypeptides can be synthesized, for example, using an automated polypeptide synthesizer. The term can refer to an oligopeptide, peptide, polypeptide, or protein sequence, or to a fragment, portion, or subunit of any of these. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "portion" of a polypeptide means at least about three sequential amino acid residues of the polypeptide. It is understood that a portion of a polypeptide may include every amino acid residue of the polypeptide.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

As used herein, the term "imaging agent" can refer to a biological or chemical moiety capable of be encapsulated by a nanoparticle or microparticle construct of the application and that may be used to detect, image, and/or monitor the presence and/or progression of a cell cycle, cell function/physiology, condition, pathological disorder and/or disease.

As used herein, the term "targeting moiety" can refer to a molecule or molecules that are able to bind to and complex with a biomarker. The term can also refer to a functional group that serves to target or direct a therapeutic agent to a particular location, cell type, diseased tissue, or association. In general, a "targeting moiety" can be directed against a biomarker.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. "Therapeutic agents" can include any agent (e.g., molecule, drug, pharmaceutical composition, etc.) capable of be encapsulated by or conjugated to a nanoparticle or microparticle construct of the application and further capable of preventing, inhibiting, or arresting the symptoms and/or progression of a disease.

"Nanoparticle" or "microparticle" as used herein is meant to include particles, spheres, capsules, and other structures having a length or diameter of about 10 nm to about 100 μm. For the purposes of this application, the terms "nanosphere", "nanoparticle", "nanoparticle construct", "nanovehicle", "nanocapsule", "microsphere", "microparticle", and "microcapsule" are used interchangeably.

The term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

The term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

The term "tumor" can refer to an abnormal mass or population of cells that result from excessive cell division, whether malignant or benign, and all pre-cancerous and cancerous cells and tissues.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

Embodiments described herein relate to compositions and methods for targeted amplification of coagulation and macrophage phagocytosis, and particularly relates to bioresponsive nanoparticles and/or microparticles that include phosphatidylserine phospholipids and to their use in treating a vascular injury and/or that promoting macrophage phagocytosis of targeted cells (e.g., cancer cells) or pathogens in a subject in need thereof.

The cell membrane is made up of predominantly four types of phospholipids, namely phosphatidylcholine (PC), phosphatidylethanolamine (PE), phosphatidylserine (PS) and sphingomyelin. Of these, PC, PE and sphingomyelin are zwitterionic (and thus overall neutral), while PS is anionic. In normal live healthy cells, PS is predominantly present in the inner leaflet of the bilayer cell membrane. When cells undergo apoptosis, action of translocase enzymes transport PS to the outer leaflet of the cell membrane, such that the cell surface becomes PS-rich and anionic. For many cells, this PS-rich apoptotic signal results in an 'eat me' signal to the macrophages. Therefore, presentation of PS-rich surface on nanoparticles and/or microparticles binding to specific cells can provide a way to artificially trigger a macrophagic response at a disease site, thereby rendering a 'triggered' inflammatory or immune response that can have potential therapeutic effects in diseases like cancer and/or pathogen infection.

Another interesting area of PS exposure on cells is in the context of platelets. Circulating 'resting' platelets do not have a PS-rich surface, but once platelets localize to an injury site and become activated to promote clotting, the activated platelets expose PS on their surface. This PS becomes the nidus of coagulation factor co-localization and assembly, which in the presence of calcium (Ca++) leads to formation of the tenase complex and subsequently the prothrombinase complex, resulting in amplification of thrombin generation. This thrombin then converts soluble fibrinogen to insoluble fibrin that becomes self-assembled as well as crosslinked to form the hemostatic clot. Therefore, exposure of PS on nanoparticle and/or microparticle systems localizing at an injury site can provide a way to mimic and amplify natural platelets' procoagulant mechanism of thrombin amplification, and render high hemostatic outputs in treating bleeding. This can be an efficient way to manage bleeding complications in patients that have disease-induced, drug-induced, or trauma-induced platelet dysfunctions.

In both cases described above, the exposure of PS on the PS-incorporated nanoparticles and/or microparticles should be 'target-specific' and 'stimulus-responsive', such that the PS is not exposed on the nanoparticles and/or microparticles in systemic circulation, so as to avoid rapid macrophagic clearance or systemic procoagulant risks. For this, the nanoparticle and/or microparticle surface can be covered (masked) with a releasable cloaking agent that can be cleaved off at the disease site to expose the PS trigger a target site-specific macrophagic or procoagulant response.

Accordingly, in some embodiments a composition for targeted amplification of coagulation or macrophage phagocytosis can include a plurality of nanoparticle and/or microparticle constructs. Each construct can have an outer portion that defines an outer surface of the construct, a plurality of targeting moieties and releasable cloaking agents that are linked to the outer portion and extend from the outer surface, and a plurality of phosphatidylserine phospholipids that extend from and/or define portions of the outer portion. The targeting moieties are configured to specifically bind to target molecules of a cell, tissue, and/or disease site in a subject. The releasable cloaking agents are configured to mask the phosphatidylserine phospholipids prior to binding of the target moieties to the target molecules and be released from the construct to expose the phosphatidylserine phospholipids upon binding of the target moieties to the target molecules.

In some embodiments, upon systemic administration of the composition to the subject and prior to binding of the target moieties to the target molecules, the cloaking agents inhibit exposure of the phosphatidylserine phospholipids so as to avoid macrophage clearance or systemic procoagulant risk. In other embodiments, upon binding of the target moieties to the target molecules of the cell, tissue, and/or disease site in the subject, exposed phosphatidylserine phospholipids promote macrophage engulfment and/or a procoagulant response.

The nanoparticle and/or microparticle constructs can be made from any biocompatible, biodegradable material that can form a nanoparticle or microparticle, which can include the plurality of phosphatidylserine phospholipids and to which the targeting moieties and releasable cloaking agents described herein can be attached, conjugated, and/or decorated. Examples of nanoparticles or microparticles can include liposomes, lipidic nanoparticles, a hydrogel, micelle, metal nanoparticles, polymer nanoparticles, dendrimers, quantum dots, and/or combinations of these materials which can include and/or be surface modified or engineered with the plurality of phosphatidylserine phospholipids, the targeting moieties and the releasable cloaking agents.

The nanoparticles or microparticles can have a maximum length or diameter of a diameter of about 50 nm to about 5 μm, preferably about 50 nm to about 200 nm, or more preferably about 100 nm to about 150 nm. In general, the nanoparticle or microparticle construct can have dimensions small enough to allow the composition to be systemically administered to a subject and targeted to cells, tissue, and/or disease sites of the subject. In some embodiments, the nanoparticle or microparticle construct can have a size that facilitates encapsulation of one or more therapeutic and/or imaging agents.

The nanoparticles or microparticles of the composition may be uniform (e.g., being about the same size) or of variable size. Particles may be any shape (e.g., spherical or rod shaped), but are preferably made of regularly shaped material (e.g., spherical). Other geometries can include substantially spherical, circular, triangle, quasi-triangle, square, rectangular, hexagonal, oval, elliptical, rectangular with semi-circles or triangles and the like. Selection of suitable materials and geometries are known in the art.

In some embodiments, the nanoparticles or microparticles can include lipidic nanoparticles or microparticles, polymer nanoparticles or microparticles, liposomes, and/or dendrimers with a membrane, shell, or surface. The lipidic nanoparticles or microparticles, polymer nanoparticles or microparticles, liposomes, and/or dendrimers can be formed from naturally-occurring, synthetic or semi-synthetic (i.e., modified natural) materials and a plurality of phosphatidylserine phospholipids, such as distearoylphosphatidylserine (DSPS).

In some embodiments, the lipidic nanoparticles or liposomes can include a membrane or shell that is formed from a naturally-occurring, synthetic or semi-synthetic material that is generally amphipathic (i.e., including a hydrophilic component and a hydrophobic component) and a plurality of the phosphatidylserine phospholipids. Examples of materials that can be used to form the membrane or shell of the lipidic nanoparticle or microparticle or liposome besides the plurality of the phosphatidylserine phospholipids include other lipids, such as fatty acids, neutral fats, phospholipids, oils, glycolipids, surfactants, cholesterol, aliphatic alcohols, waxes, terpenes and steroids, as well as semi-synthetic or modified natural lipids. Semi-synthetic or modified natural lipids can include natural lipids that have been chemically modified in some fashion. The lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the membrane or shell of the lipidic nano-particle or liposome with the plurality of phosphatidylserine phospholipids (e.g., DSPS), can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, DE), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

Examples of biocompatible, biodegradable polymers that can be used to form the nanoparticles are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, and blends and/or copolymers thereof.

Other examples of materials that may be used to form the nanoparticles or microparticles can include chitosan, poly(ethylene oxide), poly(lactic acid), poly(acrylic acid), poly(vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), gelatin, glycosaminoglycans (GAG), poly(hyaluronic acid), poly(sodium alginate), alginate, albumin, hyaluronan, agarose, polyhydroxybutyrate (PHB), copolymers thereof, and blends thereof.

In some embodiments, the nanoparticle and/or microparticle constructs can be liposomes. The liposomes can include a plurality of phospholipids and optionally cholesterol to define a lipid membrane. The phospholipids can include distearoylphosphatidylserine (DSPS) and at least one of distearoylphosphatidylcholine (DSPC), dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In some embodiments, distearoylphosphatidylserine (DSPS) be provided in the lipid membrane at about 1 mole % to about 20 mole %, about 5 mole % to about 15 mole %, or about 10 mole % to about 15 mole % of the lipid membrane.

In some embodiments, the liposome can be an unilamellar liposome and can have a width or diameter less than about 200 nm. For example, the width or diameter of the liposome can be about 100 nm to about 150 nm. In some embodiments, the liposome is about 150 nm in diameter. The liposome can have a high cholesterol content (e.g., at least about 20 mole %) in the membrane in order to efficiently encapsulate a water-soluble drug protecting the drug from plasma deactivation in circulation and prevent premature drug leakage due to membrane rigidity.

In other embodiments, the nanoparticles can include quantum dots, i.e., bright, fluorescent nanocrystals with physical dimensions small enough such that the effect of quantum confinement gives rise to unique optical and electronic properties. The quantum dots can be surface modified with a plurality of phosphatidylserine phospholipids such that the plurality of phosphatidylserine phospholipids are conjugated to and extend from an outer surface of the quantum dots.

In certain embodiments, the nanoparticles are optically detectable nanoparticles, such as metal nanoparticles that are surface modified with a plurality of phosphatidylserine phospholipids. Metals used to form the nanoparticles include, but not limited to, Ag, Au, Cu, Al, Fe, Co, Ni, Ru, Rh, Pd, and Pt or oxides thereof. In another embodiment, the metal comprises Fe or iron oxide. A further surface functional layer can be added or formed in combination with a metal core material. Such functional layers can include, but are not limited to, Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, tin oxide, antimony oxide, iron oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylprorolidone (PVP), and other polymers; stacked multiple layers at least two layers including above listed metal layers and non-metal layers, and the like. In some embodiments, the metal core can be Au, Ag, Fe, Ti, Ni, Cr, Pt, Ru, NiCr alloy, NiCrN, PtRh alloy, CuAuCo alloy, IrRh alloy and/or WRe alloy. The metals used should be biocompatible.

In some embodiments, the nanoparticle or microparticle can include a magnetic nanoparticles or microparticles that are surface modified with a plurality of phosphatidylserine phospholipids. "Magnetic particles" refers to magnetically responsive particles that contain one or more metals or oxides or hydroxides thereof. Compositions including optically detectable metal nano-particles or quantum dots can be detected in vivo upon systemic administration to a subject using magnetic resonance imaging (MRI), magnetic resonance spectroscopy (MRS), nuclear magnetic resonance imaging (NMR), multimodal imaging, fluorescent, positron emission tomography (PET), near infrared (NIR) imaging, X-ray imaging, and computed tomography (CT).

The targeting moieties that are linked to outer portion of nanoparticle or microparticle and configured to specifically bind to target molecules of a cell, tissue, and/or disease site of interest in a subject can be capable of targeting and/or adhering the nanoparticle and/or microparticle constructs to the targeted cell, tissue, and/or disease site of interest. The targeting moiety can include any molecule, or complex of molecules, which is/are capable of interacting with a cell surface or extracellular molecule or biomarker of a cell. The cell surface molecule can include, for example, a cellular protease, a kinase, a protein, a cell surface receptor, a lipid, and/or fatty acid.

In certain embodiments, the targeting moiety specifically binds a cell surface molecule of a target cell. As used herein, a targeting moiety "specifically binds" to a target molecule if it binds to or associates with the target molecule with an affinity or Ka (that is, an equilibrium association constant of a particular binding interaction with units of 1/M) of, for example, greater than or equal to about $10^5$ $M^{-1}$. In certain embodiments, the targeting moiety binds to the target molecule with a Ka greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^1$, $10^{12}$ $M^{-1}$, or $10^{13}$ $M^{-1}$. "High affinity" binding refers to binding with a Ka of at least $10^7$ $M^{-1}$, at least $10^8$ $M^{-1}$, at least $10^9$ $M^{-1}$, at least $10^{10}$ $M^1$, at least $10^{11}$ $M^{-1}$, at least $10^{12}$ $M^{-1}$, at least $10^{13}$ $M^{-1}$, or greater. Alternatively, affinity may be defined as an equilibrium dissociation constant (KD) of a particular binding interaction with units of M (e.g., $10^{-5}$ M to $10^{-13}$ M, or less). In certain aspects, specific binding means binding to the target molecule with a KD of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$ M, or $10^{-12}$ M or less. The binding affinity of the targeting moiety for the target molecule can be readily determined using conventional techniques, e.g., by competitive ELISA (enzyme-linked immunosorbent assay), equilibrium dialysis, by using surface plasmon resonance (SPR) technology (e.g., the BIAcore 2000 instrument, using general procedures outlined by the manufacturer); by radioimmunoassay; or the like.

In some embodiments, the targeting moiety can include, but is not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can comprise an antibody, such as a monoclonal antibody, a polyclonal antibody, or a humanized antibody, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide Fv fragments, scFv tandems ((scFv)2 fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating antibodies. These methods typically include the step of immunization of animals, typically mice, with a desired immunogen (e.g., a desired target molecule or fragment thereof). Once the mice have been immunized and boosted one or more times with the desired immunogen(s), antibody-producing hybridomas may be prepared and screened according to well-known methods. See, for example, Kuby, Janis, Immunology, Third Edition, pp. 131-139, W.H. Freeman & Co. (1997), for a general overview of monoclonal antibody production, that portion of which is incorporated herein by reference.

The targeting moiety need not originate from a biological source. The targeting moiety may, for example, be screened from a combinatorial library of synthetic peptides. One such method is described in U.S. Pat. No. 5,948,635, incorporated herein by reference, which describes the production of phagemid libraries having random amino acid insertions in the pIII gene of M13. This phage may be clonally amplified by affinity selection.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminopropyl]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, PA. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate a binding region of the polypeptide targeting moiety and select for a targeting moiety with superior binding characteristics as compared to the un-mutated targeting moiety.

This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moiety may be modified to make them more resistant to cleavage by proteases. For example, the stability of a targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, antibodies or variants thereof may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature, 321, 522-525 or Tempest et al. (1991), Biotechnology, 9, 266-273. Also, transgenic mice, or other mammals, may be used to express humanized antibodies. Such humanization may be partial or complete.

In certain embodiments, a targeting moiety as described herein may comprise a targeting peptide, which selectively directs the nanoparticle or microparticle constructs to a targeted cell or disease site. Targeting peptides for a targeted cell can be identified using various methods well known in the art. Many laboratories have identified the targeting peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130: 1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In other embodiments, the targeting moiety may comprise a ligand molecule, including, for example, ligands which naturally recognize a specific desired receptor of a target cell. Such ligand molecules include ligands that have been modified to increase their specificity of interaction with a target receptor, ligands that have been modified to interact with a desired receptor not naturally recognized by the ligand, and fragments of such ligands.

In still other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated that mimic those residues, which facilitate the interaction. Such mimetics may then be used as a targeting moiety to deliver the nanoparticle or microparticle construct to a target cell. For instance, non-hydrolyzable peptide analogs of such resides can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

In some embodiments, where the nanoparticle or microparticle constructs are used for promoting targeted amplification of coagulation and/or platelet aggregation in a subject in need thereof, the targeting moieties can include a plurality of von Willebrand factor-binding peptides (VBPs), collagen-binding peptides (CBPs) and fibrinogen mimetic peptides (FMPs). It was found that the platelet-mimetic adhesion- and aggregation-promoting functionalities can be achieved by including on, conjugating to, or decorating a nanoparticle with a plurality of three peptides, i.e., a von Willebrand factor-binding peptide (VBP), a collagen-binding peptide (CBP) and a fibrinogen mimetic peptides (FMPs). Liposomes bearing all three peptides (VBP, CBP and FMP), are able to promote arrest and aggregation of active platelets onto sites of liposome adhesion.

In some embodiments, the VBP peptide for vWF binding can include a recombinant GPIba fragment (rGPIba) containing the vWF binding sites (residues 1 to 302) or a short chain vWF-binding peptide. The GPIba fragment can be expressed in CHO cells and isolated, adapting methods described. The short vWF-binding peptide can include the amino acid sequence of TRYLRIHPQSWVHQI (SEQ ID NO: 1). A peptide having an amino acid sequence of SEQ ID NO: 1 can be synthesized using fluorenylmethyloxycarbonyl chloride (FMoc)-based solid phase chemistry on Knorr resin, and characterized using mass spectroscopy. Each vWF molecule has only one binding region for this peptide, and hence vascular injury sites presenting multiple vWF binding sites for multiple copies of this peptide decorated on the nanoparticle surface, provide a mechanism for enhanced adhesion of the nanoparticles with increasing shear.

In some embodiments, the CBP can include a peptide that comprises a short seven-repeat of the tripeptide GPO (i.e., $[GPO]_7$, SEQ ID NO: 2) with a helicogenic affinity to fibrillar collagen. The GPO trimer is based on amino acid repeats found in the native collagen structure. It has been reported that the activation of platelets usually caused by interaction with collagen through GPVI and GPIa/IIa, can also potentially occur when platelets interact with collagen-derived peptides. This can be a potential problem regarding decorating synthetic particle surfaces with collagen-derived peptides for binding of collagen, because in vivo the constructs can potentially interact with quiescent blood platelets and systemically activate them, posing thromboembolic risks. However, interaction of platelet receptors with collagen and the subsequent platelet activation mechanisms are dependent upon receptor clustering induced by multimeric long chain triple-helical fibrillar collagen and not by short collagen-mimetic peptide repeats. In fact, it has been shown that GPO-trimer repeats as high as a 30-mer (10 repeats) only partially interact with platelet GPIa/IIa and GPVI integrins and are incapable of activating platelets; yet they can effectively bind to fibrillar collagen via helicogenic interaction. Hence, this small CBP can promote adhesion to fibrillar collagen, but cannot activate quiescent platelets due to absence of long triple-helical conformation. The CBP like the VBP can also be synthesized using FMoc-based solid phase chemistry on Knorr resin, and characterized using mass spectroscopy.

In some embodiments, the FMP can include an RGD amino acid sequence motif that promotes active platelet aggregation. The RGD motif containing FMP may contain a single repeat of the RGD motif or may contain multiple repeats of the RGD motif, such as, for example, 2, or 5, or 10 or more repeats of the RGD motif. One of skill in the art will understand that conservative substitutions of particular amino acid residues of the RGD motif containing FMPs may be used so long as the RGD motif containing FMP retains the ability to bind comparably as the native RGD motif. One of skill in the art will also understand that conservative substitutions of particular amino acid residues flanking the RGD motif so long as the RGD motif containing FMP retains the ability to bind comparably as the native RGD motif.

In some embodiments, the FMP can include a cyclic RGD (cRGD) peptide having the amino acid sequence of cyclo-CNPRGDY(OEt)RC (SEQ ID NO: 3). A cyclic peptide having SEQ ID NO: 3 can have high selectivity and affinity to GPIIb-IIIa on activated platelets but do not bind or activate quiescent platelets nor interact with other RGD-binding integrins. The FMP like the VBP and CBP can be synthesized using FMoc-based solid phase chemistry on Knorr resin, and characterized using mass spectroscopy.

Advantageously, the VBPs, CBPs, and FMPs can each include about 5 to about 30 amino acids. By limiting the size of the peptides to about 5 to about 30 amino acids, the VBPs, CBPs, and FMPs can be spatially or topographically arranged on the flexible nanoparticle surface such that the VBPs, CBPs, and FMPs do not spatially mask each other and are able to adhere to a vascular surface, vascular disease site, and/or vascular injury site with exposed vWF and collagen and promote arrest and aggregation of active platelets onto sites of the synthetic platelet adhesion.

The VBPs, CBPs, and FMPs can be conjugated to the nanoparticle surface by reacting the peptides with through their N-termini to the carboxyl termini of a heterobifunctional PEG, such as maleimide-PEG-COOH. The PEG-peptide conjugates or PEGylated peptides can then be conjugated to the nanoparticle using known conjugation techniques.

The PEG molecules can have a variety of lengths and molecular weights, including, for example, PEG 200, PEG 1000, PEG 1500, PEG 4600, PEG 10,000, or combinations thereof. In other embodiments, the VBPs, CBPs, and FMPs can be conjugated to lipids that define the nanoparticle surface with PEG acrylate, or PEG diacrylate, molecules of a variety of molecular weights.

The ratio of VPBs to CPBs provided on the nanoparticle surface can be about 70:30 to about 30:70 and be adjusted accordingly to maximize adhesion under low-to-high shear conditions. In some embodiments, the ratio of VPB:CPB:FMP can be about 1:1:2 to 1:2:1 to 2:1:1. It will be appreciated, that other ratios can be used to enhance the nanoparticle adherence and activated platelet aggregation.

In some embodiments, where the nanoparticle and/or microparticle constructs are used to promote macrophage phagocytosis, the targeting moiety can specifically bind to an antigen on a target cancer cell or pathogen, such as a virus or prokaryotic cell of a microorganism (e.g., bacteria or fungi).

By "cancer cell" it is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like. In certain aspects, the cancer cell is a carcinoma cell.

In other embodiments, the cancer cell antigen can include at least one of 5T4, α2β1 integrin, AXL receptor tyrosine kinase (AXL), B-cell maturation antigen (BCMA), c-MET (Hepatocyte Growth Factor Receptor), C4.4a, carbonic anhydrase 6 (CA6), carbonic anhydrase 9 (CA9), Cadherin-6, CD19, CD22, CD25, CD27L, CD30, CD33, CD37, CD44v6, CD56, CD70, CD74, CD79b, CD123, CD138, carcinoembryonic antigen (CEA), cKit, collagen receptor, Cripto protein, CS1, delta-like canonical Notch ligand 3 (DLL3), endothelin receptor type B (EDNRB), ephrin A4 (EFNA4), epidermal growth factor receptor (EGFR), EGFRvIII, ectonucleotide pyrophosphatase/phosphodiesterase 3 (ENPP3), EPH receptor A2 (EPHA2), fibroblast growth factor receptor 2 (FGFR2), fibroblast growth factor receptor 3 (FGFR3), FMS-like tyrosine kinase 3 (FLT3), folate receptor 1 (FOLR1), glycoprotein non-metastatic B (GPNMB), guanylate cyclase 2 C (GUCY2C), human epidermal growth factor receptor 2 (HER2), human epidermal growth factor receptor 3 (HER3), Integrin alpha, lysosomal-associated membrane protein 1 (LAMP-1), Lewis Y, LIV-1, leucine rich repeat containing 15 (LRRC15), mesothelin (MSLN), mucin 1 (MUC1), mucin 16 (MUC16), sodium-dependent phosphate transport protein 2B (NaPi2b), Nectin-4, NMB, NOTCH3, p-cadherin (p-CAD), prostate-specific membrane antigen (PSMA), protein tyrosine kinase 7 (PTK7), protein tyrosine phosphatase mu (PTPmu), solute carrier family 44 member 4 (SLC44A4), SLIT like family member 6 (SLITRK6), STEAP family member 1 (STEAP1), tissue factor (TF), T cell immunoglobulin and mucin protein-1 (TIM-1), or trophoblast cell-surface antigen (TROP-2).

Non-limiting examples of antibodies that specifically bind to tumor antigens which may be used as a targeting moiety include Adecatumumab, Ascrinvacumab, Cixutumumab, Conatumumab, Daratumumab, Drozitumab, Duligotumab, Durvalumab, Dusigitumab, Enfortumab, Enoticumab, Figitumumab, Ganitumab, Glembatumumab, Intetumumab, Ipilimumab, Iratumumab, Icrucumab, Lexatumumab, Lucatumumab, Mapatumumab, Narnatumab, Necitumumab, Nesvacumab, Ofatumumab, Olaratumab, Panitumumab, Patritumab, Pritumumab, Radretumab, Ramucirumab, Rilotumumab, Robatumumab, Seribantumab, Tarextumab, Teprotumumab, Tovetumab, Vantictumab, Vesencumab, Votumumab, Zalutumumab, Flanvotumab, Altumomab, Anatumomab, Arcitumomab, Bectumomab, Blinatumomab, Detumomab, Ibritumomab, Minretumomab, Mitumomab, Moxetumomab, Naptumomab, Nofetumomab, Pemtumomab, Pintumomab, Racotumomab, Satumomab, Solitomab, Taplitumomab, Tenatumomab, Tositumomab, Tremelimumab, Abagovomab, Igovomab, Oregovomab, Capromab, Edrecolomab, Nacolomab, Amatuximab, Bavituximab, Brentuximab, Cetuximab, Derlotuximab, Dinutuximab, Ensituximab, Futuximab, Girentuximab, Indatuximab, Isatuximab, Margetuximab, Rituximab, Siltuximab, Ublituximab, Ecromeximab, Abituzumab, Alemtuzumab, Bevacizumab, Bivatuzumab, Brontictuzumab, Cantuzumab, Cantuzumab, Citatuzumab, Clivatuzumab, Dacetuzumab, Demcizumab, Dalotuzumab, Denintuzumab, Elotuzumab, Emactuzumab, Emibetuzumab, Enoblituzumab, Etaracizumab, Farletuzumab, Ficlatuzumab, Gemtuzumab, Imgatuzumab, Inotuzumab, Labetuzumab, Lifastuzumab, Lintuzumab, Lorvotuzumab, Lumretuzumab, Matuzumab, Milatuzumab, Nimotuzumab, Obinutuzumab, Ocaratuzumab, Otlertuzumab, Onartuzumab, Oportuzumab, Parsatuzumab, Pertuzumab, Pinatuzumab, Polatuzumab, Sibrotuzumab, Simtuzumab, Tacatuzumab, Tigatuzumab, Trastuzumab, Tucotuzumab, Vandortuzumab, Vanucizumab, Veltuzumab, Vorsetuzumab, Sotituzumab, Catumaxomab, Ertumaxomab, Depatuxizumab, Ontuxizumab, Blontuvetmab, Tamtuvetmab, or a tumor antigen-binding variant thereof. As used herein, "variant" is meant the antibody specifically binds to the particular antigen (e.g., HER2 for trastuzumab) but has fewer or more amino acids than the parental antibody (e.g., is a fragment (e.g., scFv) of the parental antibody), has one or more amino acid substitutions relative to the parental antibody, or a combination thereof.

By way of example, where the cell targeted comprises an ovarian cancer cell, the targeting moiety can comprise an antibody or peptide to human CA-125R. Over expression of CA-125 has implication in ovarian cancer cells. Alternatively, where the cell targeted comprises a malignant cancer, such as glioblastoma, the targeting moiety can comprise an antibody or peptide to extracellular growth factor receptor (EGFR), human transferrin receptor (TfR), and/or extracellular cleaved PTPmu. Overexpression of EGFR and TfR as well as extracellular cleavage of PTPmu has been implicated in the malignant phenotype of tumor cells.

Other targeting moieties can include a PSMA targeting moiety or PSMA ligand that can selectively recognize PSMA-expressing tumors, cancer cells, and/or cancer neovasculature in vivo. PSMA is a transmembrane protein that is highly overexpressed (100-1000 fold) on almost all prostate cancer (PC) tumors. Only 5-10% of primary PC lesions have been shown to be PSMA-negative. PSMA expression levels increase with higher tumor stage and grade.

Small molecule PSMA ligands bind to the active site in the extracellular domain of PSMA and are internalized and endosomally recycled, leading to enhanced tumor uptake and retention and high image quality. Examples of PSMA ligands are described in Afshar-Oromieh A, Malcher A, Eder M, et al. PET imaging with a [68Ga]gallium-labelled PSMA ligand for the diagnosis of prostate cancer: biodistribution in humans and first evaluation of tumor; Weineisen M, Schottelius M, Simecek J, et al. 68Ga- and 177Lu-Labeled PSMA I&T: Optimization of a PSMA-Targeted Theranostic Concept and First Proof-of-Concept Human Studies. J Nucl Med. 2015; 56:1169-1176. lesions. Eur J Nucl Med Mol Imaging. 2013; 40:486-495; Cho S Y, Gage K L, Mease R C, et al. Biodistribution, tumor detection, and radiation dosimetry of 18F-DCFBC, a low-molecular-weight inhibitor of prostate-specific membrane antigen, in patients with metastatic prostate cancer. J Nucl Med. 2012; 53:1883-1891; and Rowe S P, Gage K L, Faraj S F, et al. (1)(8)F-DCFBC PET/CT for PSMA-Based Detection and Characterization of Primary Prostate Cancer. J Nucl Med. 2015; 56:1003-1010.

Other examples of PSMA ligands are described in U.S. Pat. Nos. 6,875,886, 6,933,114, and 8,609,142, which are incorporated herein by reference in their entirety. Still other examples PSMA ligands are disclosed in U.S. Patent Application Publication No. 2015/0366968, U.S. Patent Application Publication No. 2015/0366968, 2018/0064831, 2018/0369385, and U.S. Pat. No. 9,889,199 all of which are incorporated by reference in their entirety.

The releasable cloaking agents are linked to the outer surface of the nanoparticle or microparticle and are configured to mask the phosphatidylserine phospholipids during systemic administration of the construct to the subject so as to avoid phosphatidylserine mediated macrophage clearance or systemic procoagulant risk. Upon binding of targeting moieties to the target molecules of the cell, tissue, and/or disease site and hence localization of nanoparticle or microparticle constructs to the cell, tissue, or disease site the cloaking agents are released so that the phosphatidylserine phospholipids are exposed and promote macrophage engulfment or phagocytosis and/or a procoagulant response only at the cell, tissue, or disease site.

In some embodiments, the cloaking agent can include a hydrophilic polymer that is releasably linked to the outer portion of the construct. For example, the cloaking agent can include a hydrophilic polymer that is releasably linked to a cholesterol molecule of a lipid membrane that forms an outer portion of the construct. The hydrophilic polymer can include, for example, polyethylene glycol (PEG). The PEG molecules can have a variety of lengths and molecular weights, including, for example, PEG 200, PEG 1000, PEG 1500, PEG 4600, PEG 10,000, or combinations thereof.

The amount or concentration of the hydrophilic polymer releasably linked to the construct is an amount or concentration effective to mask the phosphatidylserine phospholipids during systemic administration of the construct to the subject so as to avoid phosphatidylserine mediated macrophage clearance or systemic procoagulant risk. In some embodiments, the amount or concentration of cloaking agent can depend on the amount or concentration of phosphatidylserine phospholipids provide in or on the construct. For example, the phosphatidylserine phospholipids can be provided at about 1 mole % to about 20 mole %, about 5 mole % to about 15 mole %, or about 10 mole % to about 15 mole % of the lipid membrane and the cloaking agent can be provided at a similar mole % relative to the of phosphatidylserine phospholipids.

The cloaking agents are releasably linked to an outer portion of the construct with a cleavable linker. The cleavable linker is specifically or selectively cleaved at the cell, tissue, or disease site so that the phosphatidylserine phospholipids are only exposed at the cell, tissue, or disease site. Linkers cleavable at the cell, tissue, or disease site can include enzyme cleavable linkers that are cleaved by enzymes that are substantially unique or specific to the target cells, tissue, and/or disease site and/or have a higher concentration or activity compared to the concentration or activity at other cells, tissues, and/or disease sites in the subject, as well as radiation cleavable linkers that can be exposed to radiation at the target cells, tissue, and/or disease site.

Enzyme cleavable linkers are described, for example, in WO 2017/089894; WO 2016/146638; US2010273843; WO 2005/112919; WO 2017/089894; de Groot et al. (1999) J. Med. Chem. 42: 5277; de Groot et al. (2000) J Org. Chem. 43: 3093 (2000); de Groot et al., (2001) J Med. Chem. 66: 8815; WO 02/083180; Carl et al. (1981) J Med. Chem. Lett. 24: 479; Studer et al. (1992) Bioconjugate Chem. 3 (5): 424-429; Carl et al. (1981) J. Med. Chem. 24 (5): 479-480 and Dubowchik et al. (1998) Bioorg & Med. Chern. Lett. 8: 3347. In some embodiments, the enzyme cleavable linker can include at least one of a valine-citrulline linker, such as a glutamic acid-valine-citrulline linker, KTFKC (SEQ ID NO: 4), or VPLSLYSG (SEQ ID NO: 5).

The linkers can be cleavable by enzymes selected from: proteases (including enterokinases), nucleases, nitroreductases, phosphatases, β-glucuronidase, lysosomal enzymes, TEV, trypsin, plasmin, thrombin, cathepsin B and K, caspase, matrix metalloproteinases, phosphodiesterases, phospholipidases, esterases and β-galactosidases. Radiation cleavable linkers include, for example, 2-Nitrobenzyl derivatives, phenacyl ester, 8-quinolinyl benzenesulphonate, coumarin, phosphotriester, bis-arylhydrazone, bimane bithiopropionic acid derivatives.

In some embodiments, where the nanoparticle or microparticle constructs are used for promoting targeted amplification of coagulation and/or platelet aggregation in a subject in need thereof, the cleavable linker can be an enzyme cleavable linker that is cleaved by an enzyme, which is substantially unique or specific to a vascular injury site and/or has a higher concentration or activity compared to concentration or activity of other cells, tissues, and/or disease sites in the subject. The enzyme can include, for example, plasmin or thrombin and the enzyme cleavable linker can include a peptide having the amino acid sequence of KTFKC (SEQ ID NO: 4).

In other embodiments, where the nanoparticle and/or microparticle constructs are used to promote macrophage phagocytosis in a subject in need thereof, the cleavable linker can include an enzyme cleavable linker that is cleaved by an enzyme that is substantially unique or specific to a target cancer cell or pathogen, such as a virus or prokaryotic cell of a microorganism, and/or has a higher concentration or activity compared to the concentration or activity at other cells, tissues, and/or disease sites in the subject. The enzyme can include, for example, matrix metalloproteinase, and the enzyme cleavable linker can include a peptide having the amino acid sequence of VPLSLYSG (SEQ ID NO: 5).

In some embodiments, the nanoparticle and/or microparticle constructs can further include imaging agents (or detectable moieties) and/or therapeutic agents that are encapsulated by (e.g., within liposome, lipidic nanoparticle or microparticle, or polymer nanoparticle or microparticle), contained in (e.g., polymer nanoparticles or dendrimers), or conjugated to the nanoparticles and/or microparticles.

Imaging agents can include any substance that may be used for imaging or detecting a region of interest (ROI) in a subject and/or diagnosing the presence or absence of a disease or diseased tissue in a subject. The imaging agent can be selected such that it generates a signal, which can be measured and whose intensity is related (preferably proportional) to the distribution of the imaging agent and the constructs in the subject. Examples of imaging agents include, but are not limited to: radionuclides, fluorescent dyes, chemiluminescent agents, colorimetric labels, and magnetic labels. In one example, the imaging agent can include a radiolabel that is detected using gamma imaging wherein emitted gamma irradiation of the appropriate wavelength is detected. Methods of gamma imaging include, but are not limited to, SPECT and PET. For SPECT detection, the chosen radiolabel can lack a particular emission, but will produce a large number of photons in, for example, a 140-200 keV range. For PET detection, the radiolabel can be a positron-emitting moiety, such as 19F.

In another example, the imaging agent can include an MRS/MRI radiolabel, such as gadolinium, $^{19}F$, $^{13}C$, that is coupled (e.g., attached or complexed) with the composition using general organic chemistry techniques. The imaging agent can also include radiolabels, such as $^{18}F$, $^{11}C$, $^{75}Br$, or $^{76}Br$ for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, N Y 1986) the contents of which are hereby incorporated by reference. The imaging can also include $^{123}I$ for SPECT.

The imaging agent can further include known metal radiolabels, such as Technetium-99m ($^{99m}Tc$). Preparing radiolabeled derivatives of Tc99m is well known in the art. See, for example, Zhuang et al., "Neutral and stereospecific Tc-99m complexes: [$^{99m}$Tc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Therapeutic agents or bioactive agents, encapsulated by, contained in, and/or linked to the nanoparticle or microparticle constructs can include any substance capable of exerting a biological or therapeutic effect in vitro and/or in vivo. Therapeutic agents can also include any therapeutic or prophylactic agent used in the treatment (including the prevention, diagnosis, alleviation, or cure) of a malady, affliction, condition, disease, or injury in a subject. Examples of therapeutic agents include, but are not limited to procoagulants and anti-proliferative agents. The therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA.

In some embodiments, release of the therapeutic or imaging agent from the nanoparticle or microparticle construct of the composition can occur by desorption, diffusion through the polymer or lipid membrane, or polymer or lipid wall, nanoparticle or microparticle erosion, and/or disruption of the nanoparticle or microparticle structure, which can all be controlled by the type of the nanoparticle or microparticle, i.e., having it become swollen or degradable in the chosen microenvironment.

In some embodiments, the therapeutic or imaging agent can be released from the nanoparticle or microparticle composition through the use of an internal and/or external trigger. Internal triggers include the body's internal pH, chemical and enzymatic activity. External triggers can include light and ultrasound.

Advantageously, a nanoparticle or microparticle construct, which allows remote release of the therapeutic agent, can target or be targeted to a disease site, such as a vascular disease site or cancer site, by systemic administration (e.g., intravenous, intravascular, or intraarterial infusion) to the subject and once targeted to the site remotely released to specifically treat the targeted disease site tissue of the subject. Targeting and selective release of therapeutic agents allows treatment of such vascular diseases or cancer using therapeutic agents, which would provide an otherwise diminished therapeutic effect if not targeted and remotely released using the compositions described herein. In some embodiments, release of the therapeutic agent and/or imaging agent from the nanoparticle or microparticle of the composition can be triggered by an energy source that supplies energy to the composition effective to release the therapeutic agent or imaging agent from the nanoparticle or microparticle construct. The energy source can be external or remote from a subject, which allows non-invasive remote release of the therapeutic agent to the subject. The remote energy source can be, for example, a minimally invasive laser that can be inserted in vivo in the subject being treated or positioned external or ex vivo the subject. The energy from laser can be in the near infrared range to allow deep radiation penetration into tissue and remote release of therapeutic agent or imaging agent.

Therefore, in some embodiments, a nanoparticle or microparticle construct of the composition can be surface modified to be responsive to energy, from a remote source that is effective to release the therapeutic agent from the nanoparticle or microparticle upon mechanical disruption of the nanoparticle or microparticle membrane or shell after administering the composition to a subject.

In an exemplary embodiment, near infra-red (NIR)-responsive gold nanorods (GNRs) conjugated close to the surface of the nanoparticle or microparticle encapsulating or containing a therapeutic agent can exhibit plasmon resonance phenomena under tissue-penetrating NIR light, such that the resultant thermo-mechanical energy dissipation results in disruption of the nanoparticle or microparticle to render site-selective rapid drug release. Thus, in some embodiments, NIR-irradiation from specialized external or catheter-mediated laser devices can be used to remotely trigger rapid drug release at the targeted disease site via photothermal destabilization of GNR-modified nanoparticles.

Upon administration of the composition to a subject by, for example, intravascular administration, the composition can target a vascular disease site or cancer site being treated. In some embodiments, the composition can be imaged by, for example, magnetic resonance imaging or computed tomography, to confirm localization and targeting of the composition to the vascular disease site or cancer site. The composition targeted to the vascular disease site or cancer can be applied NIR from a remote NIR energy source that is external to the subject being treated to mechanically resonate or oscillate the GNRs on the nanoparticle or microparticle and rapidly release the therapeutic agent from the liposome membrane or shell due to defects in the membrane or shell caused by oscillation of the gold linked to the nanoparticle or microparticle.

It will be appreciated that other remote energy sources can be used to release the therapeutic agent or imaging agent from the nanoparticle or microparticle and that the selection of the energy source will depend at least in part on the nanoparticle or microparticle construct used to form the composition.

In some embodiments, the nanoparticle or microparticle constructs described herein can be provided in a pharmaceutical composition. Such a pharmaceutical composition may consist of the nanoparticle or microparticle constructs alone, in a form suitable for administration to a subject, or the pharmaceutical composition may comprise nanoparticle or microparticle constructs and one or more pharmaceutically acceptable carriers, one or more additional ingredients, one or more pharmaceutically acceptable therapeutic agents, bioactive agents, diagnostic agents, or some combination of these. The therapeutic agent may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the therapeutic agent may be combined and which, following the combination, can be used to administer the therapeutic agent to a subject.

As used herein, the term "physiologically acceptable" ester or salt means an ester or salt form of the therapeutic agent which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing nanoparticle or microparticle constructs into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions, which are suitable for ethical administration to humans, it will be understood by the skilled artisan that such compositions are generally for administration to animals of all sorts. Modification of pharmaceutical compositions for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, animals including commercially relevant animals such as cattle, pigs, horses, sheep, cats, and dogs, birds including commercially relevant birds such as chickens, ducks, geese, and turkeys.

Pharmaceutical compositions that are useful in the methods described herein may be administered, prepared, packaged, and/or sold in formulations for parenteral, oral, rectal, vaginal, topical, transdermal, pulmonary, intranasal, buccal, intravenous, or another route of administration.

The compositions described herein may be administered via numerous routes, including, but not limited to, parenteral, oral, rectal, vaginal, topical, transdermal, pulmonary, intranasal, buccal, or intravenous administration routes. The route(s) of administration will be readily apparent to the skilled artisan and will depend upon any number of factors including the type and severity of the disorder being treated, the type and age of the veterinary or human patient being treated, and the like.

Parenteral administration of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition on or through a surgical incision, by application of the composition on or through a tissue-penetrating non-surgical wound, and the like. In particular, parenteral administration is contemplated to include, but is not limited to, cutaneous, subcutaneous, intraperitoneal, intramuscular, intrasternal injection, intravenous, and intra-arterial.

Formulations of a pharmaceutical composition suitable for parenteral administration can include the nanoparticle or microparticle constructs combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles. Such formulations may further comprise one or more additional ingredients including, but not limited to, suspending, stabilizing, or dispersing agents. In one embodiment of a formulation for parenteral administration, the therapeutic agent is provided in dry (i.e., powder or granular) form for reconstitution with a suitable vehicle (e.g., sterile pyrogen free water) prior to parenteral administration of the reconstituted composition.

The pharmaceutical compositions described herein may also be formulated so as to provide slow, prolonged or controlled release. In general, a controlled-release preparation is a pharmaceutical composition capable of releasing nanoparticle or microparticle constructs at a desired or required rate to maintain constant activity for a desired or required period of time.

A pharmaceutical composition described herein may be prepared, packaged, or sold in bulk, as a single unit dose, or as a plurality of single unit doses. As used herein, a "unit dose" is discrete amount of the pharmaceutical composition comprising a predetermined amount of the activity. The amount of the activity is generally equal to the dosage, which would be administered to a subject or a convenient fraction of such a dosage such as, for example, one-half or one-third of such a dosage.

The pharmaceutical compositions may be prepared, packaged, or sold in the form of a sterile injectable aqueous or oily suspension or solution. This suspension or solution may be formulated according to the known art, and may comprise, in addition to the nanoparticle or microparticle constructs, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The pharmaceutical composition may be administered to an animal as needed. The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

In some embodiments, the nanoparticle or microparticle constructs can form platelet-mimicking procoagulant nanoparticles (PPNs) that can be used to diminish bleeding and blood loss as well as deliver therapeutic agents to the vasculature. The PPNs can include a biocompatible flexible nanoparticle that includes an outer portion that defines an outer surface of the nanoparticle, a plurality of targeting moieties and releasable cloaking agents that are linked to the outer portion and extend from the outer surface, and a plurality of phosphatidylserine phospholipids that extend from and/or define portions of the outer portion. The targeting moieties can include a plurality of von Willebrand factor-binding peptides (VBPs), collagen-binding peptides (CBPs), and/or fibrinogen mimetic peptides (FMPs). The releasable cloaking agents can be configured to mask the phosphatidylserine phospholipids prior to binding of the target moieties to von Willebrand factor, collagen, and/or GPIIb-IIIa and be released from the nanoparticle to expose the phosphatidylserine phospholipids upon binding of the target moieties to von Willebrand factor, collagen, and/or GPIIb-IIIa.

In some embodiments, upon systemic administration of the PPNs to the subject and prior to binding of the targeting moieties to the von Willebrand factor, collagen, and/or GPIIb-IIIa, the cloaking agents inhibit exposure of the phosphatidylserine phospholipids so as to avoid systemic procoagulant risk. In other embodiments, upon binding of the targeting moieties to von Willebrand factor, collagen, and/or GPIIb-IIIa, exposed phosphatidylserine phospholipids can promote a procoagulant response at a site of the binding.

In some embodiments, the cloaking agent includes a hydrophilic polymer that is releasably linked to the outer portion of the construct. The hydrophilic polymer can include, for example, polyethylene glycol.

In some embodiments, the cloaking agent is releasably linked to an outer portion of the nanoparticle with an enzyme cleavable linker. The enzyme cleavable linker can be cleaved by an enzyme that is substantially unique or specific to a vascular injury site and/or has a higher concentration or activity compared to the concentration or activity at other cells, tissues, and/or disease sites in the subject. The enzyme can include at least one of a plasmin or thrombin and the enzyme cleavable linker can include a peptide having the amino acid sequence of KTFKC (SEQ ID NO: 4).

In some embodiments, the PPN can have a diameter of about 50 nm to about 5 μm, preferably about 50 nm to about 200 nm, or more preferably about 100 nm to about 150 nm.

In some embodiments, the PPN can be a liposome. The liposome can include a plurality of phospholipids and optionally cholesterol to define a lipid membrane. The phospholipids can include distearoylphosphatidylserine (DSPS) and at least one of distearoylphosphatidylcholine (DSPC), dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In some embodiments, the distearoylphosphatidylserine (DSPS) can include about 1 mole % to about 20 mole %, about 5 mole % to about 15 mole %, or about 10 mole % to about 15 mole % of the phospholipids that form the lipid membrane.

By way of example, FIG. 1 illustrates membrane compositional elements for manufacturing PPNs can include DSPC, DSPS, DSPE-PEG-CBP, DSPE-PEG-VBP, DSPE-PEG-FMP, cholesterol, and cholesterol-KTFKC (SEQ ID NO: 4)-PEG. The VBP, CBP and FMP peptides are vWF-binding, collagen-binding and fibrinogen-mimetic peptides that integratively mimic the adhesion and aggregation mechanisms of platelets. The DSPS component allows incorporation of phosphatidylserine (PS) in the PPN membrane. The Cholesterol-KTFKC (SEQ ID NO: 4)-PEG component allows incorporation of a plasmin-cleavable cloak to mask the PS on PPN surface.

In some embodiments, the VBPs, CBPs, and FMPs can be spatially or topographically arranged on the outer surface such that the VBPs, CBPs, and FMPs do not spatially mask each other and the construct is able to adhere to a vascular surface, vascular disease site, and/or vascular injury site with exposed vWF and collagen and promote arrest and aggregation of active platelets onto sites of the construct adhesion.

In some embodiments, the VBPs, CBPs, and FMPs are conjugated to the outer surface with PEG linkers.

In other embodiments, the platelet-mimicking procoagulant nanoparticles can have a shape, size and elastic modulus that facilitates margination to a vascular wall and their bio-interactions upon administration to a vasculature of a subject.

In some embodiments, the VBPs can have an amino acid sequence of SEQ ID NO: 1, the CBPs can have an amino acid sequence of SEQ ID NO: 2, and the FMPs can have an amino acid sequence of SEQ ID NO: 3. The ratio of VPBs to CPBs provided on the outer surface can be about 70:30 to about 30:70. The ratio of VPB:CPB:FMP is about 1:1:2 to 1:2:1 to 2:1:1.

Figure 2:
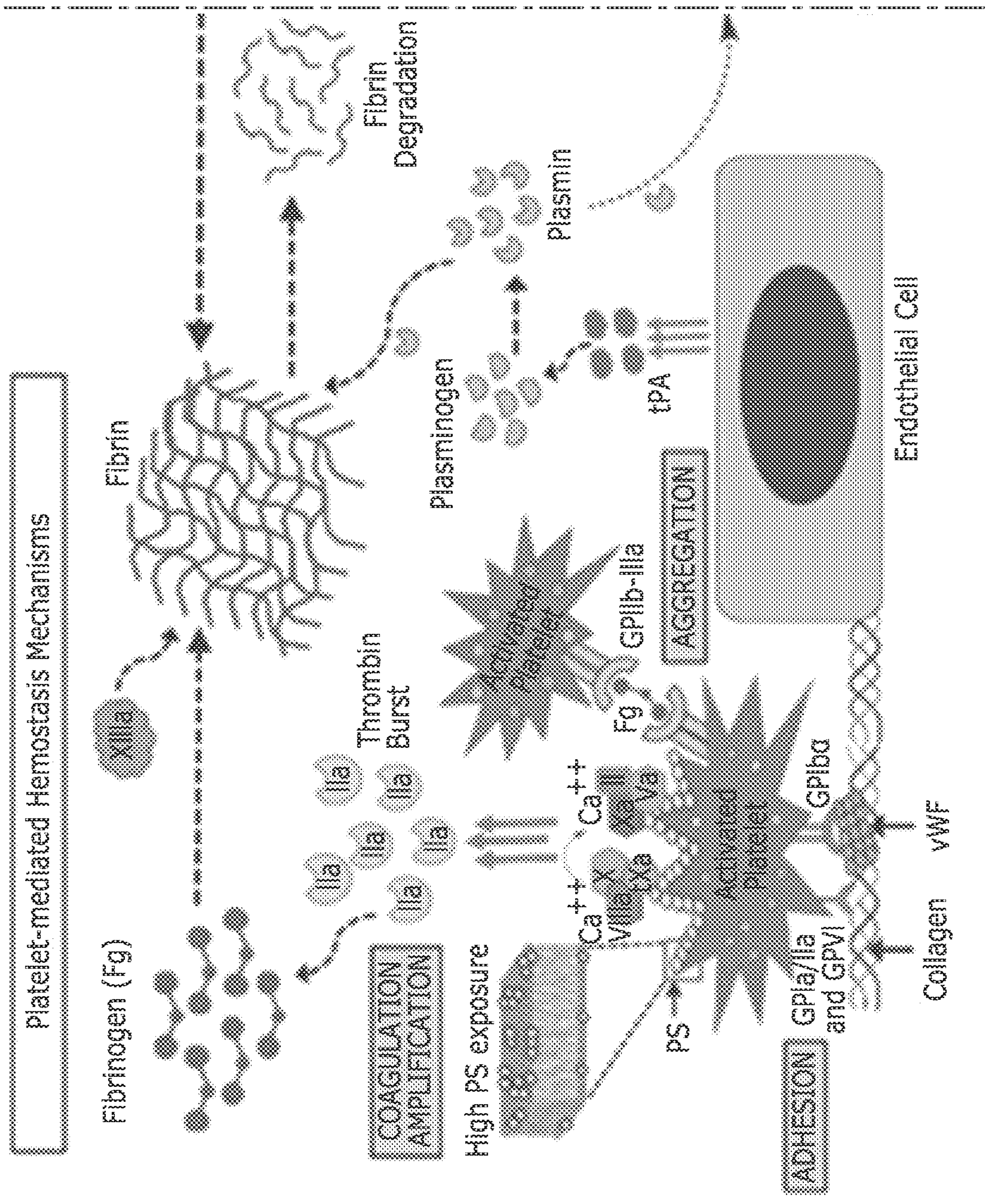
FIG. 2 illustrates platelet-mediated hemostatic mechanisms and their mimicry by PPN. Platelets promote hemostasis by: (1) Adhesion to von Willebrand Factor (vWF via glycoprotein GPIbα) and collagen (via glycoproteins GPIa/IIa and GPVI), (2) Aggregation of active platelets via fibrinogen (Fg) binding to integrin $\alpha_{IIb}\beta_3$ (glycoprotein GPIIb-IIIa), and (3) Exposure of phosphatidylserine (PS) on procoagulant active platelet surface to render thrombin amplification, that can enhance fibrin generation from Fg; Fibrin is subsequently degraded by plasmin (generated from plasminogen by tissue plasminogen activator or tPA). Platelet-mimicking procoagulant nanoparticles (PPN) can mimic platelet's primary hemostatic mechanisms by binding to vWF via vWF-binding peptide (VBP), to collagen via collagen-binding peptide (CBP) and interacting with active platelet GPIIb-IIIa via fibrinogen-mimetic peptide (FMP); Furthermore, locally generated plasmin can cleave off the polyethylene glycol (PEG) mask from the surface of PPNs to expose PS that can amplify thrombin site-specifically, resulting in generation of fibrin from Fg to replenish and stabilize the hemostatic clot.
Figure 2:
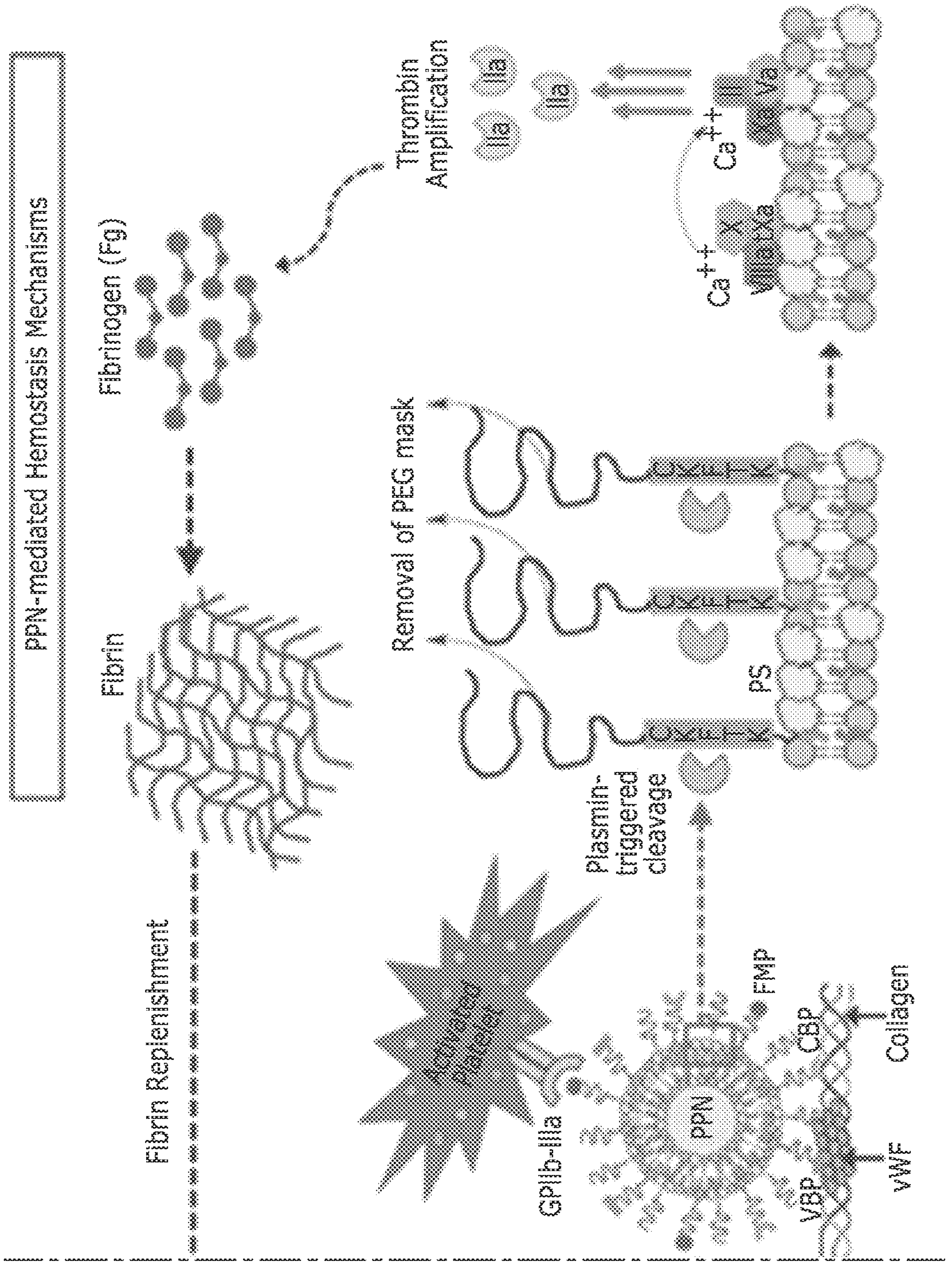

FIG. 2 shows the PPN can mimic platelet's primary hemostatic mechanisms by binding to vWF via vWF-binding peptide (VBP), to collagen via collagen-binding peptide (CBP) and interacting with active platelet GPIIb-IIIa via fibrinogen-mimetic peptide (FMP); Furthermore, locally generated plasmin can cleave off the polyethylene glycol (PEG) mask from the surface of PPNs to expose PS that can amplify thrombin site-specifically, resulting in generation of fibrin from Fg to replenish and stabilize a hemostatic clot. The PPNs could be potentially advantageous in treating trauma-induced hyperfibrinolysis where high amounts of tPA production and plasmin generation occur at the injury site.

It is therefore an aspect of the application that administration, such as for example intravenous administration, of the PPNs described herein to a subject with a vascular injury can diminish the bleeding time in the subject. It is a further aspect of the application that the PPNs provide a nanostructure that binds with a vascular injury site as well as activated platelets and enhances their rate of aggregation to aid in stopping bleeding and particularly hemorrhage from traumatic injury, medical bleeding, and non-compressible hemorrhage.

In some embodiments, the subject can have or be at increased risk of thrombocytopenia. The thrombocytopenia can be caused by or result from dehydration, leukemia, myelodysplastic syndrome, aplastic anemia, liver failure, sepsis, leptospirosis, congenital amegakaryocytic thrombocytopenia, thrombocytopenia absent radius syndrome, fanconi anemia, Bernard-Soulier syndrome, May-Hegglin anomaly, grey platelet syndrome, Alport syndrome, Wiskott-Aldrich syndrome, idiopathic thrombocytopenic purpura, thrombotic thrombocytopenia purpura, hemolytic-uremic syndrome, disseminated intravascular coagulation, paroxysmal nocturnal hemoglobinuria, antiphospholipid syndrome, systemic lupus erythematosus, post-transfusion purpura, neonatal alloimmune thrombocytopenia, hypersplenism, dengue fever, Gaucher's disease, zika virus, medication-induced thrombocytopenia, niacin toxicity, Lyme disease, and thrombocytapheresis.

In other embodiments, the PPNs described herein can be used to treat a bleeding disorder. In one embodiment, the bleeding disorder is hemophilia. In a further embodiment, the hemophilia is hemophilia A. In yet another embodiment the hemophilia is hemophilia B. In one embodiment, the hemophilia is hemophilia A. In another embodiment, the hemophilia is acquired hemophilia A with inhibitory auto antibodies to FVIII. In one embodiment, the hemophilia is congenital hemophilia B with inhibitors. In another embodiment, the hemophilia is acquired hemophilia B with inhibitory auto antibodies to FIX.

In other embodiments, the bleeding disorder is a non-hemophilia bleeding disorder. In one embodiment, the bleeding disorder is blood loss from trauma. In another embodiment, the bleeding disorder is FVII deficiency. In one embodiment, the bleeding disorder is FV deficiency. In another embodiment, the bleeding disorder is FX deficiency. In one embodiment, the bleeding disorder is FXI deficiency. In one embodiment, the bleeding disorder is FXIII deficiency. In one embodiment, the bleeding disorder is fibrinogen deficiency. In one embodiment, the bleeding disorder is prothrombin deficiency. In another embodiment, the bleeding disorder is dilutional coagulopathy. In a further embodiment, the bleeding disorder is thrombocytopenia. In yet another embodiment, the bleeding disorder is blood loss from high-risk surgeries. In another embodiment, the bleeding disorder is intracerebral hemorrhage. In one embodiment, the bleeding disorder is von Willebrand disease. In a further embodiment, the bleeding disorder is von Willebrand disease with inhibitors to von Willebrand factor.

In other embodiments, the bleeding disorder is a congenital platelet function defect, including, but not limited to, platelet storage pool disorder, Glanzmann's thrombasthenia, or Bernard-Soulier syndrome. In one embodiment, the bleeding disorder is an acquired platelet function defect. In one embodiment, the bleeding disorder is a congenital deficiency of Factor II, Factor V, Factor VII, Factor X, or Factor XI. In one embodiment, the bleeding disorder is neonatal and pediatric coagulopathies. In one embodiment, the bleeding disorder is a platelet function disorder. In another embodiment, the bleeding disorder is heparin-induced thrombocytopenia. In one embodiment, the bleeding disorder is disseminated intravascular coagulation.

In other embodiments, the non-hemophilia bleeding disorder is blood loss from trauma. In another embodiment, the non-hemophilia bleeding disorder is FVII deficiency. In one embodiment, the non-hemophilia bleeding disorder is FV deficiency. In another embodiment, the non-hemophilia bleeding disorder is FX deficiency. In one embodiment, the non-hemophilia bleeding disorder is FXI deficiency. In one embodiment, the non-hemophilia bleeding disorder is FXIII deficiency. In one embodiment, the non-hemophilia bleeding disorder is fibrinogen deficiency. In one embodiment, the non-hemophilia bleeding disorder is prothrombin deficiency. In another embodiment, the non-hemophilia bleeding disorder is dilutional coagulopathy. In a further embodiment, the non-hemophilia bleeding disorder is thrombocytopenia. In yet another embodiment, the non-hemophilia bleeding disorder is blood loss from high-risk surgeries. In another embodiment, the non-hemophilia bleeding disorder is intracerebral hemorrhage. In one embodiment, the non-hemophilia bleeding disorder is von Willebrand disease. In a further embodiment, the non-hemophilia bleeding disorder is von Willebrand disease with inhibitors to von Willebrand factor.

In one embodiment, the non-hemophilia bleeding disorder is a congenital platelet function defect, including, but not limited to, platelet storage pool disorder, Glanzmann's thrombasthenia, or Bernard-Soulier syndrome. In one embodiment, the non-hemophilia bleeding disorder is an acquired platelet function defect. In one embodiment, the non-hemophilia bleeding disorder is a congenital deficiency of Factor II, Factor V, Factor VII, Factor X, or Factor XI. In one embodiment, the non-hemophilia bleeding disorder is neonatal and pediatric coagulopathies. In one embodiment, the non-hemophilia bleeding disorder is a platelet function disorder. In another embodiment, the non-hemophilia bleeding disorder is heparin-induced thrombocytopenia. In one embodiment, the non-hemophilia bleeding disorder is disseminated intravascular coagulation. In other embodiments, the non-hemophilia bleeding disorder is any disorder known to one of skill in the art.

In other embodiments, the nanoparticle or microparticle constructs can be used to induce a macrophage response to a cell and/or pathogen in order to treat cancer and/or pathogen infection in a subject in need thereof. In this embodiment, each construct can have an outer portion that defines an outer surface of the construct, a plurality of targeting moieties and releasable cloaking agents that are linked to the outer portion and extend from the outer surface, and a plurality of phosphatidylserine phospholipids that extend from and/or define portions of the outer portion. The targeting moieties are configured to specifically bind to target molecules of a cancer cell or pathogen in a subject. The releasable cloaking agents are configured to mask the phosphatidylserine phospholipids prior to binding of the target moieties to the cancer cell or pathogen and be released from the construct to expose the phosphatidylserine phospholipids upon binding of the target moieties to the cancer cell or pathogen.

In some embodiments, upon systemic administration of the composition to the subject and prior to binding of the target moieties to the cancer cells or pathogen, the cloaking agents inhibit exposure of the phosphatidylserine phospholipids so as to avoid macrophage clearance of the constructs. In other embodiments, upon binding of the target moieties to the cancer cells or pathogen in the subject, exposed phosphatidylserine phospholipids promote macrophage engulfment of the cancer cells or pathogen.

In some embodiments, the cloaking agent includes a hydrophilic polymer that is releasably linked to the outer portion of the construct. The hydrophilic polymer can include, for example, polyethylene glycol.

In some embodiments, the cloaking agent is releasably linked to an outer portion of the construct with an enzyme cleavable linker. The enzyme cleavable linker can be cleaved by an enzyme that is substantially unique or specific to the cancer cells or pathogen and/or has a higher concentration or activity compared to other cells, tissues, and/or disease sites in the subject. The enzyme can include a matrix metalloprotease, and the enzyme cleavable linker can include a peptide having an amino acid sequence of VPLSLYSG (SEQ ID NO: 5).

In some embodiments, the nanoparticle and/or microparticle construct can have a diameter of about 50 nm to about 5 μm, preferably about 50 nm to about 200 nm, or more preferably about 100 nm to about 150 nm.

In some embodiments, the nanoparticle and/or microparticle construct can be a liposome. The liposome can include a plurality of phospholipids and optionally cholesterol to define a lipid membrane. The lipid membrane can include distearoylphosphatidylserine (DSPS) and at least one of distearoylphosphatidylcholine (DSPC), dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In some embodiments, the distearoylphosphatidylserine (DSPS) can include about 1 mole % to about 20 mole %, about 5 mole % to about 15 mole %, or about 10 mole % to about 15 mole % of the phospholipids that form the lipid membrane.

In some embodiments, the targeting moiety can bind a cancer cell surface molecule. The cancer cell surface molecule can include a cancer cell antigen on the surface of a cancer cell. For example, the cancer cell antigen can include at least one of 5T4, α2β1 integrin, AXL receptor tyrosine kinase (AXL), B-cell maturation antigen (BCMA), c-MET (Hepatocyte Growth Factor Receptor), C4.4a, carbonic anhydrase 6 (CA6), carbonic anhydrase 9 (CA9), Cadherin-6, CD19, CD22, CD25, CD27L, CD30, CD33, CD37, CD44v6, CD56, CD70, CD74, CD79b, CD123, CD138, carcinoembryonic antigen (CEA), cKit, collagen receptor, Cripto protein, CS1, delta-like canonical Notch ligand 3 (DLL3), endothelin receptor type B (EDNRB), ephrin A4 (EFNA4), epidermal growth factor receptor (EGFR), EGFRvIll, ectonucleotide pyrophosphatase/phosphodiesterase 3 (ENPP3), EPH receptor A2 (EPHA2), fibroblast growth factor receptor 2 (FGFR2), fibroblast growth factor receptor 3 (FGFR3), FMS-like tyrosine kinase 3 (FLT3), folate receptor 1 (FOLR1), glycoprotein non-metastatic B (GPNMB), guanylate cyclase 2 C (GUCY2C), human epidermal growth factor receptor 2 (HER2), human epidermal growth factor receptor 3 (HER3), Integrin alpha, lysosomal-associated membrane protein 1 (LAMP-1), Lewis Y, LIV-1, leucine rich repeat containing 15 (LRRC15), mesothelin (MSLN), mucin 1 (MUC1), mucin 16 (MUC16), sodium-dependent phosphate transport protein 2B (NaPi2b), Nectin-4, NMB, NOTCH3, p-cadherin (p-CAD), prostate-specific membrane antigen (PSMA), protein tyrosine kinase 7 (PTK7), protein tyrosine phosphatase mu (PTPμ) solute carrier family 44 member 4 (SLC44A4), SLIT like family member 6 (SLITRK6), STEAP family member 1 (STEAP1), tissue factor (TF), T cell immunoglobulin and mucin protein-1 (TIM-1), or trophoblast cell-surface antigen (TROP-2).

In some embodiments, the constructs can further include a therapeutic agent and/or an imaging agent conjugated to or defining at least a portion of the construct.

In some embodiments, the therapeutic agent can further include at least one chemotherapeutic agent, anti-proliferative agent, biocidal agent, biostatic agent, or anti-microbial agent.

In other embodiments, the construct can further include a plurality of Gold Nanorods (GNRs) conjugated to the outer surface, the GNRs allowing photothermal destabilization of the nanoparticle construct and release of the therapeutic and/or imaging agent in response to near-infrared (NIR) light.

The nanoparticle or microparticle constructs used to induce a macrophage response to a cell and/or pathogen can be administered to a subject via any known route, such as via an intravenous injection. By way of example, a composition comprising a plurality of nanoparticle or microparticle constructs can be intravenously administered to a subject that is known to or suspected of having a tumor.

In some embodiments, the nanoparticle or microparticle constructs are administered to a subject to treat a neoplastic disease, such as a solid tumor, e.g., a solid carcinoma, sarcoma or lymphoma, and/or an aggregate of neoplastic cells. The tumor may be malignant or benign and can include both cancerous and pre-cancerous cells.

The nanoparticle or microparticle constructs administered to the subject can circulate in the subject and bind to and/or complex with the targeted cancer cells by binding and/or complexing of the targeting moiety with the cell surface molecule of the targeted cell. Typically, the cell targeted nanoparticle or microparticle constructs can bind to and/or complex with the targeted cells within about 10 minutes, about 15 minutes, about 20 minutes, about 25 minutes, about 30 minutes, about 35 minutes, about 40 minutes, about 45 minutes, about 50 minutes, about 55 minutes, or about 1 hour or less.

The cloaking agent can be released by, for example, enzymatic cleavage of an enzyme cleavable linker to expose the phosphatidylserine phospholipids on the construct to promote macrophage engulfment of the cancer cells or pathogen in subject.

In certain embodiments, the subject has a cancer characterized by the presence of a solid tumor, a semi-solid tumor, a primary tumor, a metastatic tumor, a liquid tumor (e.g., a leukemia or lymphoma), and/or the like. Cancers, which can be treated using the methods described herein, include, but are not limited to, adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, biliary tract cancer, osteosarcoma, fibrous histiocytoma, brain cancer, brain stem glioma, cerebellar astrocytoma, malignant glioma, glioblastoma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, acute lymphocytic and myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, choriocarcinoma, hematological neoplasm, adult T-cell leukemia, lymphoma, lymphocytic lymphoma, stromal tumors and germ cell tumors, or Wilms tumor. In some embodiments, the cancer is lung cancer, breast cancer, prostate cancer, colorectal cancer, gastric cancer, liver cancer, pancreatic cancer, brain and central nervous system cancer, skin cancer, ovarian cancer, leukemia, endometrial cancer, bone, cartilage and soft tissue sarcoma, lymphoma, neuroblastoma, nephroblastoma, retinoblastoma, or gonadal germ cell tumor.

In some embodiments, the subject has a cancer selected from breast cancer, glioblastoma, neuroblastoma, head and neck cancer, gastric cancer, ovarian cancer, skin cancer (e.g., basal cell carcinoma, melanoma, or the like), lung cancer, colorectal cancer, prostate cancer, glioma, bladder cancer, endometrial cancer, kidney cancer, leukemia (e.g., T-cell acute lymphoblastic leukemia (T-ALL), acute myeloid leukemia (AML), etc.), liver cancer (e.g., hepatocellular carcinoma (HCC), such as primary or recurrent HCC), a B-cell malignancy (e.g., non-Hodgkin lymphomas (NHL), chronic lymphocytic leukemia (CLL), follicular lymphoma, mantle cell lymphoma, diffuse large B-cell lymphoma, and the like), pancreatic cancer, thyroid cancer, any combinations thereof, and any sub-types thereof.

A pharmaceutical composition comprising the cancer cell targeted nanoparticle or microparticle constructs, which can induce a macrophage response to a cancer cell described herein, can be administered to the subject in a therapeutically effective amount. In some embodiments, a therapeutically effective amount of the cancer cell targeted nanoparticle or microparticle constructs is an amount that, when administered alone (e.g., in monotherapy) or in combination (e.g., in combination therapy) with one or more additional therapeutic agents, in one or more doses, is effective to reduce the symptoms of the pathological condition (e.g., cancer) in the individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the conjugate. According to some embodiments, when the subject has cancer, the methods described herein promote apoptosis and/or necrosis of the cancer when the cancer cell targeted nanoparticle or microparticle constructs are administered in an effective amount.

Dosing is dependent on severity and responsiveness of the condition (e.g., cancer) to be treated. Optimal dosing schedules can be calculated from measurements of drug accumulation in the body of the individual. The administering physician can determine optimum dosages, dosing methodologies and repetition rates. Optimum dosages may vary depending on the relative potency of individual agent and can generally be estimated based on EC50s found to be effective in in vitro and in vivo animal models, etc. In general, dosage may be given once or more daily, weekly, monthly, or yearly. The treating physician can estimate repetition rates for dosing based on measured residence times and concentrations of the nanoparticle or microparticle constructs in bodily fluids or tissues. Following successful treatment, it may be desirable to have the subject undergo maintenance therapy to prevent the recurrence of the disease state, where the cell targeted nanoparticle or microparticle constructs can be administered in maintenance doses once or more daily, to once every several months, once every six months, once every year, or at any other suitable frequency.

In some embodiments, a drug, and/or therapeutic agent, such as a chemotherapeutic (e.g., doxorubicin) can also be loaded into or conjugated to the nanoparticle or microparticle constructs during formation to provide a drug loaded cell targeted nanoparticle or microparticle construct. Advantageously, cell targeted nanoparticle or microparticle constructs can target or be targeted to specific cells or tissue of subject, such as tumors, cancers, and metastases, by systemic administration (e.g., intravenous, intravascular, or intraarterial infusion) to the subject and once targeted to the cells or tissue specifically treat the targeted cells or tissue of subject (e.g., tumors, cancers, and metastasis).

The following example is for the purpose of illustration only and is not intended to limit the scope of the claims, which are appended hereto.

EXAMPLE

This example describes the development of platelet-mimicking procoagulant nanoparticles (PPNs) (FIGS. 1 and 2) that mimic the procoagulant function of native platelets. We used a hybrid liposomal nanoparticle system where the liposome membrane contained distearoylphosphatidylserine (DSPS) together with other lipopeptide components that enabled injury site-specific adhesion and aggregation. Given that exposed phosphatidylserine would present a procoagulant risk in the circulation and also could elicit rapid clearance by macrophages, PPNs were modified with cholesterol-tethered polyethylene glycol that cloaked the phosphatidylserine in circulation but could be cleaved off by plasmin specifically at the injury site to expose phosphatidylserine. This exposed phosphatidylserine could then promote platelet-mimetic, site-specific thrombin amplification and fibrin generation resulting in improved hemostatic clot formation and stability. We first evaluated the ability of PPNs to enable plasmin-triggered phosphatidylserine exposure and resultant assembly of coagulation factors at the PPN surface. We then established that phosphatidylserine-exposed PPNs could amplify thrombin generation in human plasma depleted of native platelets and that this thrombin could generate fibrin resulting in stable clot formation. Next, we evaluated PPNs given prophylactically to mice with thrombocytopenia and assessed their hemostatic efficacy compared to syngeneic platelets for curbing tail bleeding. PPNs were then evaluated in rat and mouse traumatic hemorrhage models to assess their effect on blood loss and animal survival.

Materials and Methods

In this study we manufactured and evaluated procoagulant platelet-mimetic nanoparticles (PPNs) that mimic platelet adhesion, aggregation and hemostatic functions at the vascular injury site. We evaluated these PPNs in vitro and in vivo for hemostatic properties and ability to staunch bleeding and improve survival in rodent models of traumatic hemorrhage. PPNs that contained Cholesterol-KTFKC (SEQ ID NO: 4)-$PEG_{2000}$ were designed to expose phosphatidylserine at the PPN surface in response to plasmin. Control nanoparticles lacked Cholesterol-KTFKC (SEQ ID NO: 4)-$PEG_{2000}$. For all in vitro and in vivo studies, the nanoparticle:platelet ratio was maintained at approximately 100:1. In vitro studies included the thrombin generation assay, rotational thromboelastometry, scanning electron microscopy, overall hemostatic potential assay and microfluidic analysis.

In vivo studies were carried out in accordance with protocols approved by Case Western Reserve University IACUC (Protocol 2016-0012) and following standard ISTH guidelines. These studies involved a mouse model of thrombocytopenia, and rat and mouse models of traumatic hemorrhage. Treatment of antibody-induced thrombocytopenic mice with PPNs or control nanoparticles was randomized, and tail bleeding time and blood loss were measured. In the rat liver injury traumatic hemorrhage model, treatment with PPNs compared to control nanoparticles or saline was randomized, and blood loss was measured at one hour post-treatment and survival was calculated at 3 hours post-treatment. The mouse traumatic hemorrhage model was used as an additional group to assess long-term survival at 3 days after injury, with PPNs or control nanoparticles administered 30 minutes before injury.

PPN and Control Nanoparticle Manufacture and Characterization

Liposome nanoparticles were manufactured using the thin film rehydration and extrusion technique. For control liposomes, DSPC, cholesterol, DSPE-PEG2000-VBP, DSPE-$PEG_{2000}$-CBP, DSPE-$PEG_{2000}$-FMP and DSPE-$mPEG_{1000}$ were homogeneously mixed at 0.625, 0.3, 0.0125, 0.0125, 0.025 and 0.025 mole fractions, respectively, in 1:1 chloroform:methanol. Solvent was removed via rotary evaporation, and the thin lipid film was rehydrated with 0.9% NaCl at a concentration of $1\times10^5$ moles lipid per mL. This lipid suspension was subjected to 10 freeze/thaw cycles and subsequent extrusion through 200 nm pore diameter polycarbonate membrane using a pneumatic extruder (Northern Lipids, Burnaby, Canada) to create 'VBP+CBP+FMP'-decorated control nanoparticles that mimic the adhesion and aggregation functions of platelets. PPNs were manufactured using the same fabrication protocol as above, with the following membrane component mole fractions: DSPC (0.55), Cholesterol (0.3), Cholesterol-KTFKC (SEQ ID NO: 4)-$PEG_{2000}$ (0.15), DSPS (0.1), DSPE-PEG2000-VBP (0.0125), DSPE-$PEG_{2000}$-CBP (0.0125), and DSPE-$PEG_{2000}$-FMP (0.025). The DSPS incorporation allowed for the phosphatidylserine to be presented on the PPN surface and the Cholesterol-KTFKC (SEQ ID NO: 4)-$PEG_{2000}$ incorporation allowed for the cloaking of this phosphatidylserine with the cloak amenable to be removed via plasmin-triggered cleavage of the KTFKC (SEQ ID NO: 4) sequence. Dynamic light scattering (DLS), cryo-transmission electron microscopy (cryo-TEM) and atomic force microscopy (AFM) were used to characterize PPN size distribution. Incorporation of phosphatidylserine into PPN membrane was confirmed using Annexin V staining. For this, PPNs were modified with DSPE-$PEG_{2000}$-biotin (0.01 mole fraction), incubated on avidin-coated glass slides, washed, and stained with Alexa Fluor-647-conjugated Annexin V. To evaluate concentration dependent plasmin-triggered exposure of phosphatidylserine on the PPN surface, DSPE-$PEG_{2000}$-biotin incorporated PPNs containing Cholesterol-KTFKC (SEQ ID NO: 4)-$PEG_{2000}$ were first incubated on avidin-coated glass slides, then the immobilized PPNs were incubated with (or without) plasmin (1, 10, 50, 100, and 200 nM) and subsequently stained with Annexin V. To confirm FVa and FXa immobilization on PPN, similarly biotinylated control nanoparticles or PPNs were immobilized on avidin-coated glass slide, incubated with platelet-poor plasma for an hour, then washed, incubated with Factor Va and Factor Xa antibodies for an hour each, and then further incubated with Alexa 488-conjugated secondary antibody to FVa and FXa.

Thrombin Generation and ROTEM Assays in Plasma and SEM Imaging of Fibrin Clots

Platelet-rich plasma (PRP) was obtained by centrifuging human whole blood (WB) at 1500 g for 15 minutes at room temperature. The PRP was further centrifuged (13000 g for 5 minutes) to obtain platelet-poor plasma (PPP). The platelet counts in PRP and PPP were monitored using a Multisizer 3 Coulter Counter (Beckman Coulter, Brea, CA). The PRP platelet count was maintained at 150,000 per μL (lower limit of normal human platelet count), and the PRP was adjusted with PPP to create thrombocytopenic plasma with platelet counts of 20,000 per μL ($TCP_{20K}$) and 5000 per μL ($TCP_{5K}$). For thrombin generation studies, a thrombin-sensitive fluorescent substrate Rhodamine 110-bis-(p-Tosyl-L-Glycyl-L-Prolyl-L-Arginine Amide) and Tissue Factor (TF) was added to 100 μL of recalcified normal or thrombocytopenic plasma to study the effects of control nanoparticle versus PS-cloaked PPN versus PS-exposed PPN (at dose of 100 particles per platelet) on thrombin generation kinetics. The effect of control nanoparticles and PPN treatment on clot characteristics in platelet-depleted whole blood was evaluated using ROTEM. For this, normal or thrombocytopenic plasma was combined with initially separated hematocrit to form reconstituted whole blood with normal or depleted platelet count and subjected to ROTEM (EXTEM) assays with nanoparticles added in it. Clot formation time (CFT) and maximum clot firmness (MCF) were measured. Additionally, separate studies were done to assess fibrin morphology of clots formed in calcified thrombocytopenic plasma in presence of PPN, using scanning electron microscopy (SEM). For these studies, the fibrin clots were fixed with 3% glutaraldehyde, washed, fixed with 2% osmium tetroxide, washed again, dehydrated with increasing concentrations of ethanol (35%, 50%, 70%, 95%, and 100%), critical point dried using hexamethyldisilazane (HMDS), mounted and sputter coated. The dried clots were imaged with a Helios NanoLab™ 650 SEM at the Swagelok Center for Surface Analysis of Materials (SCSAM). Fiber thickness and pore size in the images obtained were analyzed using ImageJ.

Measurement of PPN Effects on Fibrin Generation and Clot Stability Under Fibrinolytic Conditions The effect of control nanoparticles versus PPNs on fibrin kinetics under a lytic environment was studied using the overall hemostatic potential (OHP) assay. Two types of buffers were prepared prior to the assay, one for the overall coagulation potential (OCP) and the other for overall hemostasis potential (OHP). The OCP buffer contained $CaCl_2$) (40 mM) and thrombin (0.5 IU/ml) in Tris buffer (66 mM Tris and 130 mM NaCl, pH 7). For OHP assay, t-PA (660 ng/ml) was added to the above-described OCP. In a 96 well-plate, 60 μl of plasma was added to each well and mixed with the respective buffers for OCP or OHP. Absorbance values at 405 nm were recorded over time for a 40 min period to construct fibrin generation vs. degradation curves. The effect of control nanoparticles versus PPNs on clot characteristics was further evaluated in ROTEM under tPA-induced lytic conditions. For this, 25 μg/ml of tPA was added to whole blood and the effects on ROTEM parameters were evaluated in presence of SP or PPN (nanoparticle dose of 100 particles per platelet). Specifically, two parameters were assessed: (1) Maximum Clot Firmness (MCF) maintenance time, defined as the time for which at least 80% MCF was maintained post reaching MCF, and (2) Maximum Lysis (ML) as a % of MCF at 60 min. In a separate experimental set-up, PRP was spiked with Alexa Fluor-647 labeled Fibrinogen, 50 μL volume of this plasma was placed on collagen-coated glass slide, and fluorescent clots were formed by adding thrombin (100 nM). The clots on the glass slide were vacuum-sealed within parallel plate microfluidic chamber and exposed to flow of plasma containing tPA (25 μg/ml) plus control nanoparticles or PPNs. The flow was maintained at a shear stress of 5 dyn·$cm^{-2}$ and the clot was imaged under inverted fluorescence microscope to monitor 'loss' of fibrin fluorescence under flow due to the fibrinolytic action of tPA-generated plasmin. Correspondingly, the fibrin lysis product was collected and analyzed by D-dimer ELISA assay to quantify the extent of fibrinolysis.

In Vivo Evaluation of PPNs in a Thrombocytopenic Mouse Model

Wild-type C57/BL6J mice were injected intraperitoneally with anti-CD42b (anti-GPIba) antibody (0.5 μg/g) and 18-24 hours later, platelet counts were measured on retro-orbitally drawn blood, using a Hemavet 950 (Drew Scientific, Miami Lakes, FL). After confirming significant thrombocytopenia (TCP) at this time-point, additional batches of mice (3 male+3 female=6 per group) were administered with the antibody and 18-24 hours post antibody administration, control nanoparticles or PPNs (nanoparticle dose of 2 mg/kg) were injected in these TCP mice retro-orbitally. Two hours after nanoparticle administration, the tails of these mice were transected 1 mm from the tip with a sharp surgical blade and immersed in warm (37° C.) saline. The time needed for bleeding to stop (bleeding time) was recorded and the collected blood was analyzed for hemoglobin (marker for blood loss) via the Sodium Lauryl Sulfate method using UV spectrometry at 535 nm. In separate experiments, syngeneic platelets were isolated from mice by collecting whole blood and centrifuging to get PRP, which was further centrifuged to obtain platelet pellet. This platelet pellet was resuspended in Tyrode's buffer containing $PGI_2$ to prevent clumping. Additional mice were injected intraperitoneally with anti-CD42b antibody (0.5 μg/g) as before and 18-24 hours later platelet counts were measured on retro-orbitally drawn blood to confirm thrombocytopenia as before. Tail bleeding assessment was carried out on three normal mice and three TCP mice to confirm that the bleeding time and blood loss in these mice are statistically similar to the normal and TCP mice used for the positive and negative control groups in the nanoparticle treatment studies. After confirming this, additional six TCP mice (3 male and 3 female) were administered retro-orbitally with syngeneic platelet dose at 250 platelets/nL. Thirty minute after syngeneic platelet administration, the tail was clipped as before, and tail bleeding time and blood loss were measured. Since the positive (normal mice) and negative control (TCP mice) data for these studies were statistically similar to the normal and TCP mice in the nanoparticle treatment studies, the syngeneic platelet treatment group (PLTs) data was pooled and statistically compared with the nanoparticle treatment data.

In Vivo Evaluation of PPNs in a Rat Liver Injury Traumatic Hemorrhage Model

A rat liver injury model (FIG. 6A) was used with >30% liver resection that causes severe intraperitoneal hemorrhage. SAS Sprague Dawley rats (~300 g) were acclimated to laboratory space for 48 hours. Rats were anesthetized with isoflurane, maintained on 100% oxygen with a non-rebreather mask and ophthalmic ointment was applied. To monitor vitals, a rectal thermometer, pulse oximeter and blood pressure cuff were placed. A tail vein catheter was placed to enable treatment (saline or control nanoparticle or PPN) administration. The abdomen of the rats was shaved, and subcutaneous buprenorphine and intramuscular injection of lidocaine at the incision site were administered. The peritoneal cavity was opened, and the liver exposed. The cavity was packed with pre-weighed absorbent gauze and the liver was cut sharply 1.5 cm from the superior vena cava removing both median and lateral lobes. The abdomen was immediately closed. Rats were then administered with 0.5 mL of saline or 0.5 ml of control nanoparticles or PPNs at 2 mg/kg dose, via the tail vein catheter at 0.25 mL/min. These studies were powered to blood loss at 60 min post-treatment (n=5 per treatment group), since in traumatic injury the first hour post-injury is considered to be the most critical for controlling hemorrhage and improving survival (termed the 'golden hour'). The vitals were monitored every 1 minute for the first 30 minutes, every 5 minutes for the next 150 minutes. One hour after injury, the gauze was removed from the abdomen and weighed to determine blood loss (assuming blood density of 1 g/mL), the abdomen was sutured close and the wound area was injected with lidocaine. Three hours post-treatment, rats were euthanized with an overdose of pentobarbital. Post-euthanasia, clearance organs (heart, lungs, liver, spleen, kidney) were harvested for histology and immunostaining. For this, organs were fixed in formalin, processed and slides were made for Carstairs' and immunostaining. Sections of the liver injury site were deparaffinized and rehydrated by washing with xylene then ethanol. Antigen retrieval was performed by Tris-EDTA at 60° C. overnight. Slides were washed, blocked in 10% serum with 1% bovine serum albumin in TBS for 2 hours, incubated with anti-fibrin(ogen) antibody, followed by incubation with the Alexa 488 labeled secondary antibody, washed, protected with coverslips, and imaged using Olympus FV1000 fluorescence confocal microscope. SP or PPN (red Rh B), and fibrin(ogen) (green FITC) fluorescence were imaged for the same field of view.

In Vivo Evaluation of PPNs in a Mouse Traumatic Hemorrhage Model 8-12 week old male C57 BL/6 mice were anesthetized with 2% isoflurane, injected with 2 mg/kg of either PPN or control nanoparticles via femoral vein and allowed to recover for 30 minutes. After 30 minutes, 25% of circulating blood volume was removed by blind cardiac puncture followed by midline laparotomy, resection of a standardized piece of the left liver lobe and skin closure. Mice were placed in their cages with ample food and water and observed for 3 days. Mortality, if occurred, was noted. All procedures were performed using sterile technique.

Statistical Analysis

For analysis of Annexin V fluorescence and FVa/FXa antibody fluorescence analysis on immobilized control nanoparticles versus PPNs, two tailed t-test was used. For analysis of clot fluorescence in microfluidic set-up under fibrinolytic condition, two way ANOVA with Tukey's multiple comparisons test was used. All other in vitro data were analyzed using a one-way ANOVA with Tukey's multiple comparisons test. Blood loss was assessed with a Log-rank (Mantel-Cox) test and Gehan-Breslow-Wilcoxon test. For blood loss analysis in the thrombocytopenic mouse bleeding model, we considered 50% reduction in bleeding time (seconds) between the saline (control) group versus the PPN-treated group with 0.9 (90%) power and 95% confidence; the power analysis estimated that 6 animals per group were needed. For blood loss analysis in the rat liver injury traumatic hemorrhage model, we considered 33% reduction in blood loss (volume) between the saline group versus the PPN-treated group with 0.9 (90%) power and 95% confidence; the power analysis estimated 5 animals per group were needed. Studies were powered to measure blood loss because to study survival with 90% power and 95% confidence would have required 21 animals per group. A p value of $<0.05$ was considered statistically significant.

Reagents

Distearoyl-sn-glycero-3-phosphocholine (DSPC), Distearoyl-sn-glycero-3-phospho-ethanolamine-N-[methoxy (polyethylene glycol)1000] (DSPE-mPEG1000), Distearoyl-sn-glycero-3-phosphoethanolamine-N-[maleimide (polyethylene glycol)2000](DSPE-PEG2000-Mal), Distearoyl-sn-glycero-3-phosphoethanolamine-N-[azido(polyethylene glycol)2000] (DSPE-PEG2000-Azide), Distearoyl-sn-glycero-3-phospho-L-serine (DSPS), and Distearoyl-sn-glycero-3-phospho-ethanolamine-N-[biotinyl(polyethylene glycol)2000] (DSPE-PEG2000-biotin) were purchased from Avanti Polar Lipids (Alabaster, AL, USA). Rhodamine B-dihexadecanoyl-sn-glycero-3-phosphoethanolamine (DHPE-RhB) was purchased from Invitrogen (Carlsbad, CA, USA). The peptides CTRYLRIHPQSWVHQI (VBP) (SEQ ID NO: 6), C[GPO]7 (SEQ ID NO: 7)(CBP), cyclo-{Pra}CNPRGD{Tyr(OEt)}RC (SEQ ID NO: 3)(FMP), and {Pra}KTFKC (SEQ ID NO: 4)(plasmin-cleavable peptide or PCP) were obtained from Genscript (Piscataway, NJ, USA). Sterile normal saline (0.9% NaCl) was purchased from Baxter (Deerfeld, IL, USA). Cholesterol, rat tail type I collagen, copper(II) sulfate ($CuSO_4$), Tris(3-hydroxypropyl triazolyl methyl)amine (THPTA), sodium ascorbate, glutaraldehyde, hexamethyldisilazane, prostaglandin $I_2$ and Cholesteryl-TEG-Azide were from Sigma-Aldrich (Saint Louis, MO, USA). Ethylenediamine Tetraacetic Acid (EDTA), cellulose dialysis tubing (MWCO 2 k and 3.5 k), phosphate buffered saline (PBS), chloroform, methanol, were purchased from Fisher Scientific (Pittsburgh, PA, USA). VBP and CBP were conjugated to DSPE-PEG2000-Mal via thiol-maleimide coupling and FMP was conjugated to DSPE-PEG2000-azide via copper-catalyzed alkyne-azide cycloaddition (CuCAAC). The PCP was conjugated to DSPE-PEG2000-Mal via thiol-maleimide coupling and then conjugated to Cholesteryl-TEG-azide via copper-catalyzed cycloaddition. Peptide-lipid conjugates were purified by dialysis and characterized by MALDI-TOF mass spectrometry. Adenosine di-phosphate (ADP), TRAP-6 and soluble calf skin type I collagen were obtained from Bio/Data Corporation (Horsham, PA, USA). Human plasmin was obtained from Hematologic Technologies (Essex Junction, VT, USA). For ROTEM studies, all reagents were purchased from ROTEM (Munich, Germany). Fluorescent human fibrinogen (Alexa Fluor-647 labeled), Rhodamine 110-bis-(p-Tosyl-L-Glycyl-L-Prolyl-L-Arginine Amide), Annexin V (Alexa Fluore-647 labeled), and human D-Dimer ELISA kit were obtained from Thermo Fisher (Pittsburgh, PA). G-100 Sephadex beads were purchased from GE Healthcare (Chicago, IL, USA). The parallel plate microfluidic chamber was obtained from Glycotech (Gaithersburg, MD, USA). Anti-Fibrinogen antibody, anti-Factor Va antibody, anti-Factor Xa antibody, and recombinant human Tissue Plasminogen Activator were from Abcam (Cambridge, MA). Alexa 488 conjugated secondary antibody was obtained from Novus Biologicals (Centennial, CO). For in vitro human whole blood or plasma studies, citrated human whole blood was drawn from healthy, aspirin-refraining adult donors via venipuncture in accordance with IRB protocol approved by the University Hospitals of Cleveland. For mouse thrombocytopenia model studies C57BL/6J mice were purchased from Jackson Laboratory (Bar Harbor, ME). For rat liver hemorrhage studies, SAS Sprague Dawley Rats were purchased from Charles River (Wilmington, MA). Mouse platelet depleting antibodies were obtained from Emfret Analytics (Eibelstadt, Germany). Isoflurane, buprenorphine, pentobarbital, lidocaine, ketamine and xylazine were obtained from Patterson Veterinary (Greeley, CO, USA). All in vivo studies were carried out per approved IACUC protocols at CWRU and University of Pittsburgh.

Theoretical Basis of Nanoparticle Number and Dose Calculations

Lipid molecules assembled in the SP and PPN vesicle membrane are assumed to be predominantly cylindrical in shape since these are double-tailed phospholipids with packing parameter ~1. Average phospholipid head group size: a=0.7 $nm^2$. Average phospholipid hydrophobic tail length: l=2 nm. Average lipid volume: a*l=1.4 $nm^3$. Membrane depth=21 (since 2 lipids are packed tail-to-tail in lamellar assembly)

Total lipids/particle=$N_{tot}$=Membrane Volume÷Lipid Volume $$N_{tot} = \frac{\frac{4\pi}{3}r^3 - \frac{4\pi}{3}(r-21)^3}{a*1} = \frac{\frac{4\pi}{3}(75\ \text{nm})^3 - \frac{4\pi}{3}(71\ \text{nm})^3}{1.4\ \text{nm}^3} = \frac{4\pi}{4.2}*(75^3 - 71^3) = 191{,}379$$

Assuming vesicles to be 150 nm in diameter (i.e. 75 nm in radius)

$N_m$=total average moles of lipids in one batch of SP or PPN (mol)=$10^{-5}$ mol $N_A$=Avogadro's number ($mol^{-1}$)=$6.023*10^{23}$ Therefore, theoretical number of nanoparticles per 1 ml batch=$N_p=N_m*N_A/N_{tot}=10^{-5}*6.023*10^{23}/191{,}379=3.14*10^{13}$ nanoparticles per ml.

Theoretical Particle Calculation for TGA Studies

For 100 μL PRP used per assay, platelet number=~$3*10^7$ platelets. SP or PPN nanoparticles were added in this at appropriate volume to maintain ratio in the range of 100 nanoparticles/platelet.

Mouse Dose Calculation at 2 mg/kg

For 20 g mouse, 0.0024 ml of particle solution was used which theoretically amounts to $7.2*10^{10}$ particles. For TCP mouse with average platelet number of 250 platelets/nl: 1.5 ml blood with $3.75*10^{8}$ platelets. Thus theoretically there is ~192 nanoparticles/platelet in systemic circulating dose, such at the site of tail clip injury the particle:platelet performing ratio can be assumed to still be ~100:1.

Rat Dose Calculation at 2 mg/kg

SD Rat platelet count is average $0.5*10^{9}$/mL. For 300 g rat 0.036 ml of SP or PPN solution was administered, which amounts to ~$1.08*10^{12}$ particles. Assuming average rat blood volume to be 15 ml blood, average total number of platelets is $7.5*10^{9}$. Therefore, with 0.036 ml particle dose, particle:platelet theoretical ratio is 144:1. Thus, at the site of liver injury, the particle:platelet performing ratio can be assumed to still be ~100:1.

In Vivo Evaluation of PPN in Mouse Trauma Model of 'liver Injury+Cardiac Puncture'

8-12 week old male C57 BL/6 mice were anesthetized with 2% isoflurane, injected with 2 mg/kg of either PPN or control particles via femoral vein and allowed to recover for 30 minutes. After 30 minutes, 25% of circulating blood volume was removed by blind cardiac puncture followed by midline laparotomy, resection of a standardized piece of the left liver lobe and skin closure. Mice were placed in their cages with ample food and water and observed for 3 days. Mortality, if occurred, was noted. All procedures were performed using sterile technique.

Results

Design and Characterization of PPNs

Figure 3A:
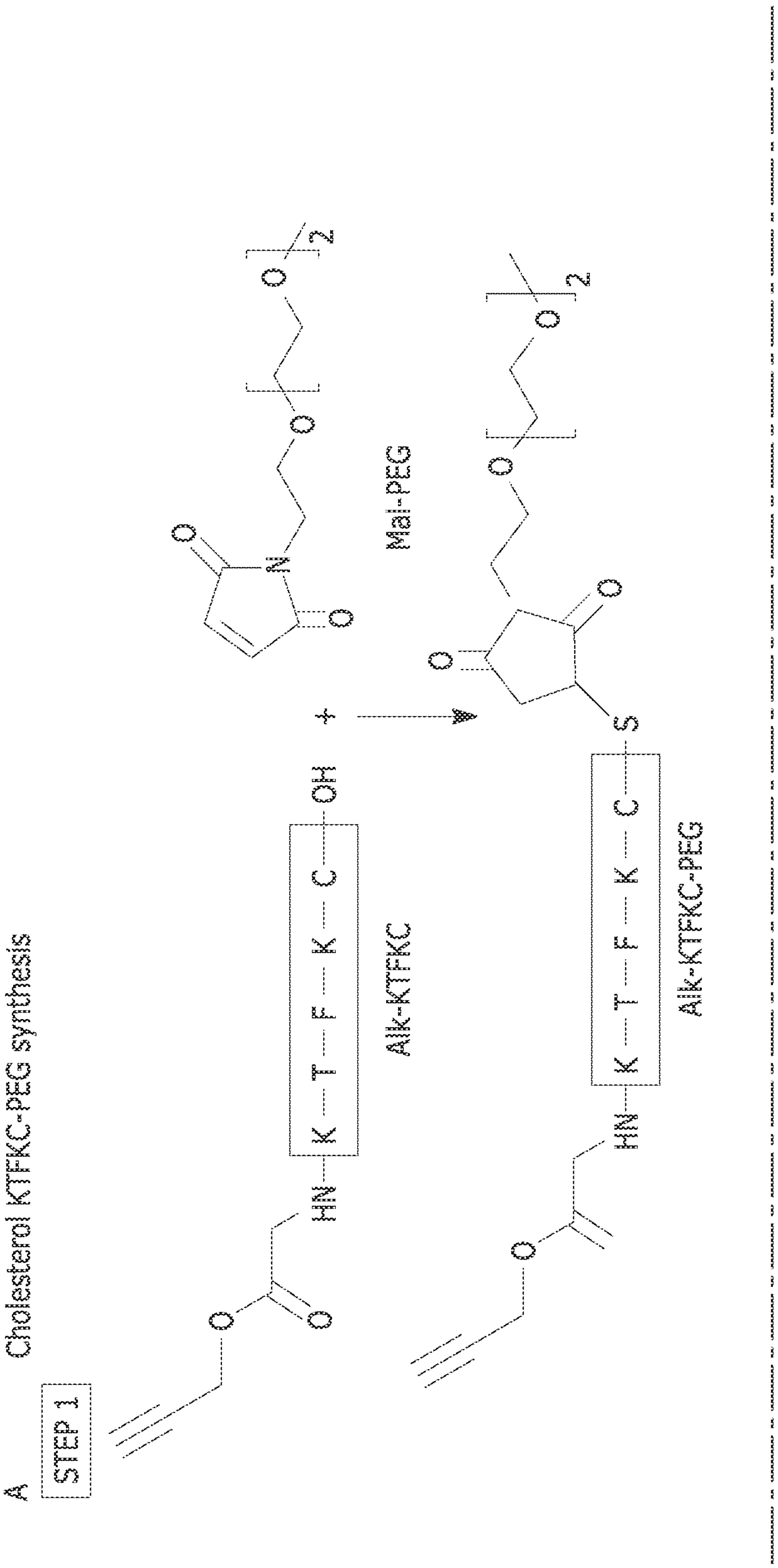
FIGS. 3(A-E) illustrate design and characterization of PPNs. (A) Shown is the two-step process for synthesis of Cholesterol-KTFKC (SEQ ID NO: 4)-PEG using Alkyne-terminated plasmin-cleavable peptide (Alk-KTFKC (SEQ ID NO: 4)), Maleimide-terminated polyethylene glycol (Mal-PEG), and Azide-terminated Cholesterol-Triethylene glycol (Cholesterol-TEG-azide). Cholesterol-KTFKC (SEQ ID NO: 4)-PEG was incorporated into PPNs providing a PEG cloak that could be cleaved by plasmin. (B) Matrix-assisted laser desorption ionization-time of flight (MALDI-TOF) mass spectrometry was used to characterize synthesized Cholesterol-KTFKC (SEQ ID NO: 4)-PEG and its plasmin-induced degradation (Th: Theoretical mass). (C) Shown is the design of PPN vesicles and their size characterization by dynamic light scattering (DLS), cryo-transmission electron microscopy (cryo-TEM) and atomic force microscopy (AFM). The PPN diameter ranged from 100 to 150 nm. (D) Shown are representative images and fluorescence intensity quantification of fluorescently labeled Annexin V that was bound to exposed phosphatidylserine at the surface of immobilized PPNs after addition of plasmin. (E) Shown are representative images and fluorescence intensity quantification of Alexa 488-labeled antibody bound to factors FVa and FXa (green fluorescence) of the prothrombinase complex that was assembled at the surface of PPNs with exposed phosphatidylserine but not control nanoparticles without exposed phosphatidylserine (Control NP). * indicates $p \leq 0.05$ (two tailed t-test).
Figure 3A:
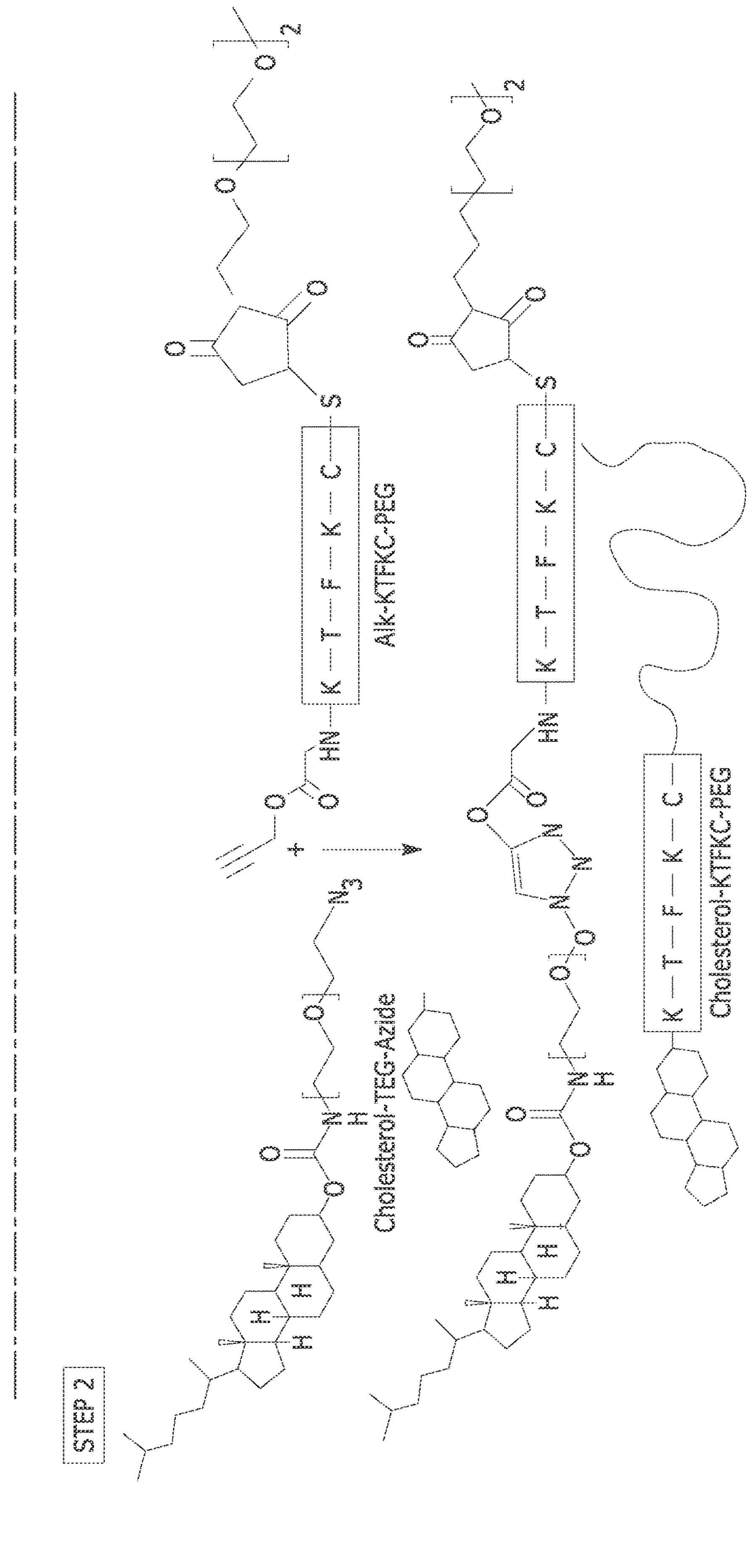
Figure 3B:
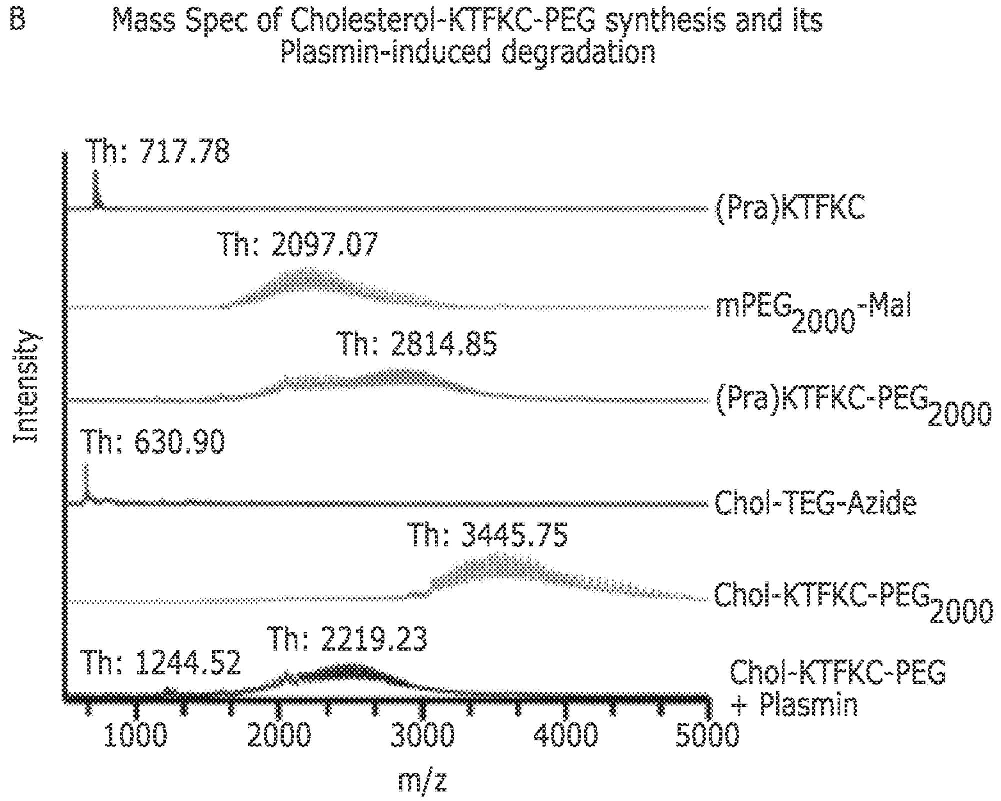
Figure 3C:
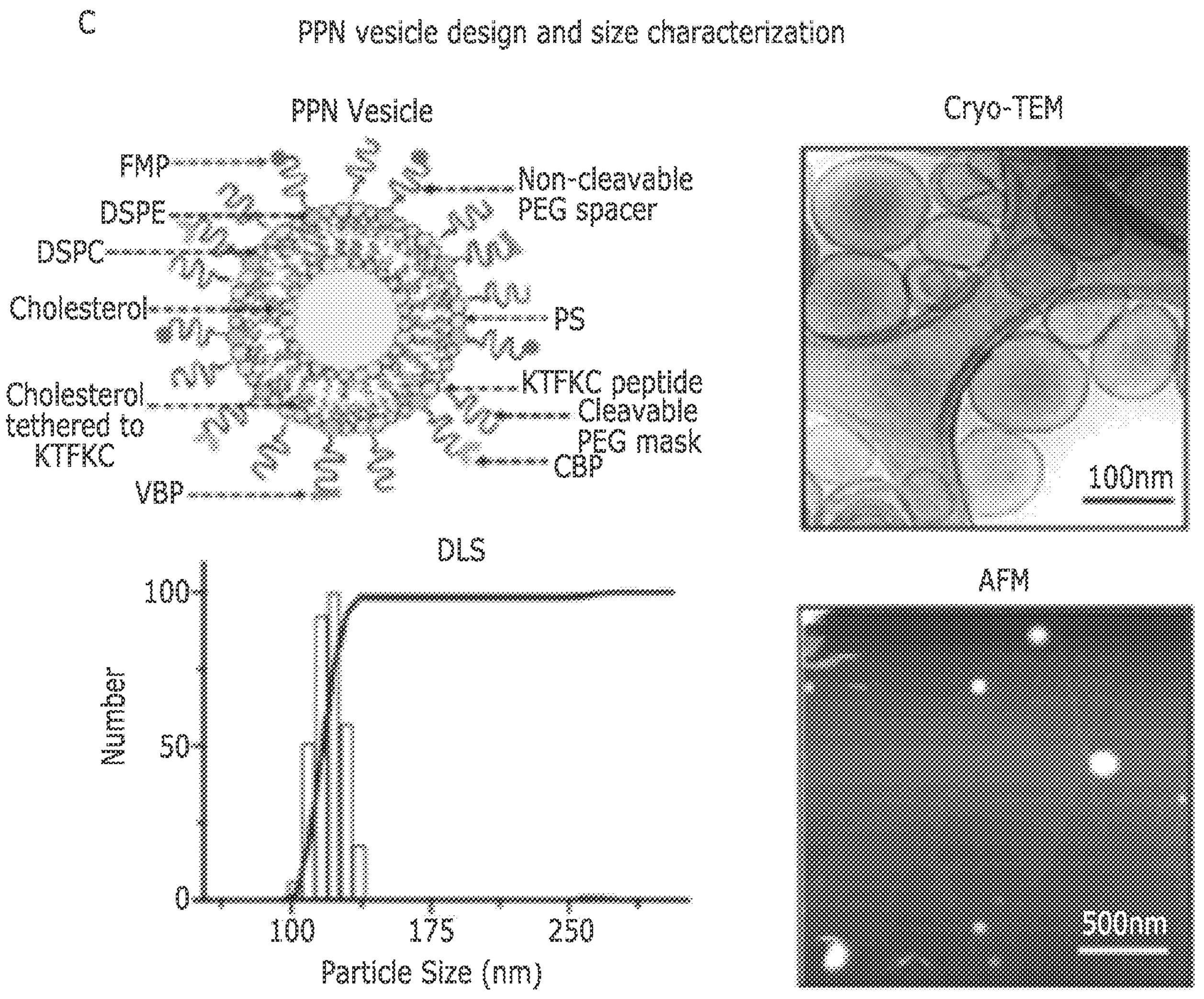
Figure 3D:
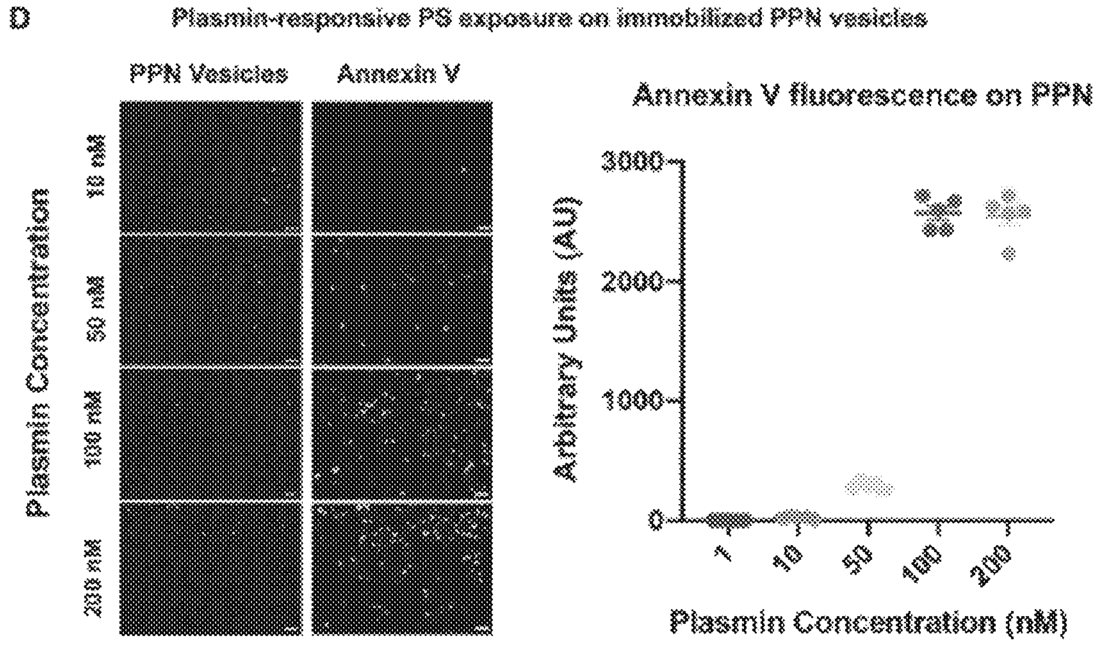

PPNs were manufactured by the thin film rehydration and extrusion technique through co-assembly of distearoylphosphatidylcholine (DSPC), distearoylphosphatidylethanolamine-$PEG_{2000}$-peptides, cholesterol, distearoylphosphatidylserine (DSPS) and Cholesterol-KTFKC (SEQ ID NO: 4)-$PEG_{2000}$ (FIG. 1). Here KTFKC (SEQ ID NO: 4) was a plasmin-cleavable peptide sequence. When needed, dihexadecanoylphosphoethanolamine Rhodamine B (DHPE-RhB) at 1 mol % was incorporated into the particles for fluorescent labeling. FIG. 3A shows the synthesis scheme for Cholesterol-KTFKC (SEQ ID NO: 4)-PEG; the mass spectrometry characterization of its synthesis and plasmin-triggered cleavage is shown in FIG. 3B. Size characterization of PPNs was conducted by cryo-transmission electron microscopy, atomic force microscopy and dynamic light scattering, which together indicated a PPN diameter of ~100-150 nm (FIG. 3C).

Figure 8:
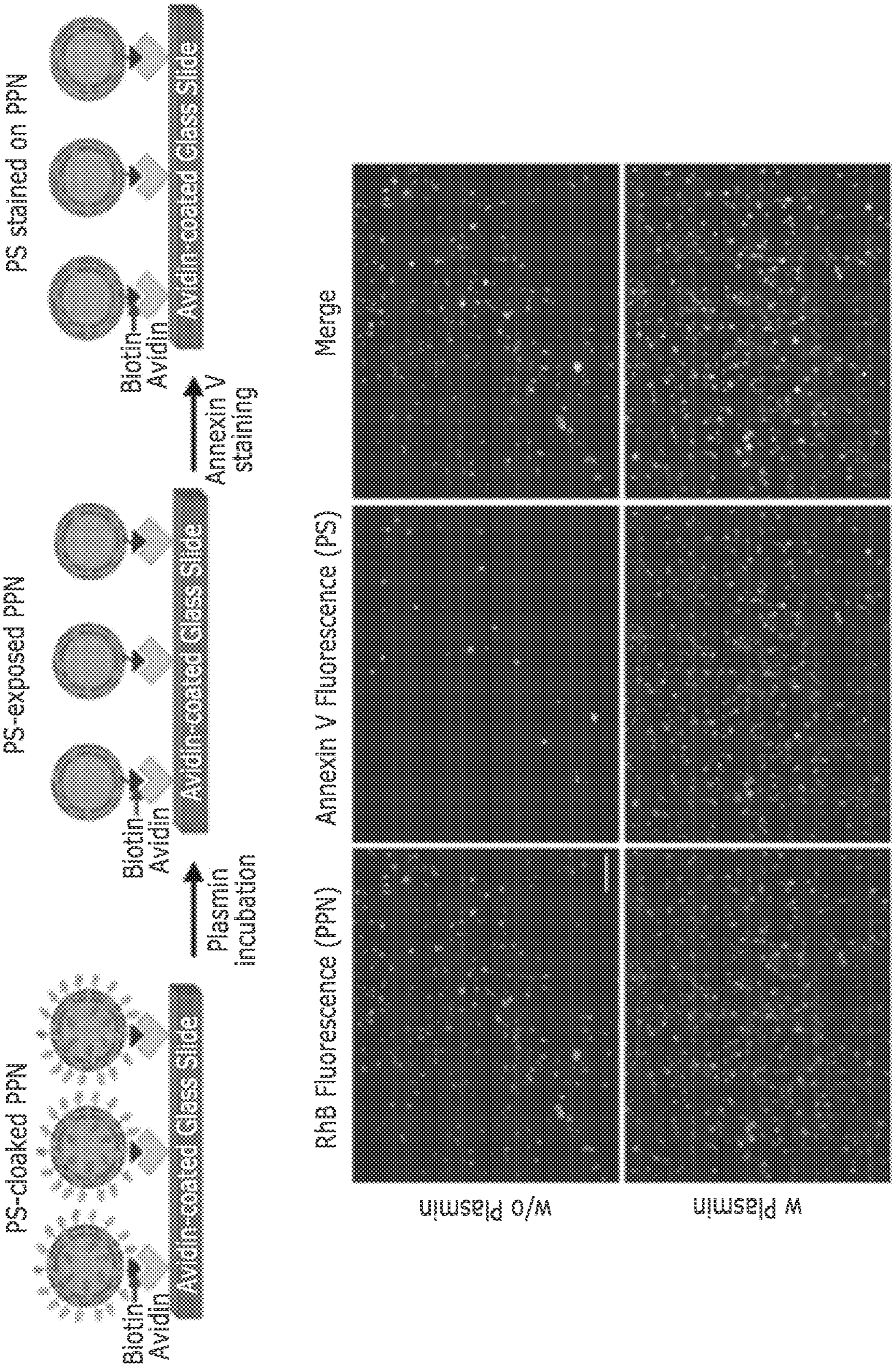
FIG. 8 illustrates images showing Annexin V fluorescence-based assessment of phosphatidylserine (PS) exposure on PPNs: Top panel shows experimental set-up. Bottom panel shows representative fluorescence images of immobilized PPNs (red RhB fluorescence) without (w/o) vs. with (w) plasmin (200 nM) incubation; w/o plasmin the green fluorescence of Annexin V staining the particles (yellow in merge) was minimal (i.e., minimal PS exposure), while w plasmin incubation the Annexin V staining was significant, indicating plasmin-triggered enhanced exposure of PS on PPNs.
Figure 9:
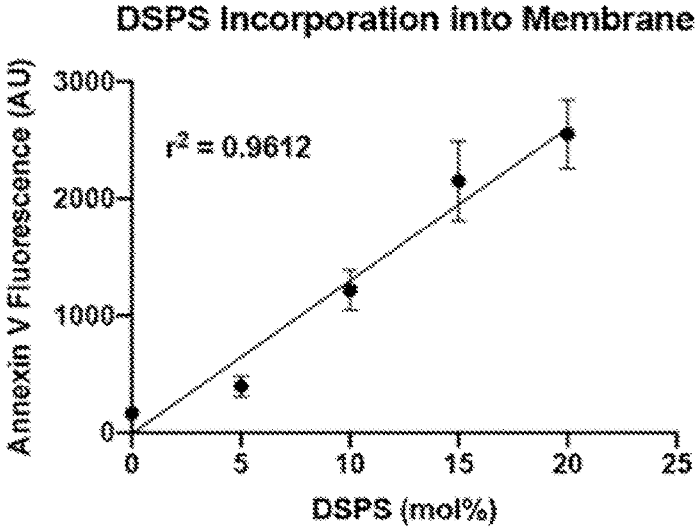
FIG. 9 illustrates plots illustrating Annexin V fluorescence with increasing incorporation of DSPS (5-20 mole %) in PPN.

Additional batches of DHPE-RhB-labeled PPNs were made to incorporate DSPE-PEG-Biotin (1 mol %), such that they could be immobilized on avidin-coated glass slides (FIG. 8). These immobilized PPNs were exposed to various concentrations of human plasmin (0-200 nM, 30 minutes) and then were incubated with fluorescent (AlexaFluor 647) Annexin V, which bound to exposed phosphatidylserine. The representative images and corresponding fluorescence analysis (FIG. 2D) showed that immobilized PPNs incubated with low (1 and 10 nM) concentrations of human plasmin had minimal Annexin V staining, whereas PPNs incubated with ≥50 nM human plasmin had increased Annexin V staining. Additional images are shown in FIG. 9. Annexin V fluorescence studies also established that phosphatidylserine could be efficiently incorporated into PPNs as the distearoylphosphatidylserine (DSPS) component of the liposomal membrane (FIG. 9).

Figure 3E:
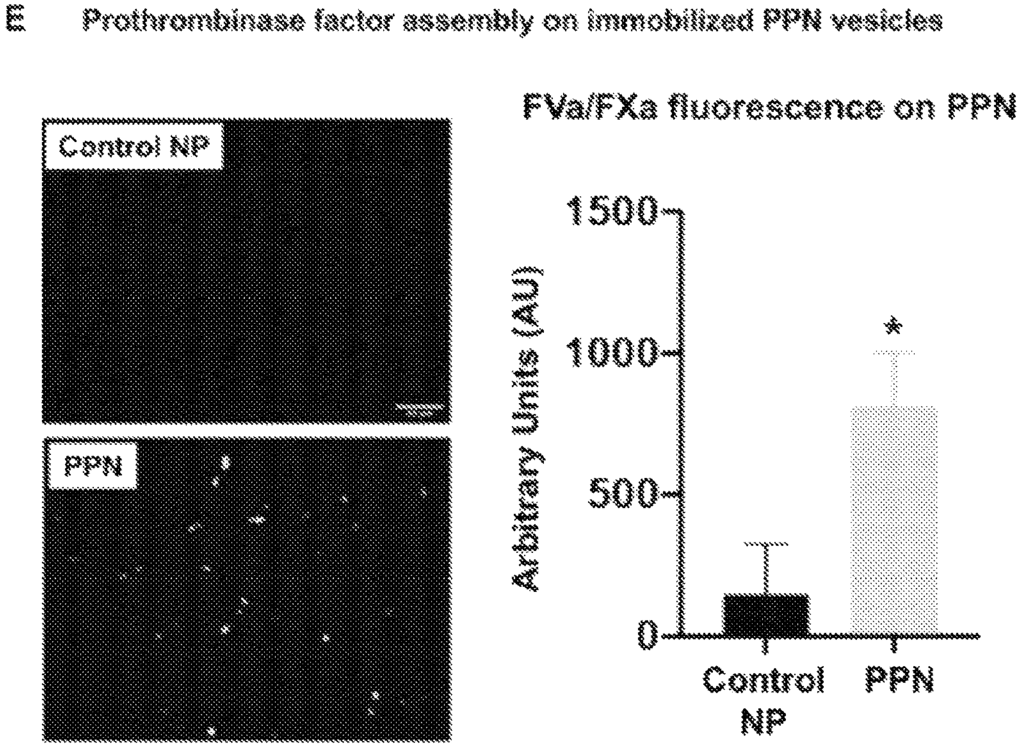

Next, biotinylated PPNs were immobilized on avidin-coated glass slides, exposed to human plasmin (200 nM, 30 minutes), and then were incubated with platelet-free human plasma to assess the ability of the exposed phosphatidylserine to render the assembly of FVa and FXa. Here, immobilized biotinylated liposomes containing all other lipid components of PPNs except DSPS and Cholesterol-KTFKC (SEQ ID NO: 4)-PEG (which ensured that there was no plasmin-triggered exposure of phosphatidylserine) were used as control nanoparticles. Plasmin-incubated PPNs showed greater ($p \leq 0.05$) FVa and FXa assembly compared to control nanoparticles (FIG. 3E).

PPNs Rescue Thrombin Generation and Improve Clot Formation In Vitro

Figure 4A:
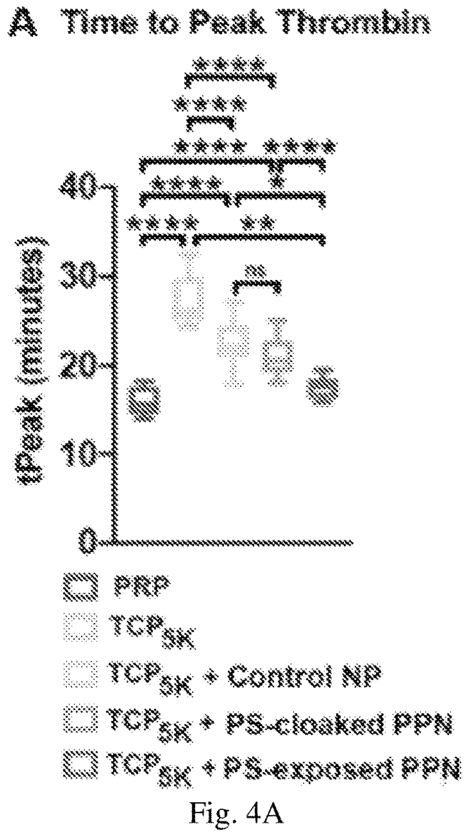
FIGS. 4(A-F) illustrate PPNs rescue thrombin generation and clot quality in platelet-depleted plasma. (A-D) Shown are thrombin generation studies in human thrombocytopenic plasma with <5000 platelets per μL ($TCP_{5K}$) compared to platelet rich human plasma. Time to peak thrombin (tPeak), thrombin lag time, peak thrombin generation and endogenous thrombin potential are shown after addition of control nanoparticles (Control NP) or PPNs with exposed phosphatidylserine (PS-exposed) or without exposed phosphatidylserine (PS-cloaked. (E) Rotational thromboelastometry analysis of whole human blood (WB) or whole human blood with <5000 platelets per μL (WB with 5K Plt) was conducted after addition of control nanoparticles (Control NP) or PPNs with exposed phosphatidylserine (PS-exposed), and clot formation time (CFT) and maximum clot firmness (MCF) were measured. (F) Shown are representative scanning electron microscopy images of fibrin clots generated in human thrombocytopenic plasma with <5000 platelets per μL ($TCP_{5K}$) compared to platelet rich human plasma (PRP) before and after the addition of PPNs with exposed phosphatidylserine (PS-exposed). Insets show a magnified view of the main image. *$p \leq 0.05$, $p \leq 0.01$, *$p \leq 0.001$ and ****$p \leq 0.0001$ (one way ANOVA with Tukey's multiple comparison test).
Figure 4B:
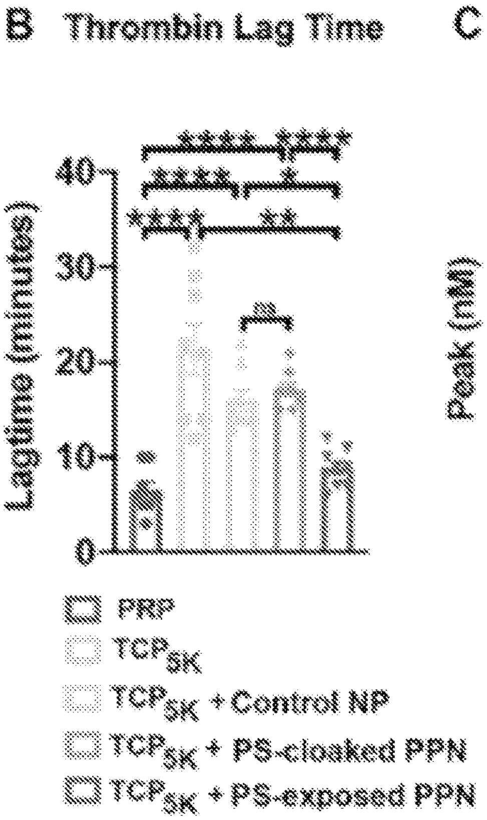
Figure 4C:
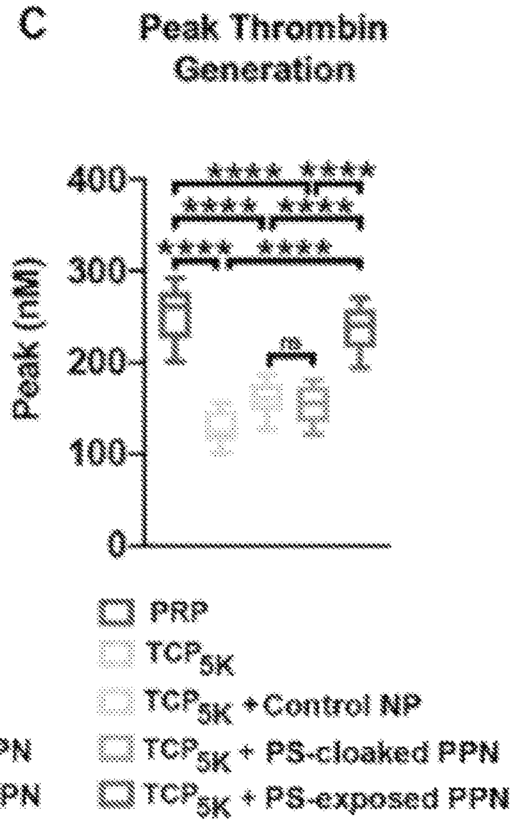
Figure 4D:
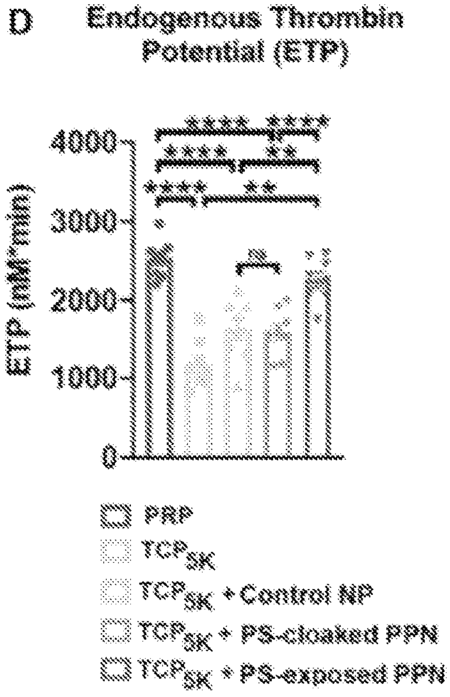
Figure 10:
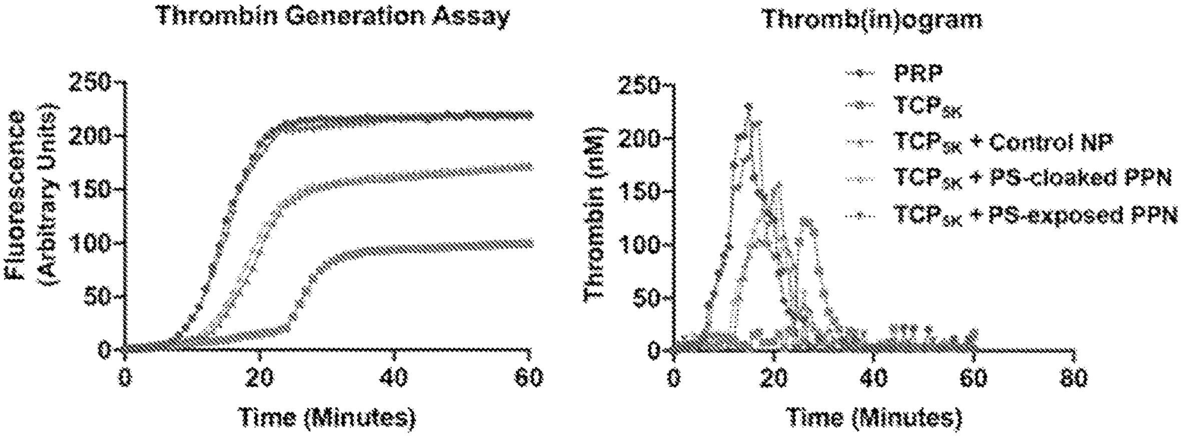
FIG. 10 illustrates graphs showing raw TGA fluorescence data and representative thromb(in)ograms for evaluating effect of Control NPs, PS-cloaked PPNs and PS-exposed PPNs on thrombin generation in $TCP_{5K}$ plasma.

Thrombin generation assays were performed with PPNs in the presence of platelet-depleted plasma and tissue factor (FIG. 4A-D). Platelet-rich plasma incubated with tissue factor was used as a positive control and was compared to platelet-depleted plasma containing only ~5000 platelets per μL (designated in FIG. 4 as thrombocytopenic plasma $TCP_{5K}$). Liposomes containing all other lipid components of PPNs except DSPS and Cholesterol-KTFKC (SEQ ID NO: 4)-PEG were used as control nanoparticles (Control NP in FIG. 4). Raw data from these studies are shown in FIG. 10. The time to reach peak thrombin (tPeak) was ~15 minutes for platelet-rich plasma and increased to ~30 minutes for thrombocytopenic plasma. Adding control nanoparticles in thrombocytopenic plasma only slightly reduced tPeak to ~25 minutes. Addition of DSPS-containing PPNs—where the phosphatidylserine on the surface was cloaked by Cholesterol-KTFKC (SEQ ID NO: 4)-PEG ('PS-cloaked PPN', FIG. 4)—to thrombocytopenic plasma showed effects similar to control nanoparticles. In contrast, addition of DSPS-containing PPNs with phosphatidylserine exposed at the surface ('PS-exposed PPN', FIG. 4) to thrombocytopenic plasma significantly reduced tPeak to values comparable to platelet-rich plasma ($p \leq 0.01$) (FIG. 4A). Correspondingly, the thrombin lag time in thrombocytopenic plasma was greater compared to platelet-rich plasma; addition of control nanoparticles or PS-cloaked PPNs only slightly shortened the thrombin lag time (FIG. 4B). In contrast, addition of PS-exposed PPNs significantly shortened the thrombin lag time comparable to that for platelet-rich plasma ($p \leq 0.01$) (FIG. 4B). Analyses of peak thrombin generation (FIG. 4C) and endogenous thrombin potential (FIG. 4D) showed that these characteristics of thrombin production were substantially reduced in thrombocytopenic plasma compared to platelet-rich plasma; addition of PS-exposed PPNs significantly rescued these parameters ($p \leq 0.01$).

Figure 11A:
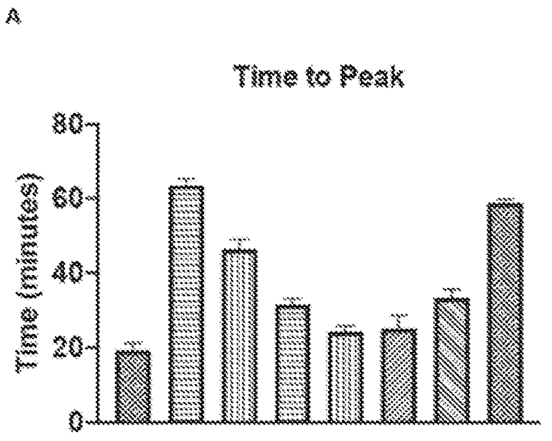
FIG. 11(A-B) illustrate plots showing A: Time to peak thrombin and B: Peak thrombin generation in $TCP_{5K}$ by PPN containing increasing mole % (5-20 mole %) of DSPS, compared to PRP (positive control), $TCP_{5K}$ with no particles (negative control) and direct 10 mole % equivalent DSPS addition (not incorporated in PPN vesicles). The thrombin kinetics are maximized at 10-15 mole % DSPS incorporated in PPN.
Figure 11B:
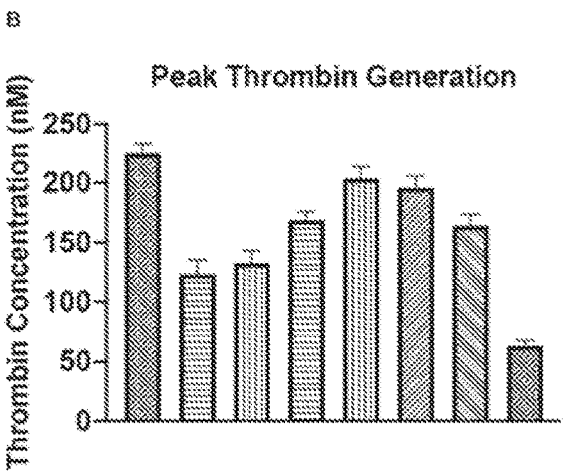
Figure 12:
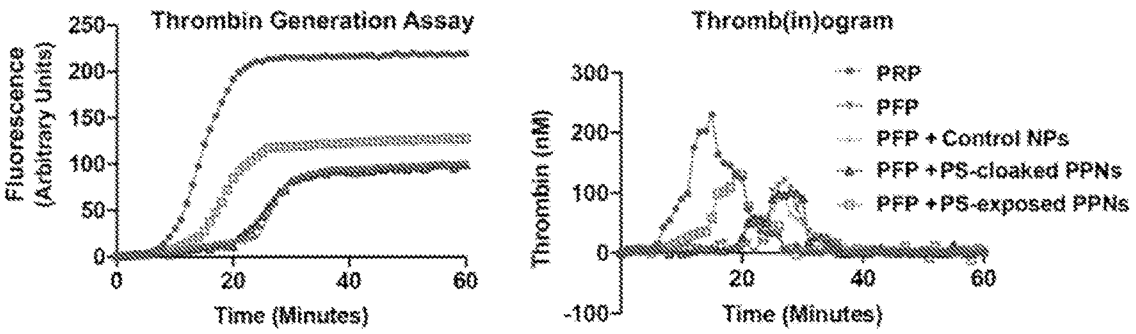
FIG. 12 illustrates raw fluorescence data and representative TGA thrombograms from studies evaluating effect of control nanoparticles (Control NPs), or PS-cloaked PPNs or PS-exposed PPNs on thrombin generation kinetics in platelet free plasma (PFP) shows that Control NPs and PS-cloaked PPNs are unable to rescue thrombin kinetics while PS-exposed PPNs are able to partly rescue thrombin kinetics in complete absence of platelets.
Figure 13:
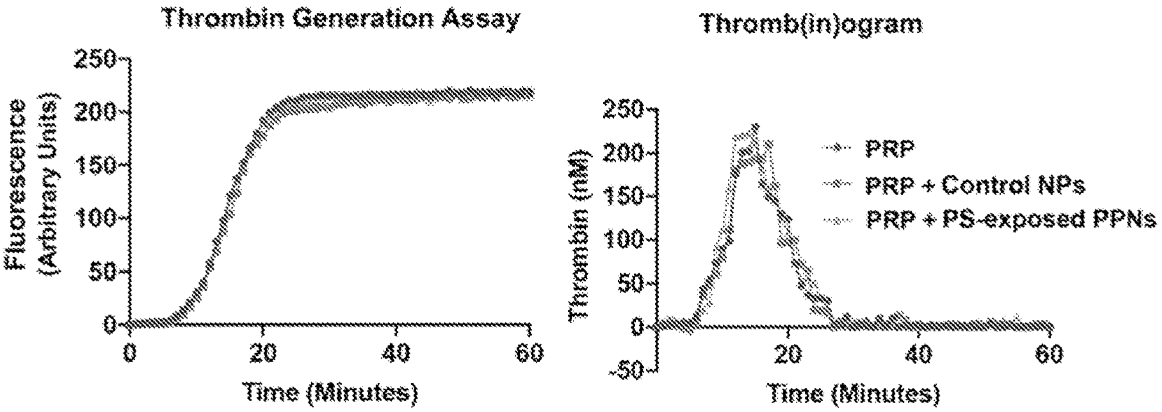
FIG. 13 illustrates raw fluorescence data and representative TGA thrombograms from studies evaluating effect of control nanoparticles (Control NPs) versus PS-exposed PPNs on thrombin generation in platelet rich plasma (PRP) shows that neither Control NPs nor PS-exposed PPNs can impart any additional amplification of thrombin kinetics in PRP. This is possibly because the prothrombinase assembly and thrombin generation capability is already saturated to the maximal extent in PRP by the available procoagulant surface of native platelets.

This procoagulant effect of PS-exposed PPNs reached a maximum at about 10-15 mole % DSPS incorporation and then started to decrease (FIG. 11A, B). Also, adding an equivalent amount of DSPS directly (not pre-assembled into PPNs) to plasma did not improve thrombin generation (FIG. 11A, B). Additional studies were carried out to test the effect of PS-exposed PPNs in platelet-free plasma (FIG. 12). Here, control nanoparticles or PS-cloaked PPNs could not restore thrombin generation, whereas PS-exposed PPNs partly rescued thrombin generation. When added to platelet-rich plasma, PS-exposed PPNs did not further increase thrombin output (FIG. 13).

Given that PS-exposed PPNs could rescue thrombin generation in thrombocytopenic plasma, we next tested whether this thrombin could increase fibrin formation and stability in thrombocytopenic human whole blood after addition of PS-exposed PPNs. For these studies, viscoelastic testing of clots using rotational thromboelastometry allowed temporal assessment of specific clot characteristics (FIG. 14A, B) including clot formation time and maximum clot firmness.

Figure 4E:
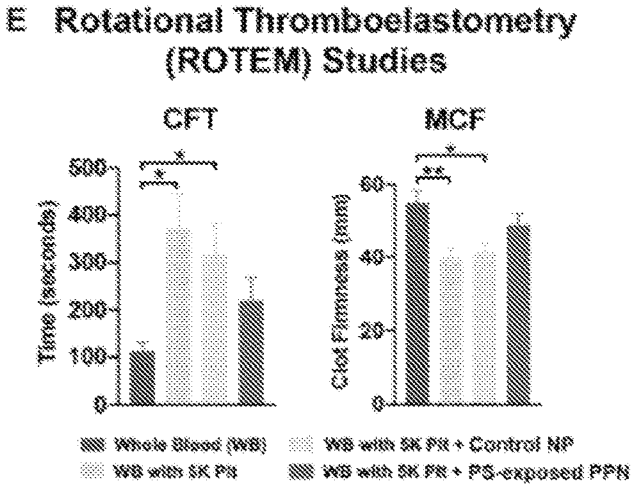
Figure 4F:
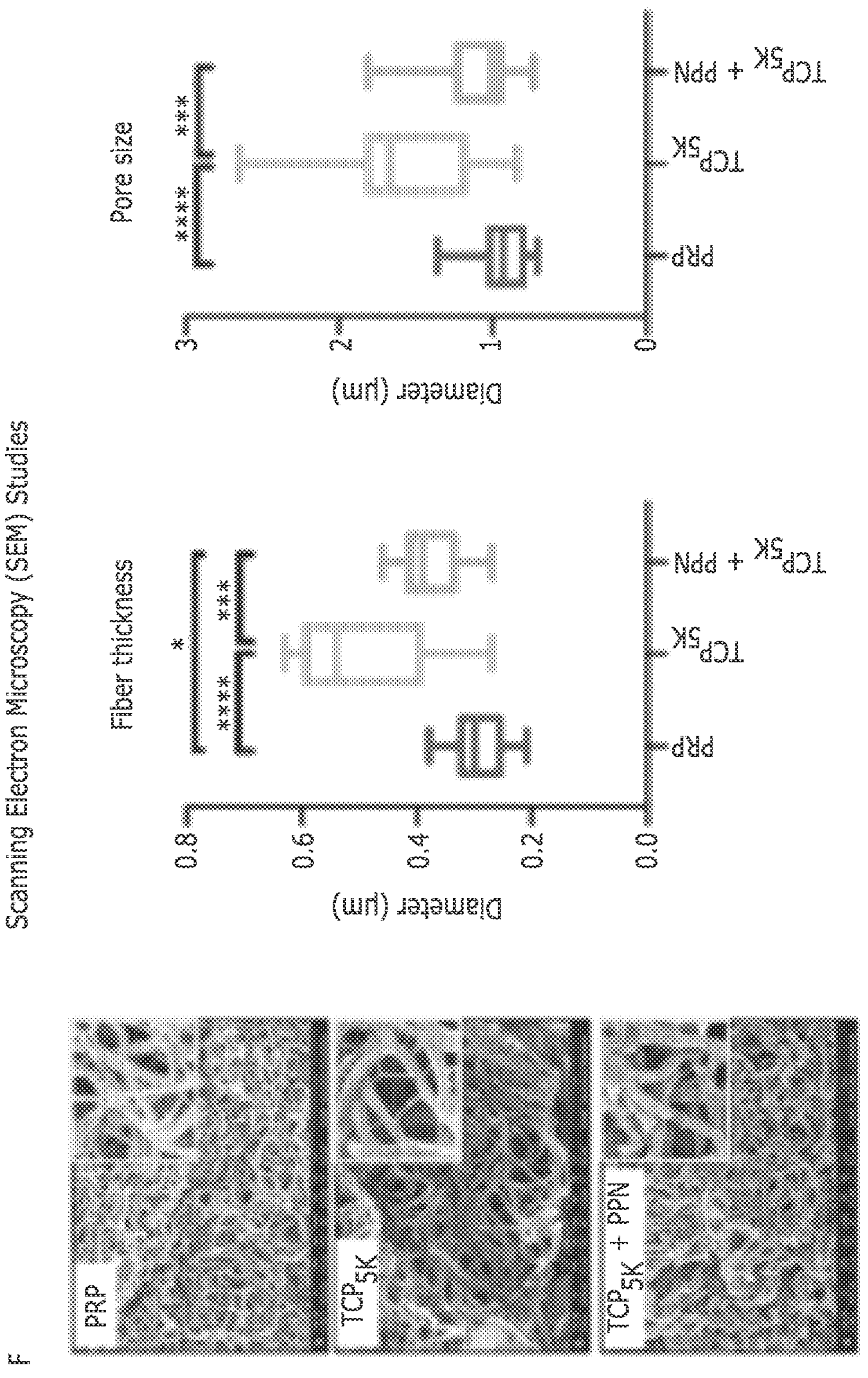

Compared to healthy human whole blood (no platelet depletion, control), blood with only 5000 platelets per μL showed delayed (increased) clot formation time and reduced maximum clot firmness. Adding PS-exposed PPNs improved both parameters to values closer to those for healthy human whole blood (FIG. 4E and FIG. 14). Scanning electron microscopy analysis of fibrin formed from platelet-rich plasma, thrombocytopenic plasma alone and thrombocytopenic plasma treated with PS-exposed PPNs was conducted to assess fibrin thickness and porosity. Addition of PS-exposed PPNs enhanced fibrin fiber morphology and density in thrombocytopenic plasma (FIG. 4F).

PPNs Increase Fibrin Generation and Reduce Clot Lysis

Figure 5A:
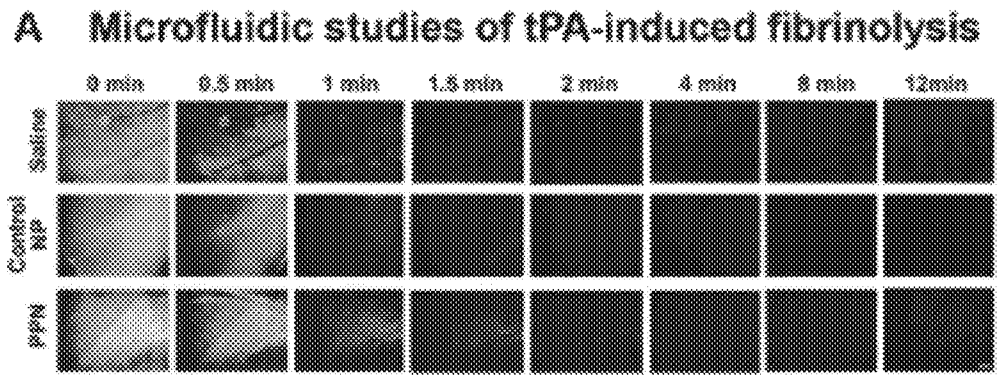
FIGS. 5(A-F) illustrate PPNs enhance human plasma clot stability under fibrinolytic conditions. (A-C) Shown is microfluidic analysis of human plasma clots exposed to tissue plasminogen activator (tPA) to create a fibrinolytic environment. Addition of PPNs that exposed phosphatidylserine in situ in response to plasmin (PPN) delayed clot lysis as indicated by fibrin green fluorescence (A,B) and reduced D-dimers in the clot lysate (C) compared to control nanoparticles (Control-NP). (D-F) Shown is rotational thromboelastometry analysis of whole human blood (WB) in the presence of tPA. Addition of PPNs that exposed phosphatidylserine in situ in response to plasmin (PPN) enhanced clot stability as demonstrated by the maximum clot firmness (MCF) maintenance time (E) and maximum lysis (ML as % of MCF) (F). *p≤0.05, p≤0.01, and *p≤0.001 (two way ANOVA with Tukey's multiple comparison for microfluidic data and one way ANOVA with Tukey's multiple comparison for ROTEM data).
Figure 5B:
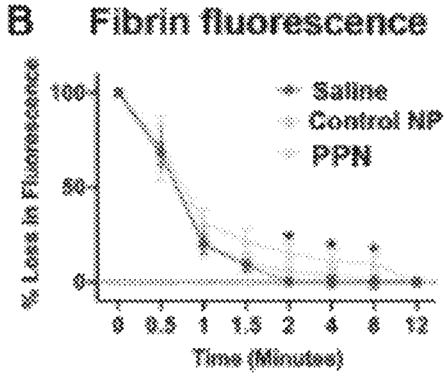
Figure 5C:
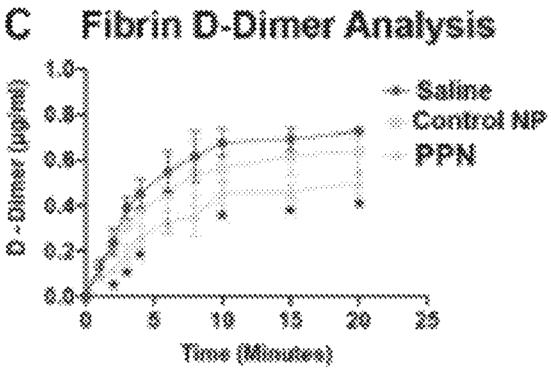
Figure 5D:
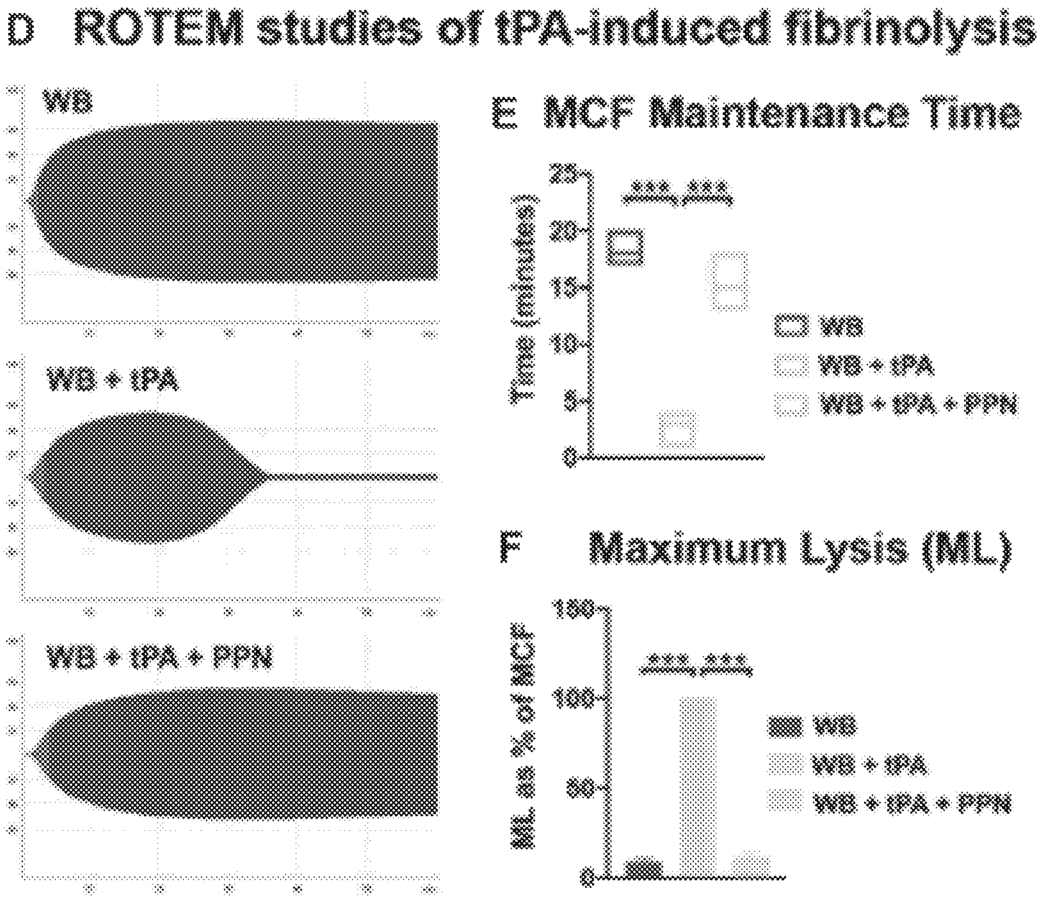
Figure 15:
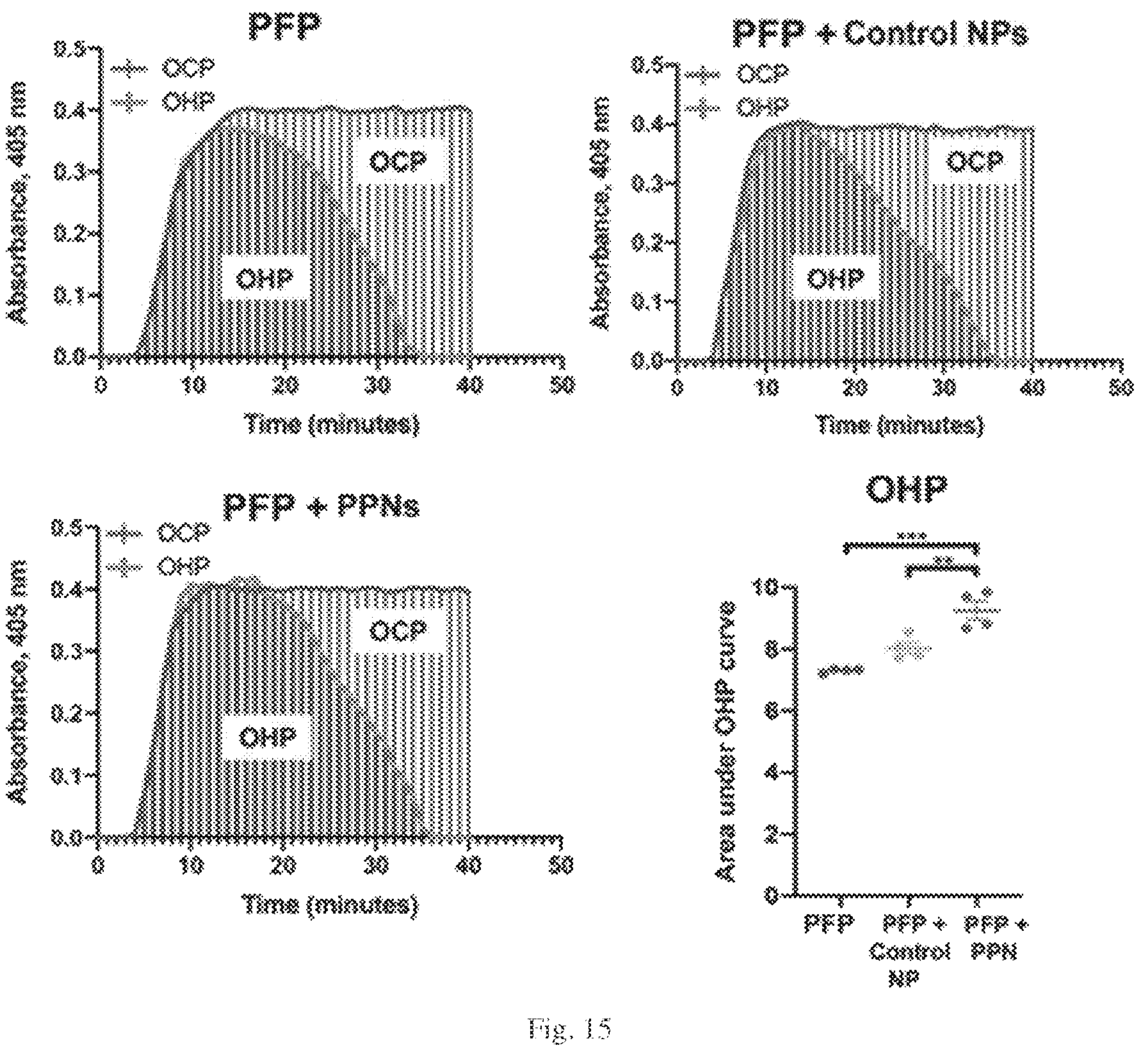
FIG. 15 illustrates overall hemostatic potential (OHP) assay raw data and quantitative analysis indicate that addition of PPN to PFP enhances fibrin; this can be rationalized by considering that tPA (hence in situ generated plasmin) can cleave the PEG cloak to expose PS on PPNs, which can then amplify thrombin generation in situ, and this thrombin can then convert fibrinogen to fibrin de novo.
Figure 16:
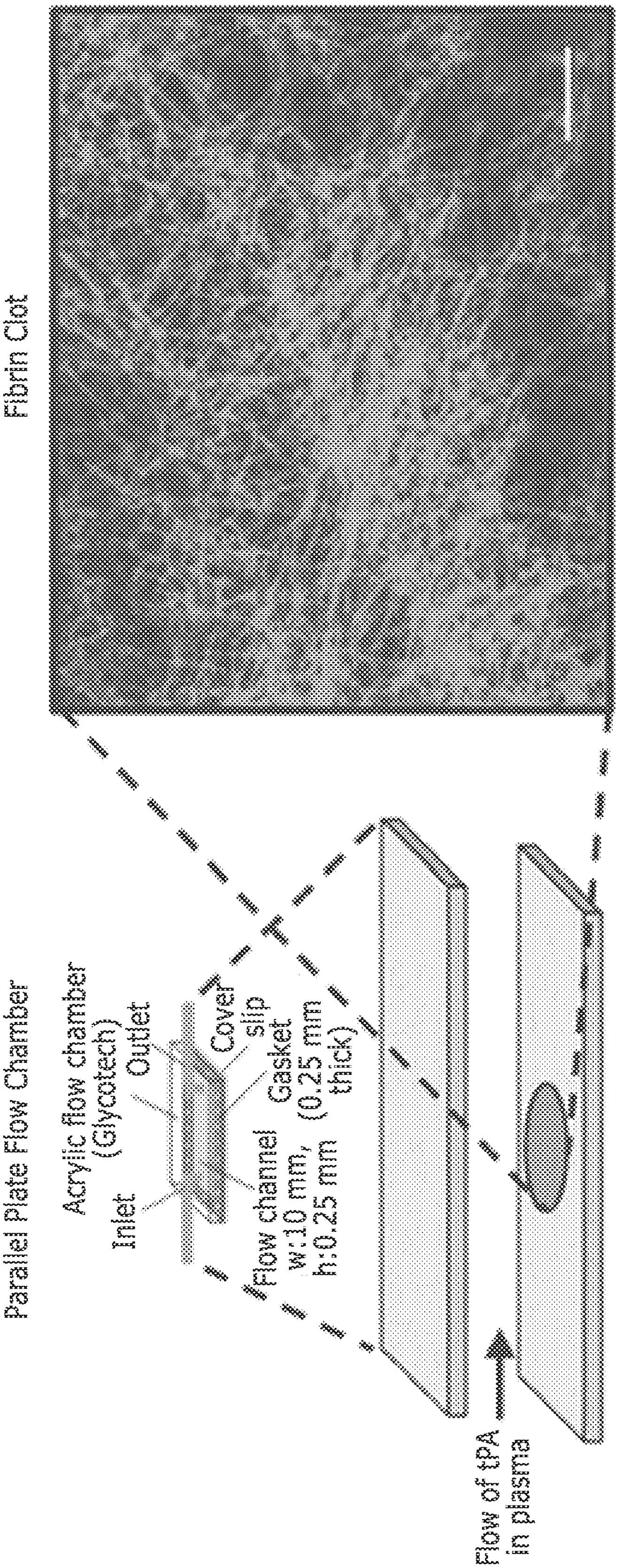
FIG. 16 illustrates experimental set-up and representative high resolution confocal fluorescence image of fibrin clot for the tPA-induced fibrinolysis studies in the parallel plate microfluidic chamber.
Figure 17:
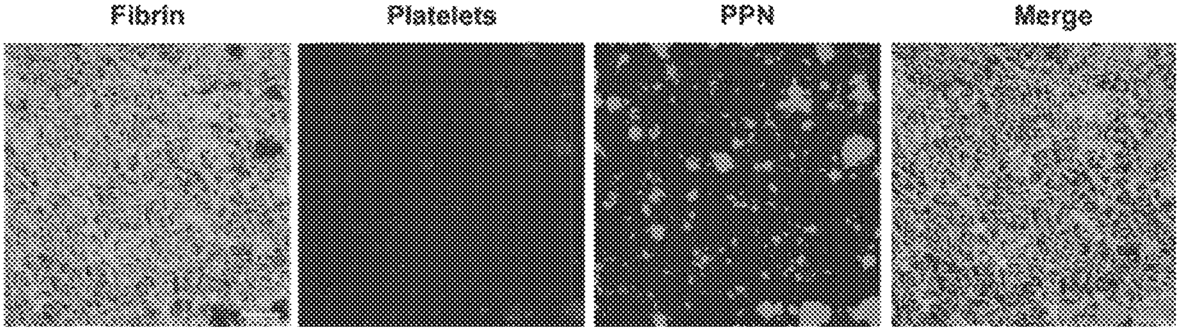
FIG. 17 illustrates representative high resolution confocal fluorescence images of clots formed from platelet-rich plasma containing fluorescent fibrinogen and calcein-stained platelets and exposed to flow of Rhodamine B (RhB)-labeled PPN vesicles show that PPNs can efficiently incorporate within clots; the high co-localization of PPNs with platelets further suggest that PPNs bind to activated platelets possibly via FMP binding to integrin $\alpha_{IIb}\beta_3$ and VBP binding to vWF on active platelets; additionally, since the clots were formed on collagen-coated glass slides, PPNs can also directly bind to collagen (via CBP) and co-localize with platelets binding to the same collagen.
Figure 18:
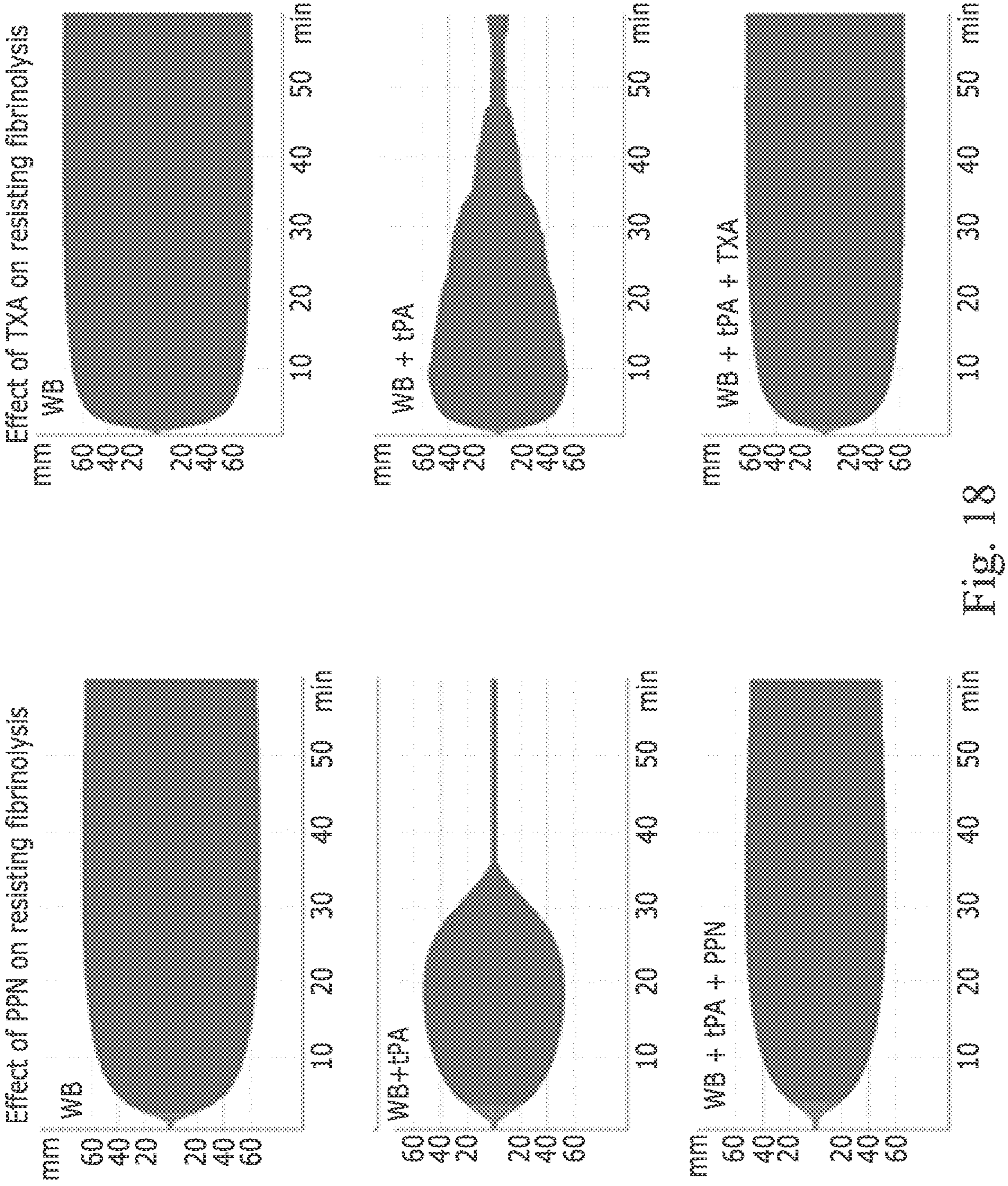
FIG. 18 illustrates representative ROTEM results showing the effect of PPN on resisting lysis in tPA-spiked whole blood (WB) compared to the effect of tranexamic acid (TXA) on similar WB samples; Plasmin generated in situ from tPA can cleave the PEG cloak on PPNs to expose PS, that can amplify thrombin and thereby generate fibrin de novo (supported by fibrin morphology SEM data in FIG. 3C and OHP data in FIG. S12); On the other hand, TXA is an inhibitor tPA and plasmin activity and thus prevents fibrinolysis; Therefore considering the fibrin generation vs. fibrinolysis reaction to be represented simply as 'Thrombin+Fibrinogen→Fibrin' and 'Fibrin+Plasmin→Fibrinolysis', it can be rationalized that the lysis resistance effect of PPN is possibly via replenishment of fibrin and may also be partly due to competitive consumption of plasmin.
Figure 19:
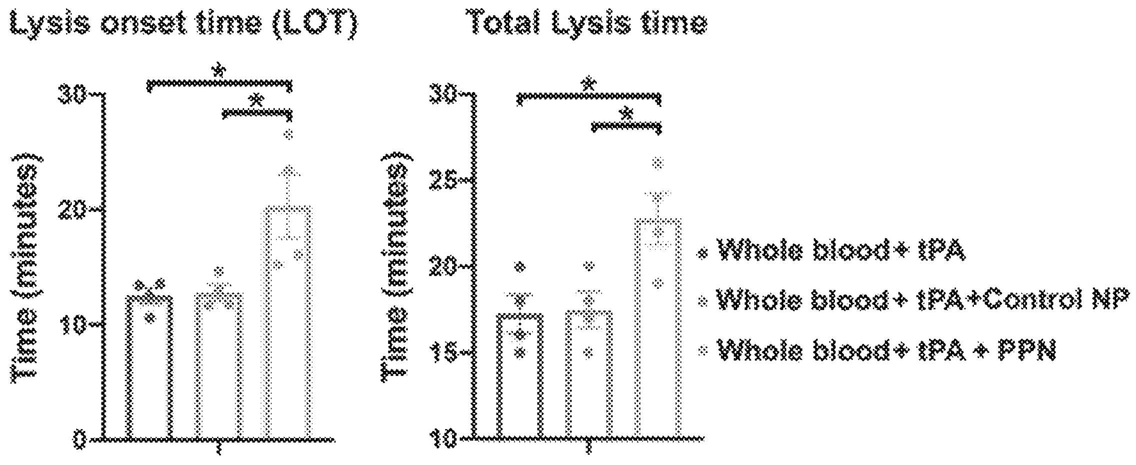
FIG. 19 illustrates the effect of PPNs on improving clot stabilization (delaying clot lysis) under highly lytic environment induced by high dose of tPA added to whole blood to generate high amount of plasmin; Compared to treatment with control nanoparticles (Control NP), treatment with PPN delays lysis onset time (LOT) and prolongs Total Lysis Time as analyzed by ROTEM.

We first used the overall hemostatic potential assay in platelet-free plasma in the presence of tissue plasminogen activator (tPA) to measure the generation and degradation kinetics of fibrin when plasma was treated with PS-cloaked PPNs. Here, the in situ generation of plasmin by tPA was expected to cleave off the PEG from the Cholesterol-KTFKC (SEQ ID NO: 4)-$PEG_{2000}$ cloak to expose phosphatidylserine at the PPN surface. The assay results showed a balance between fibrin generation and fibrin degradation that was not affected by addition of control nanoparticles (FIG. 15). However, addition of PPNs increased overall hemostatic potential, indicating increased fibrin generation (FIG. 15). We next used an in vitro microfluidic set-up with human plasma clots exposed to tPA (FIG. 16) to evaluate the effect of PPNs on fibrin in a fibrinolytic environment. Addition of PS-cloaked PPNs resulted in a significant delay in fibrinolysis compared to addition of control nanoparticles that lacked a phosphatidylserine component or saline ($p \leq 0.05$) (FIG. 5A, B). PPNs were found to be incorporated effectively into clots by co-localizing with activated platelets (FIG. 17). The ability of PPNs to reduce clot lysis was further corroborated by the observation that the PPN-treated plasma showed decreased fibrin D-dimer values (FIG. 5C). Parallel thromboelastometry studies were carried out with tPA added to human whole blood with or without the addition of PPNs. Addition of tPA significantly reduced maximum clot firmness and increased maximum lysis within 30 minutes, without affecting clot formation time, indicating increased fibrinolysis ($p \leq 0.001$) (FIG. 5D). We next assessed maximum clot firmness maintenance time as a measure of clot stability. Treatment with PPNs significantly improved maximum clot firmness maintenance time and reduced fibrinolysis ($p \leq 0.001$) (FIGS. 5E and 5F). Comparable results were observed when tranexamic acid (a direct plasmin inhibitor) was added to tPA-treated whole human blood (FIG. 18). Treatment with PPNs delayed, but did not eliminate, clot lysis even when a higher tPA dose was added to whole human blood (FIG. 19).

PPNs Reduce Bleeding in Thrombocytopenic Mice

Figure 20:
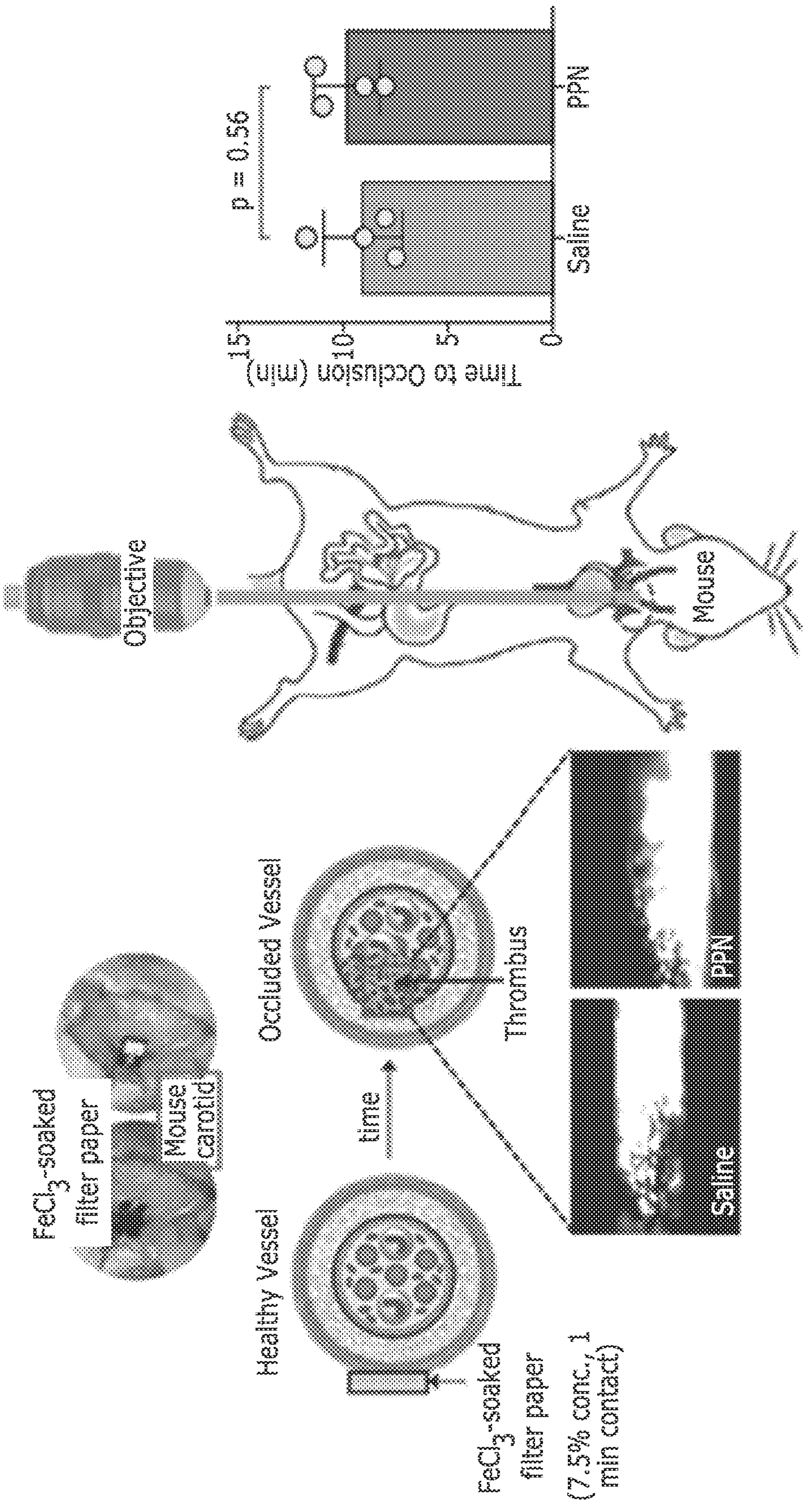
FIG. 20 illustrates experimental schematic of $FeCl_3$-induced carotid artery thrombosis model in C57BL6/J mouse and representative intravital microscopy images of artery occlusion in saline-treated versus PPN-treated animals. Time-to-occlusion of the artery is monitored, and this data is reflective of thrombotic risk of 'administered agent'. As evident from the quantitative data, both saline-treated (control) and PPN-treated animals showed full occlusion at ~10-11 min, with no significant statistical difference between them, indicating that PPNs themselves do not pose a thrombotic risk.
Figure 21:
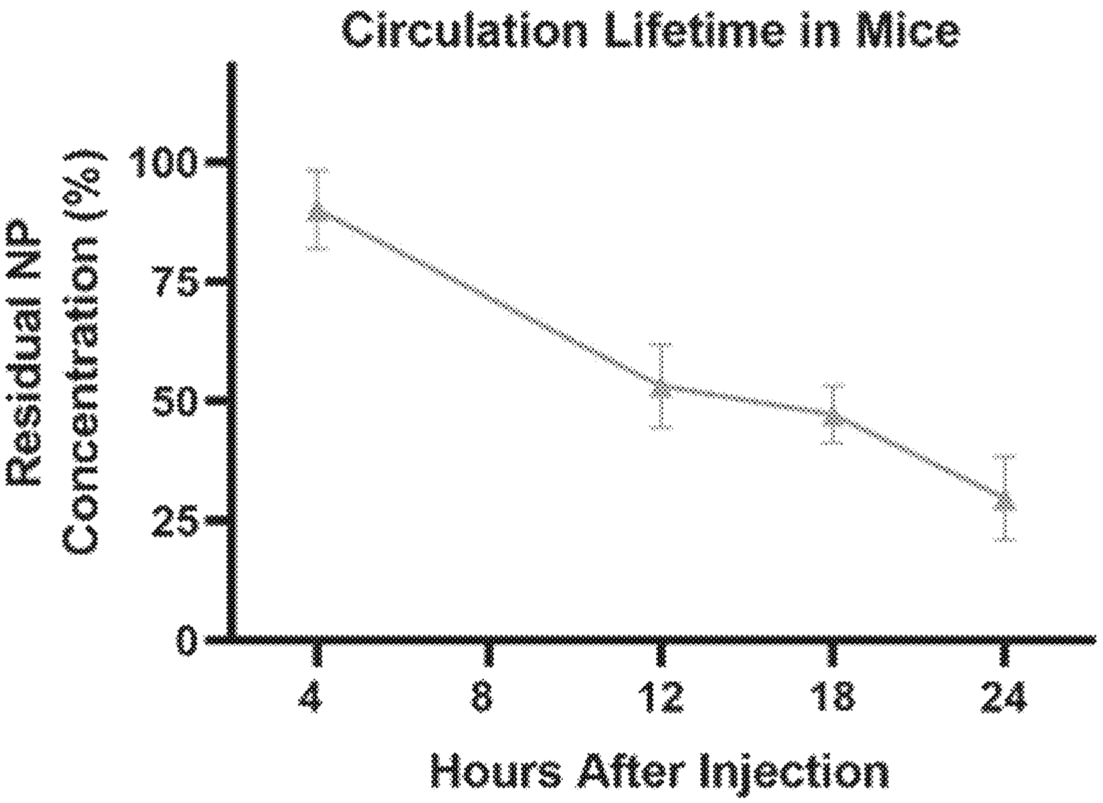
FIG. 21 illustrates circulation lifetime analysis via post tail-vein injection and retroorbital blood draw in mice, with spectrometric measurement of nanoparticle-associated RhB fluorescence against a RhB-labeled liposome concentration vs. fluorescence calibration curve indicates a circulation half-life ~12 hours for the PPN.

All in vivo studies were conducted using PS-cloaked PPNs with the rationale that injury site localized plasmin would cleave off the PEG from the Cholesterol-KTFKC (SEQ ID NO: 4)-$PEG_{2000}$ cloak to expose phosphatidylserine at the surface of PPNs. Prior to evaluating hemostatic efficacy of PPNs in vivo, we first assessed whether these nanoparticles carried an inherent risk of thrombosis. This was evaluated in a $FeCl_3$-induced arterial thrombosis model in mice where the time-to-occlusion of the carotid artery in the presence or absence of PPNs was compared. PPN administration did not accelerate time-to-occlusion of the carotid artery compared to saline administration (FIG. 20), indicating that the PPNs were not inherently pro-thrombotic. The circulation half-life of PPNs in mice, evaluated by administering Rhodamine-B labeled PPNs through tail-vein injection and collecting blood over 24 hours to analyze PPN-associated fluorescence, indicated a circulation half-life of ~12 hours (FIG. 21).

Figure 6A:
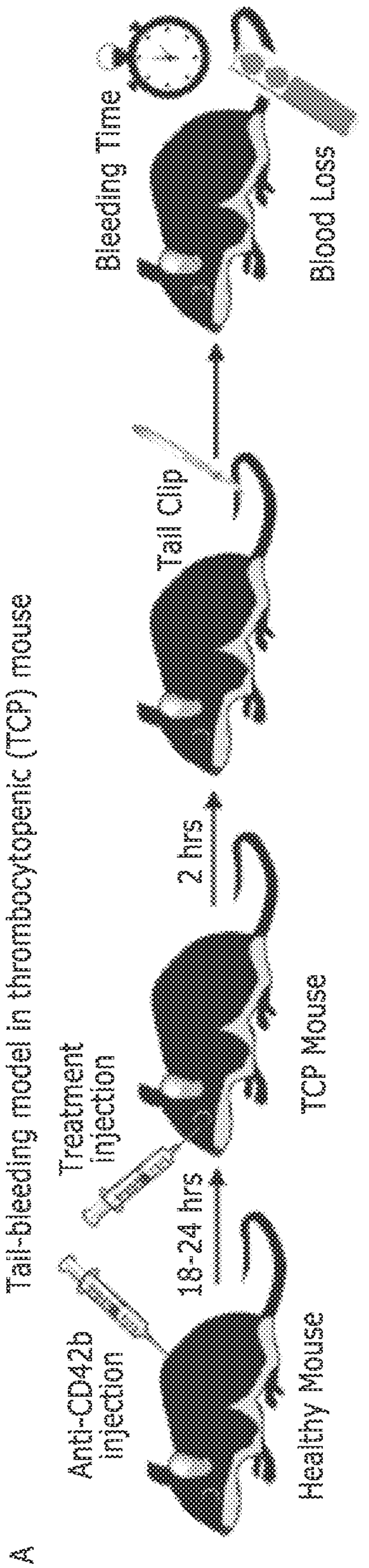
FIGS. 6(A-D) illustrate PPNs reduce tail bleeding in thrombocytopenic mice. (A) In the tail transection bleeding mouse model, mice were rendered thrombocytopenic through intraperitoneal injection of anti-CD42b (anti-GPIb) antibody (0.5 μg/kg) to deplete platelets. ~18-24 hours later, mice were administered by retro-orbital injection either control nanoparticles (Control NP) or PPNs. Two hours after treatment, mouse tails were clipped 1 mm from the tip and bleeding time and blood loss were measured. (B) Shown are platelet counts in normal (wildtype) mice and antibody-treated thrombocytopenic mice. (C) Shown are bleeding times in normal (wildtype) mice and antibody-treated thrombocytopenic (TCP) mice before and after addition of control nanoparticles or PPNs. Also shown are bleeding times when mice were transfused with syngeneic platelets. (D) Shown is blood loss analysis using a hemoglobin assay in normal (wildtype) mice and antibody-treated thrombocytopenic (TCP) mice before and after addition of control nanoparticles or PPNs. Also shown is blood loss when mice were transfused with syngeneic platelets. n=6 animals per group. *p≤0.05, p≤0.01, and *p≤0.001 (one way ANOVA with Tukey's multiple comparison test).
Figure 6B:
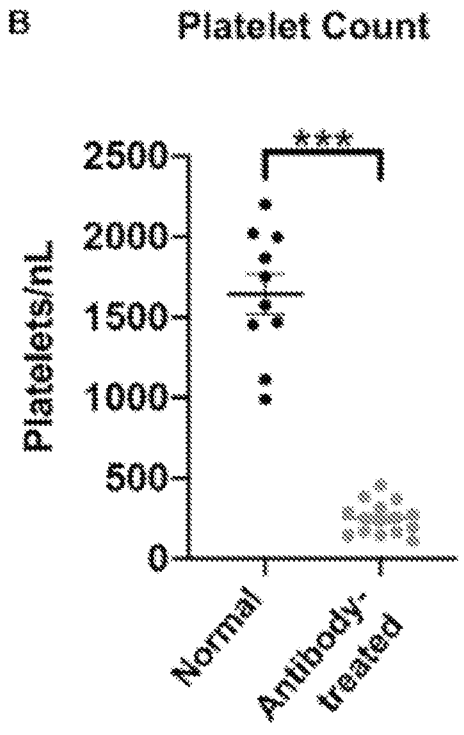

The hemostatic efficacy of PPNs was next evaluated in the tail-transection bleeding mouse model in mice that were rendered thrombocytopenic by administration of anti-CD42b (anti-GPIb) antibody (FIG. 6A). For these experiments, the antibody dose (0.5 μg/kg) reduced the platelet count by approximately 80% at 18-24 hours after antibody administration (platelet count reduced from ~1500/nl to ~250/nl) (FIG. 5B). Platelet recovery started at around 36-48 hours after antibody administration. The extent of the platelet count reduction was within the range of clinical thrombocytopenia in humans. Control nanoparticles (liposomes containing all other lipid and lipid-peptide components but not DSPS or Cholesterol-KTFKC (SEQ ID NO: 4)-PEG) or PPNs were administered at a dose of 2 mg/kg. Additional comparisons were done with syngeneic mouse platelets (250/nl dose).

Figure 6C:
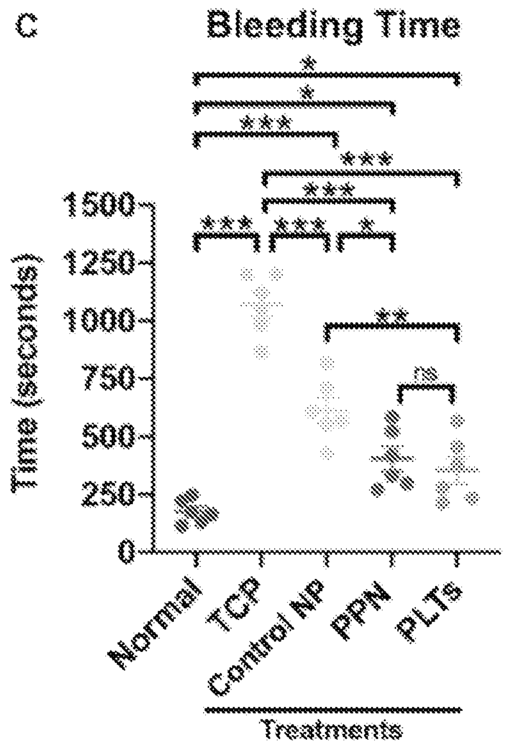
Figure 6D:
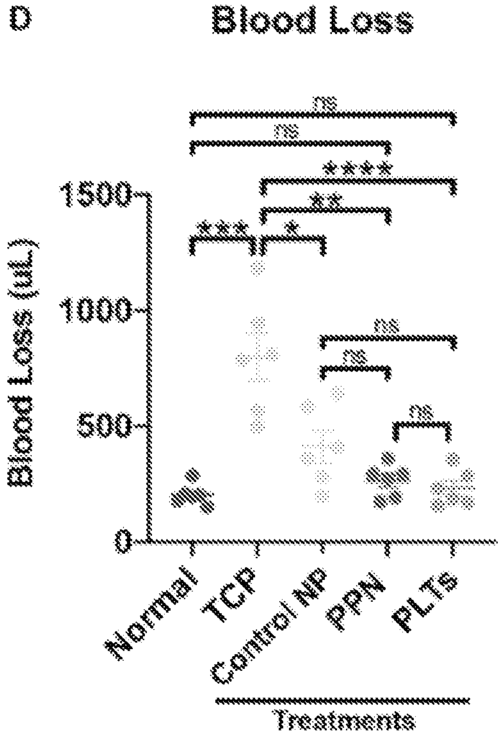
Figure 22:
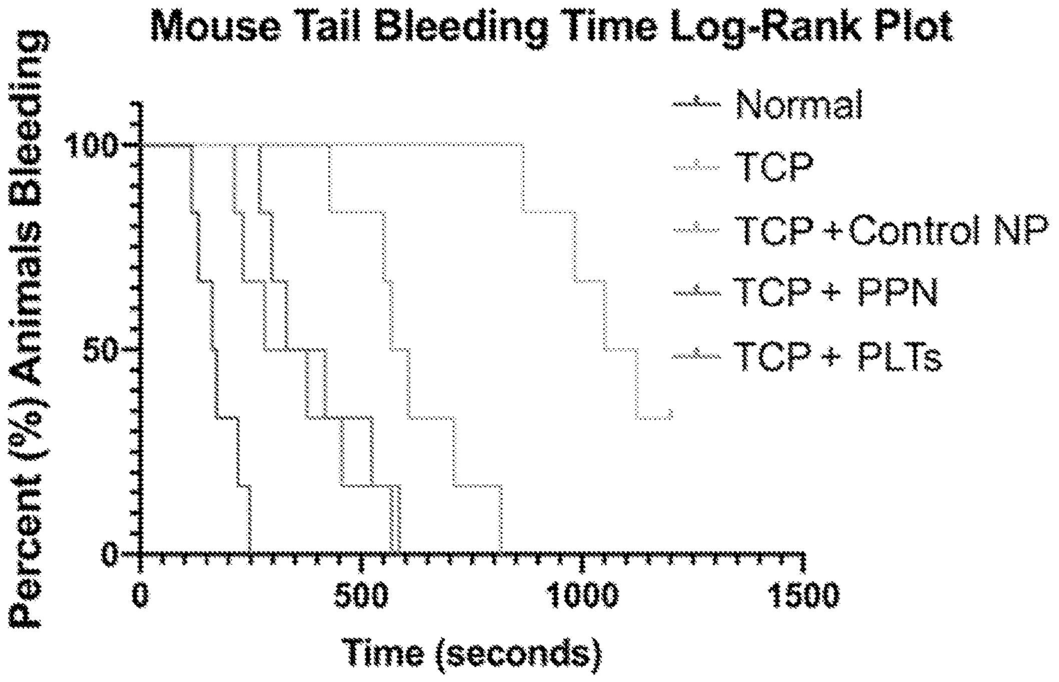
FIG. 22 illustrates mouse tail-bleeding time as Log-Rank plot for various treatment groups, showing that induction of thrombocytopenia (TCP) results in substantial increase of bleeding time compared to normal; Treatment with control nanoparticles (Control NP) resulted in partial reduction of bleeding time; Treatment with PPNs results in further reduction of bleeding time, comparable to treatment with syngeneic platelets. Note, Control NPs here is the original platelet surrogate (SynthoPlate).

After transection of tails of normal control (wildtype) or thrombocytopenic mice, bleeding times were monitored (FIG. 6C and FIG. 22). Bleeding stopped at 175.67±51.4 seconds in normal mice but at 1071±130.8 seconds in thrombocytopenic mice (FIG. 6C). Treating the thrombocytopenic mice with retro-orbitally injected control nanoparticles 2 hours prior to tail transection, reduced the bleeding time to 613.3±134.9 seconds (FIG. 6C). Treatment with PPNs reduced the bleeding time even further to 404.5±127.9 seconds ($p \leq 0.001$) (FIG. 6C). When thrombocytopenic mice were treated with syngeneic platelets, the bleeding time was reduced to 355±131.4 seconds (FIG. 6C). Blood loss analysis by spectrophotometric assessment of hemoglobin demonstrated that treatment with PPNs reduced blood loss from clipped tails in thrombocytopenic mice (FIG. 6D) in a manner comparable to treatment with syngeneic platelets.

PPNs Enhance Hemostasis and Survival in Rodent Traumatic Hemorrhage Models

Figure 7A:
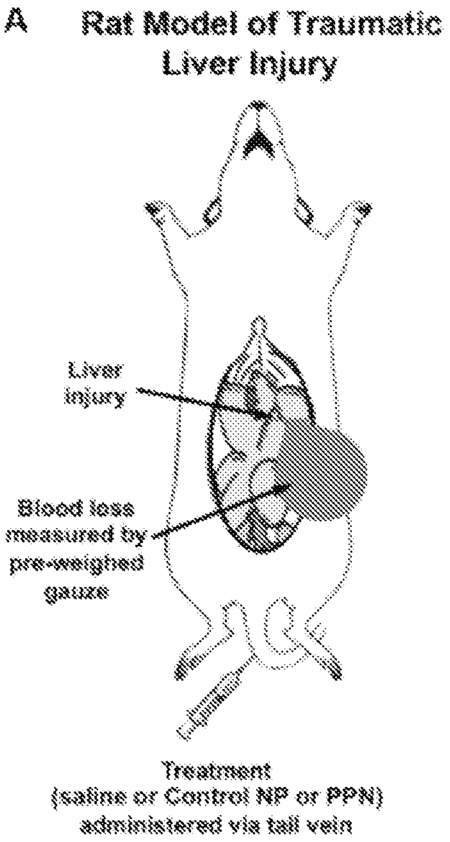
FIGS. 7(A-E) illustrate PPNs reduce blood loss and improve survival in rats with hemorrhagic liver injury. (A) In the rat liver injury hemorrhagic model, >30% of the liver was resected to cause intraperitoneal hemorrhage and treatment after injury was administered via tail vein. (B) Shown is blood loss at one hour after treatment with PPNs compared to control nanoparticles (Control NP) or saline. (C) Shown is animal survival 3 hours after treatment with PPNs compared to control nanoparticles (Control NP) or saline. (D) Shown are representative immunofluorescence images of the liver injury site indicating greater fibrin fluorescence in hemostatic clots after PPN treatment compared to either control nanoparticles (Control NP) or saline. (E) Shown is Carstairs' staining of representative hemostatic clots at the liver injury site indicating higher fibrin content (orange red staining) in the clots of PPN-treated rats compared to Control NP- or saline-treated rats. n=5 animals per group. *p≤0.05, p≤0.01, and *p≤0.001 (one way ANOVA with Tukey's multiple comparison test).
Figure 7B:
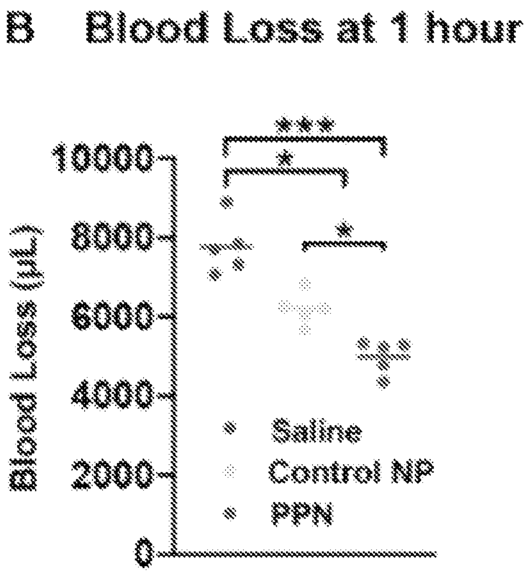
Figure 7C:
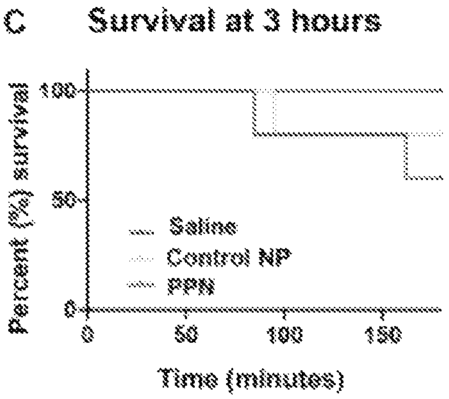
Figure 7D:
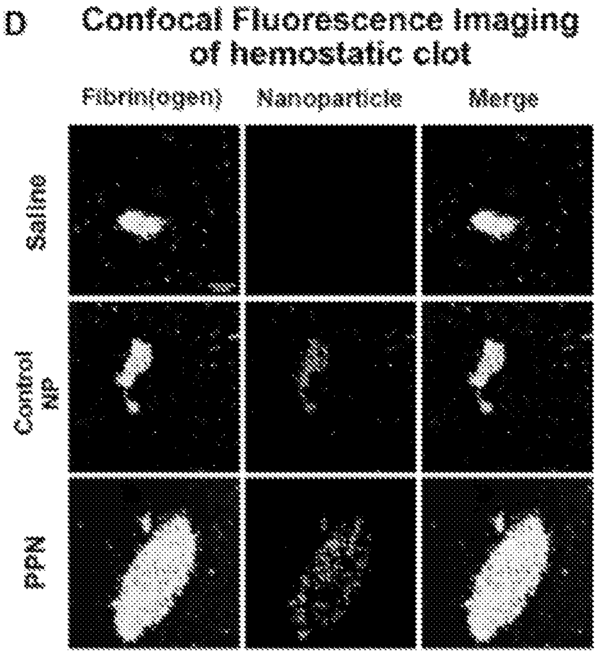
Figure 7E:
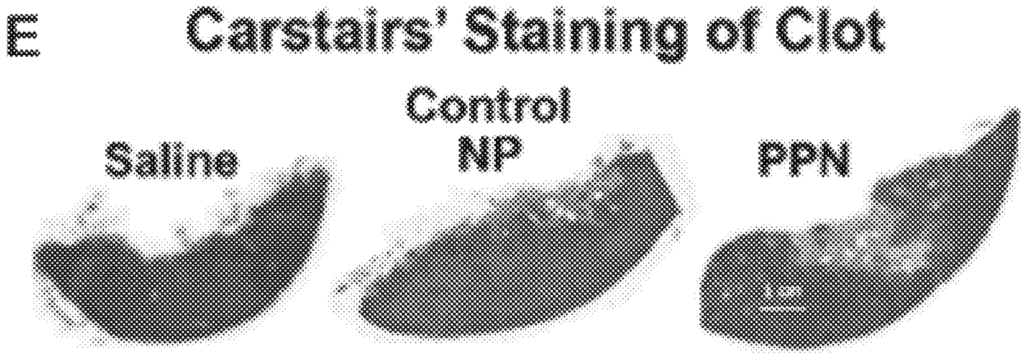
Figure 23:
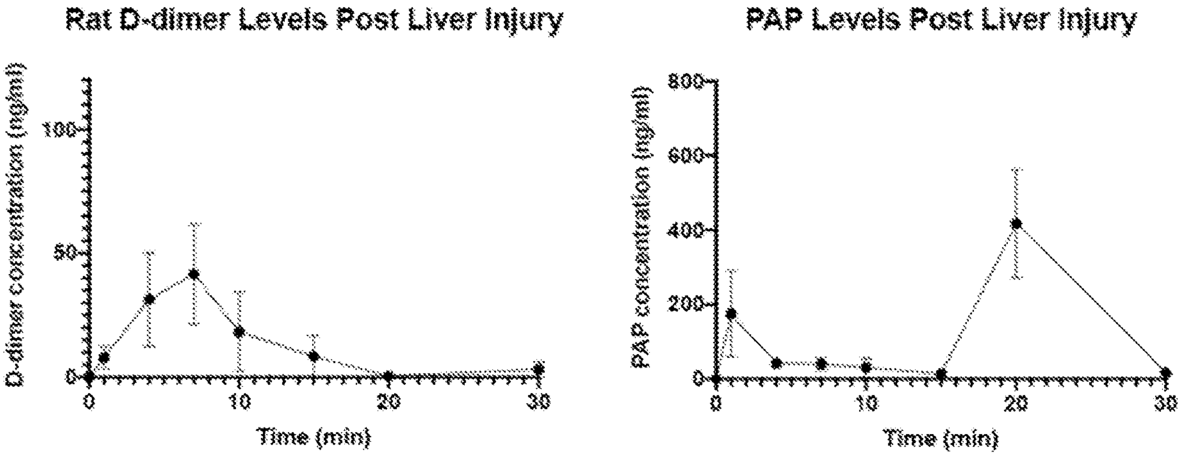
FIG. 23 illustrates Fibrin D-Dimer analysis and plasmin-antiplasmin (PAP) analysis by ELISA of rat blood at 0-30 min post liver resection traumatic injury in the rats (n=4) indicates elevated fibrin degradation and elevated plasmin amounts, which are characteristic of elevated fibrinolytic state.
Figure 24:
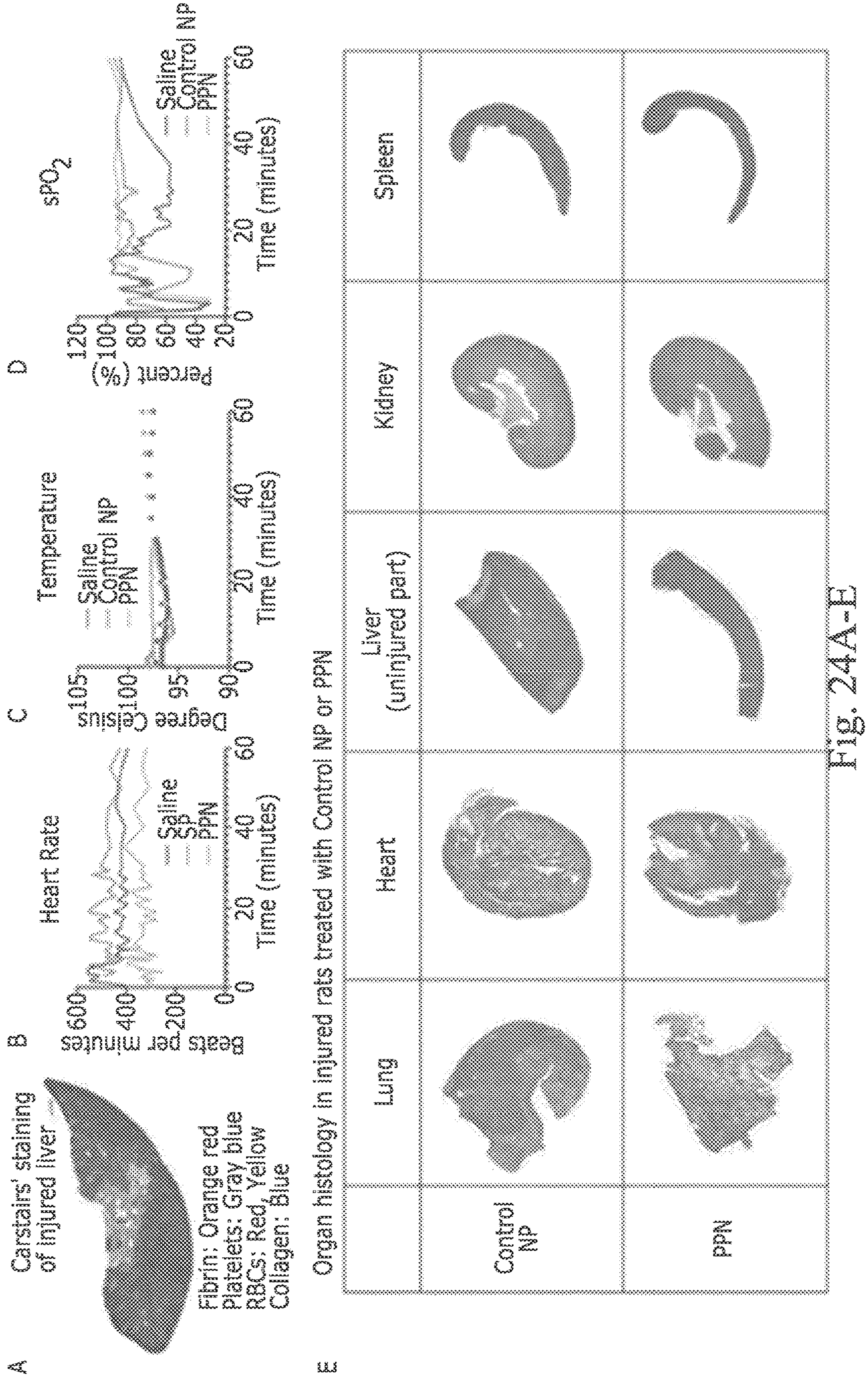
FIGS. 24(A-E) illustrate A: Carstairs' staining of clot at liver injury site; B: Heart rate, C: Temperature and D: Peripheral oxygen saturation ($sPO_2$) of injured rats treated with saline, Control NP or PPN; E: Histology of organs in rats treated with Control NP or PPN show no systemic thrombosis risk.
Figure 25:
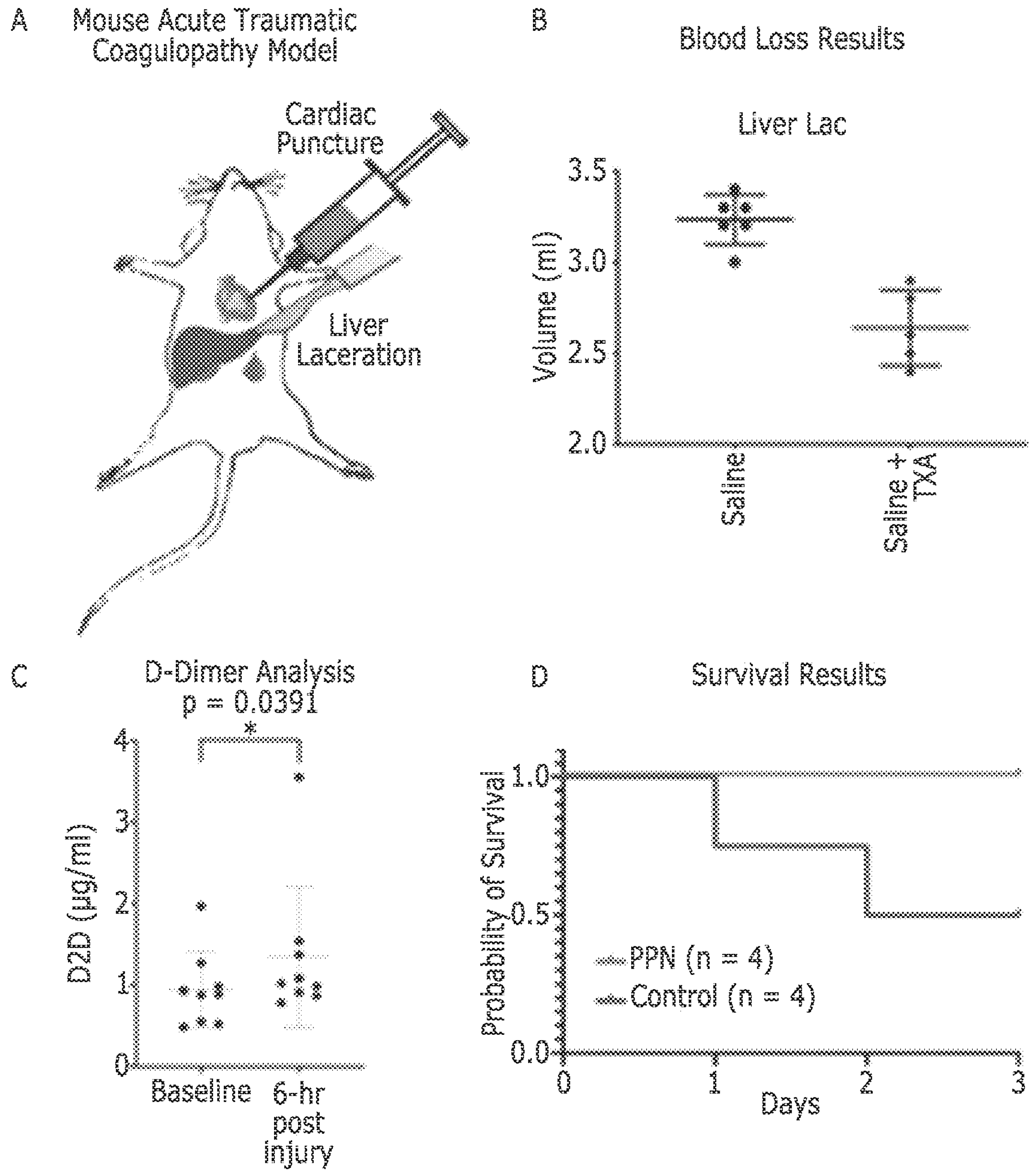
FIGS. 25(A-D) illustrate A: Mouse model of acute traumatic coagulopathy, combining liver laceration with cardiac puncture; B: I.V. TXA dose in this model reduces blood loss, which indicates that the model has fibrinolytic dysfunction of hemostasis; C: Elevated D-Dimer 6-hour post injury further corroborates the persistent fibrinolytic defect; D: PPN treatment via tail vein (2 mg/Kg) 30 min prior to injuries resulted in 100% survival over 3-day period compared to ~50% survival for control (n=4 per group), indicating potential survival benefit with PPN due to hemostatic improvement.
Figure 26:
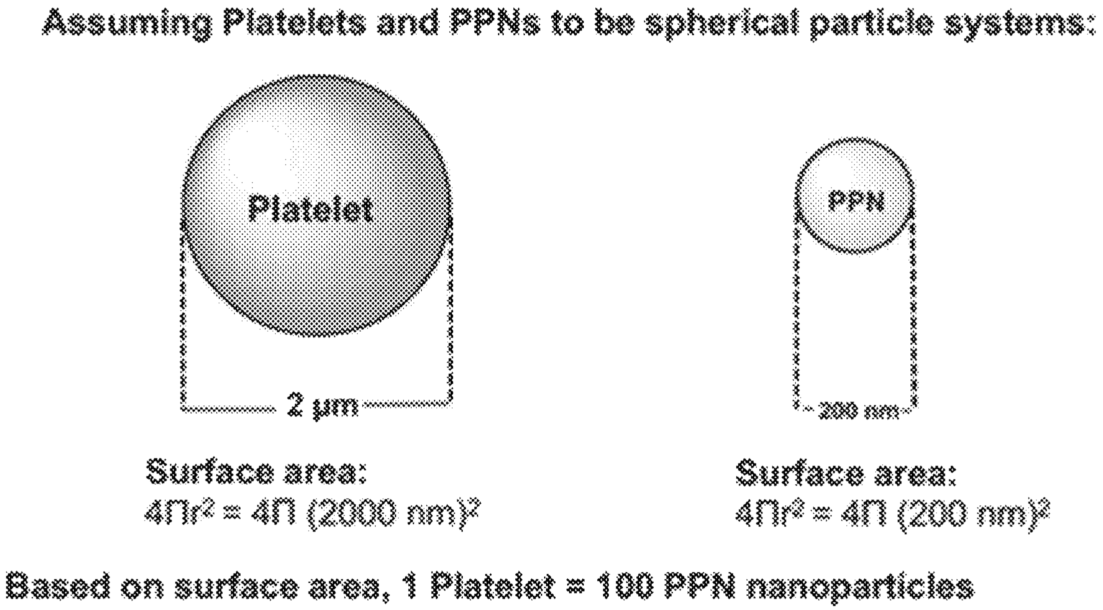
FIG. 26 illustrates theoretical assumption for platelet: particle ratio to be 1:100 for functional equivalency: Since the hemostatic aspects of platelets that are functionally mimicked PPN nanoparticles essentially involve surface-mediated interactions (binding to vWF, binding to collagen, binding to platelet $\alpha IIb\beta 3$ and procoagulant phosphatidylserine exposure), therefore the theoretical assumption is that a platelet: particle ratio in 1:100 range will be functionally 'surface-equivalent'.

An acute liver injury model in Sprague Dawley rats (FIG. 7A) was used to evaluate the ability of PPNs (2 mg/kg dose) administered by tail vein injection to treat traumatic hemorrhage. In this model, blood loss was measured at 1 hour after treatment and survival was monitored for up to 3 hours after treatment. D-dimer and plasmin-antiplasmin analyses of blood samples at early time points (0-30 minutes post injury) in this rat model confirmed high fibrinolysis (FIG. 23). Treatment with control nanoparticles (liposomes containing all other lipid and lipid-peptide components of PPNs but not DSPS or Cholesterol-KTFKC (SEQ ID NO: 4)-PEG) was able to reduce blood loss by ~25% compared to saline treatment (FIG. 7B). Treatment with PPNs reduced blood loss still further, by ~38% ($p \leq 0.05$) (FIG. 7B). In a 3-hour survival analysis, injured rats treated with PPNs showed 100% survival, whereas those treated with control nanoparticles showed 80% survival and those treated with saline showed 60% survival (FIG. 7C). Representative fluorescence images showed that PPNs became incorporated efficiently into hemostatic clots (FIG. 7D). Corresponding histology analysis using Carstairs' staining indicated that PPN-treated animals had more fibrin-rich clots (orange-red staining, FIG. 7E; FIG. 24A) compared to saline-treated or control nanoparticle-treated animals. PPN administration did not affect rat vital signs such as heart rate, temperature or $SPO_2$ (FIG. 24B-D). An initial perturbation of $SPO_2$ (a measure of peripheral oxygenation) was observed in all animals for 5-10 minutes after hemorrhagic injury, but stabilized as soon as the hemostatic response started to reduce the hemorrhage. This stabilization occurred slightly faster in the PPN-treated animals compared to saline-treated or control nanoparticle-treated animals (FIG. 24D). No systemic thrombosis was observed in other organs in the post-euthanasia analysis after the 3-hour observation period (FIG. 24E). Further studies were carried out in a murine acute traumatic coagulopathy model involving liver laceration and cardiac puncture (FIG. 25A-C) in a small group of animals (n=4 per group). We monitored whether PPN treatment (administered 30 minutes before injury) could improve survival over 3 days. Treatment with PPNs led to 100% survival over the 3-day period, compared to 50% for the saline control group (FIG. 25D).

In this example, we describe a next generation platelet surrogate, termed PPN, that not only enabled platelet-mimetic adhesion and aggregation functions, but also incorporated phosphatidylserine into the nanoparticles for thrombin-amplifying procoagulant function. In this PPN design, phosphatidylserine is exposed at the surface of PPNs in the presence of high plasmin locally at the injury site enabling site-specific enhancement of procoagulant hemostatic activity. This design is advantageous in treating trauma-induced hyperfibrinolysis where high amounts of tPA production and plasmin generation occur at the injury site. Our in vitro studies confirmed that under no or low plasmin conditions the phosphatidylserine exposure on PPNs was minimal, whereas at high plasmin concentrations, the PEG cloak on PPNs was removed to enable high exposure of phosphatidylserine that could amplify thrombin generation even in the absence of native platelets. Circulating active plasmin is rapidly inhibited by antiplasmin and α2-macroglobulin, whereas at the injury site the plasmin produced from plasminogen by fibrin-localized tPA is protected from rapid inhibition. Therefore, we rationalized that the local plasmin concentration at an injury site would be high enough to cleave off the PEG cloak and expose the phosphatidylserine on PPNs, enabling procoagulant function. We show that PPN-generated thrombin could enhance fibrin generation, and preserve clot morphology and stability even under fibrinolytic conditions. Our finding that adding DSPS directly (not pre-assembled into PPNs) to plasma did not improve thrombin generation, suggested that spatial presentation of phosphatidylserine in 'patches' at the PPN surface mimicking the membrane surface of procoagulant platelets is important for its function.

Our PPNs circulated in mice in vivo without risk of thrombosis most likely because the phosphatidylserine of PPNs remained unexposed until the PEG cloak was removed by injury site-localized plasmin. Our in vivo rodent studies demonstrated that PPNs provided hemostatic benefit to stanch bleeding in thrombocytopenic mice at a level comparable to that for syngeneic platelets. Our in vivo studies in the rat acute liver injury model and mouse acute hemorrhagic trauma model further demonstrated the hemostatic capability of PPNs, with improved survival of PPN-treated animals compared to saline-treated or control nanoparticle-treated animals. Notably, the saline control was a no treatment control as the saline was administered at the same injection volume as the PPN solution and not at a resuscitation volume. Saline-based hypotensive resuscitation remains relevant in pre-hospital management of patients with acute hemorrhage, because blood product transfusion is currently not available outside a hospital setting. Also, it is important to note that in our in vitro and in vivo studies the control nanoparticles showed partial hemostatic benefit because these nanoparticles were our original platelet surrogate design, that is, liposomes that mimicked platelet adhesion and aggregation. The PPNs used in the current study substantially augmented hemostatic benefit compared to the original platelet surrogate particles due to the ability of exposed phosphatidylserine to boost procoagulant hemostatic function.

The example further demonstrated that even in plasma completely lacking platelets (platelet-free plasma), PPNs could partly rescue thrombin generation; in the presence of only a small number of endogenous platelets, PPNs could substantially amplify thrombin kinetics. This could be of particular importance in treating trauma-induced or drug-induced platelet dysfunction where native platelets may become hyporesponsive. Also, given that PPNs are liposomes, opportunities exist for the delivery of adjunctive agents (e.g., platelet agonists, antifibrinolytics, coagulation factors) as payloads. Platelet surrogates such as PPNs could be potentially combined with other blood surrogates such as red blood cell mimics to create biosynthetic whole blood.

In conclusion, we have designed and evaluated procoagulant platelet-mimetic nanoparticles that mimic not only the adhesive and aggregation properties of platelets but also the procoagulant hemostatic function of platelets. Translational advancement of PPN technology for the transfusion management of bleeding warrants further investigation.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A composition, the composition comprising a plurality of nanoparticle and/or microparticle constructs, each construct having an outer portion that defines an outer surface of the construct, a plurality of targeting moieties and releasable cloaking agents that are linked to the outer portion and extend from the outer surface, and a plurality of phosphatidylserine phospholipids that extend from and/or define portions of the outer portion, wherein the targeting moieties are configured to specifically bind to target molecules of a cell, tissue, and/or disease site in a subject, and wherein the releasable cloaking agents are configured to mask the phosphatidylserine phospholipids prior to binding of the target moieties to the target molecules and be released from the construct to expose the phosphatidylserine phospholipids upon binding of the target moieties to the target molecules.

2. The composition of claim 1, wherein upon systemic administration of the composition to the subject and prior to binding of the targeting moieties to the target molecules, the cloaking agents inhibit exposure of the phosphatidylserine phospholipids so as to avoid macrophage clearance or systemic procoagulant risk.

3. The composition of claim 2, wherein upon binding of the targeting moieties to the target molecules of the cell, tissue, and/or disease site in the subject, exposed phosphatidylserine phospholipids promote macrophage engulfment and/or a procoagulant response.

4. The composition of claim 1, wherein the cloaking agent comprises a hydrophilic polymer that is releasably linked to the outer portion of the construct.

5. The composition of claim 1, wherein the cloaking agent comprises polyethylene glycol.

6. The composition of claim 1, wherein the cloaking agent is releasably linked to an outer portion of the construct with an enzyme cleavable linker.

7. The composition of claim 6, wherein the enzyme cleavable linker is cleaved by an enzyme that is unique or specific to the target cells, tissue, and/or disease site and/or has a higher concentration or activity compared to the concentration or activity at other cells, tissues, and/or disease sites in the subject.

8. The composition of claim 7, wherein the enzyme comprises at least one of a matrix metalloprotease, plasmin, or thrombin.

9. The composition of claim 6, wherein the enzyme cleavable linker comprises a valine-citrulline linker, KTFKC (SEQ ID NO: 4), or VPLSLYSG (SEQ ID NO: 5).

10. The composition of claim 1, wherein the nanoparticle and/or microparticle construct has a diameter of about 50 nm to about 5 μm.

11. The composition of claim 1, wherein the nanoparticle and/or microparticle constructs are liposomes.

12. The composition of claim 11, wherein the liposomes include a plurality of phospholipids and optionally cholesterol to define a lipid membrane.

13. The composition of claim 12, wherein the phospholipids include distearoylphosphatidylserine (DSPS) and at least one of distearoylphosphatidylcholine dipalmitoylphosphatidylcholine (DSPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

14. The composition of claim 13, wherein the distearoylphosphatidylserine (DSPS) comprises about 1 mole % to about 20 mole % of the lipid membrane.

15. The composition of claim 1, wherein the targeting moieties include a plurality of peptides, the peptides including a plurality of von Willebrand factor-binding peptides (VBPs), collagen-binding peptides (CBPs) and fibrinogen mimetic peptides (FMPs).

16. The composition of claim 15, wherein the VBPs, CBPs, and FMPs can be spatially or topographically arranged on the outer surface such that the VBPs, CBPs, and FMPs do not spatially mask each other and the construct is able to adhere to a vascular surface, vascular disease site, and/or vascular injury site with exposed vWF and collagen and promote arrest and aggregation of active platelets onto sites of the construct adhesion.

17. The composition of claim 13 wherein the VBPs, CBPs, and FMPs are conjugated to the outer surface with PEG linkers.

18. The composition of claim 13, wherein the nanoparticle and/or microparticle construct has shape, size and elastic modulus that facilitates margination to a vascular wall and their bio-interactions upon administration to a vasculature of a subject.

19. The composition of claim 13, the VBPs have an amino acid sequence of SEQ ID NO: 1, the CBPs have an amino acid sequence of SEQ ID NO: 2, and the FMPs have an amino acid sequence of SEQ ID NO: 3.

20. The composition of claim 13, wherein the ratio of VPBs to CPBs provided on the outer surface is about 70:30 to about 30:70.

21. The composition of claim 13, wherein the ratio of VPB:CPB:FMP is about 1:1:2 to 1:2:1 to 2:1:1.

* * * * *